United States Patent
Tsao et al.

(10) Patent No.: US 7,579,156 B2
(45) Date of Patent: Aug. 25, 2009

(54) FLUORESCENT PHOSPHOLIPASE ASSAY, PHOSPHOLIPASE A2 INHIBITOR AND STIMULATOR, AND THE USE THEREOF

(75) Inventors: Francis H. C. Tsao, Madison, WI (US); Keith C. Meyer, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 824 days.

(21) Appl. No.: 10/365,738

(22) Filed: Feb. 12, 2003

(65) Prior Publication Data

US 2003/0219849 A1 Nov. 27, 2003

Related U.S. Application Data

(60) Provisional application No. 60/357,188, filed on Feb. 13, 2002, provisional application No. 60/407,114, filed on Aug. 30, 2002.

(51) Int. Cl.
*G01N 33/53* (2006.01)
*G01N 33/543* (2006.01)

(52) U.S. Cl. .................. 435/7.1; 436/501; 436/506; 436/518; 424/1.11; 424/1.21

(58) Field of Classification Search ............... 435/701; 436/501, 506, 518; 424/1.11, 1.21
See application file for complete search history.

(56) References Cited

U.S. PATENT DOCUMENTS

| 4,444,879 A | * | 4/1984 | Foster et al. | ............... 435/7.95 |
| 4,668,623 A | | 5/1987 | Kinnunen et al. | |
| 6,143,545 A | | 11/2000 | Clausen et al. | |
| 6,180,596 B1 | | 1/2001 | Tsao | |

FOREIGN PATENT DOCUMENTS

| EP | 0 037 583 | 10/1981 |
| JP | 04-282391 | 10/1992 |
| WO | WO-00/67025 | 11/2000 |

OTHER PUBLICATIONS

Wang (Annu. Rev. Plant Mol. Biol., 2001,52 pages 211-231.*
Mustonen et al. (Biochemistry, 1993, vol. 32, pp. 53-73-5380).*
Blanchard et al. (Analytical Biochemistry, vol. 222, pp. 435-440, 1994).*
El-Hariri et al. (Journal of Pharm. Pharmacol., 1992, vol. 44, pp. 651-654).*
Kisel et al. (Biochemistry(Moscow), Feb. 2001, vol. 66, No. 2., pp. 168-172).*
Wichmann et al. (Chemical Communications, 2001, vol. 23, pp. 2500-2501).*
Tsao, Francis H.C. "Purification and characterization of two rabbit lung Ca 2+ -dependent phospholipid-binding proteins." Biochimica et Biophysica Acta, 1045 (1990), p. 29-39.
Tsao, Francis H.C., et al. "Lung-calcium-dependent phospholipid-binding proteins: structure and function." Biochimica et Biophysica Acta, 1081 (1991), p. 141-150.
Conricode, Kevin M., et al. "Mechanism for the inhibitory and stimulatory actions of proteins on the activity of phospholipase A2." Biochimica et Biophysica Acta, 1003 (1989), p. 36-43.
Cantin, Andre. et al. "Granulocyte Elastase-Mediated Proteolysis of Alpha1-Antitrypsin in Cystic Fibrosis Bronchopulmonary Secretions." Pediatric Pulmonology, 7 (1989), p. 12-17.
Fuller Noel, J.K., et al. "Bovine Mercaptalbumin and Non-mercaptalbumin Monomers." Journal of Biological Chemistry, 247:22 (1972), p. 7391-7406.
Cantin, Andre M., et al. "Antineutrophil Elastase Activity in Cystic Fibrosis Serum." Pediatric Pulmonology, 11 (1991), p. 249-253.
Tsao, Francis H.C., et al. "Degradation of Annexin I in Bronchoalveolar Lavage Fluid from Patients with Cystic Fibrosis." Am. J. Respir. Cell Mol. Biol., 18 (1998). p. 120-128.
Meshulam, Tova, et al. "Flow Cytometric Kinetic Measurements of Neutrophil Phospholipase A Activation." Journal of Biological Chemistry, 267:30 (1992), p. 21465-21470.
Kim, Tae-Suk, et al. "Identification of a Human cDNA Clone for Lysosomal Type Ca 2+-independent Phospholipase A2 and Properties of the Expressed Protein." Journal of Biological Chemistry, 272:4 (1997), p. 2542-2550.
Blanchard et al., A Fluorescence-Based Assay for Human Type II Phospholipase A2. Analytical Biochemistry 222, 435-440, 1994.
Radvanyi, et al. Anal Biochem. Feb. 15, 1989. vol. 177, No. 1, pp. 103-109, Abstract.
Thuren et al. Fluorometric assay for phospholipase A2 in serum. Clinical Chemistry. May 1985, vol. 31, No. 5, pp. 714-717, Abstract.

* cited by examiner

*Primary Examiner*—Lisa V Cook
(74) *Attorney, Agent, or Firm*—Quarles & Brady, LLP

(57) ABSTRACT

A fluorescent phospholipase assay is disclosed. Further disclosed are the identification of alpha-1-antitrypsin as a phospholipase $A_2$ stimulator and phospholipase C inhibitor and the identification of mercaptalbumin as a phospholipase $A_2$ inhibitor. Various applications involving the use of the phospholipase assay, alpha-1-antitrypsin and mercaptalbumin are also disclosed.

14 Claims, 35 Drawing Sheets

Column
1: PLA2 (4)
2: PLA2 + CF BALF (4)
3: PLA2 + CF BALF (37 C 1 h) (4)
4: CF BALF (8)
5: PLA2 + NV BALF (4)

Column
1: PLA2 (5)
2: PLA2 + 25 ug CF BALF (heat) (3)
3: PLA2 + 50 ug CF BALF (heat) (3)
4: PLA2 + 100 ug CF BALF (heat) (3)
5: PLA2 + 100 ug CF BALF (no heat) (3)

Column
1: PLA2 (4)
2: PLA2 + CF BAL (4)
3: PLA2 + CF BAL + Annexin I (4)
4: PLA2 + CF BAL + 33 kD PLBP (4)
5: PLA2 + Annexin I (4)

SEQUENCE LISTING

<160> NUMBER OF SEQ ID NOS: 22

<210> SEQ ID NO 1
<211> LENGTH: 394
<212> TYPE: PRT
<213> ORGANISM: Homo sapiens

<400> SEQUENCE: 1

```
Glu Asp Pro Gln Gly Asp Ala Ala Gln Lys Thr Asp Thr Ser His His
 1               5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Ala Ala Phe Ala Met Leu
    50                  55                  60

Ser Leu Gly Ala Lys Gly Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
```

```
            195                 200                 205
His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 6
<212> TYPE: PRT
<213> ORGANISM: Homo sapiens

<400> SEQUENCE: 2

Ile Val Asp Leu Val Lys
 1               5

<210> SEQ ID NO 3
<211> LENGTH: 9
<212> TYPE: PRT
<213> ORGANISM: Homo sapiens

<400> SEQUENCE: 3

Leu Ser Ser Trp Val Leu Leu Met Lys
 1               5

<210> SEQ ID NO 4
<211> LENGTH: 10
<212> TYPE: PRT
<213> ORGANISM: Homo sapiens

<400> SEQUENCE: 4

Leu Ser Ile Thr Gly Thr Tyr Asp Leu Lys
 1               5                  10

<210> SEQ ID NO 5
<211> LENGTH: 14
<212> TYPE: PRT
<213> ORGANISM: Homo sapiens

<400> SEQUENCE: 5
```

```
Gly Thr Glu Ala Ala Gly Ala Met Phe Leu Glu Ala Ile Pro
 1               5                  10
```

```
<210> SEQ ID NO 6
<211> LENGTH: 14
<212> TYPE: PRT
<213> ORGANISM: Homo sapiens

<400> SEQUENCE: 6

Ile Thr Pro Asn Leu Ala Glu Phe Ala Phe Ser Leu Tyr Arg
 1               5                  10
```

```
<210> SEQ ID NO 7
<211> LENGTH: 14
<212> TYPE: PRT
<213> ORGANISM: Homo sapiens

<400> SEQUENCE: 7

Val Phe Ser Asn Gly Ala Asp Leu Ser Gly Val Thr Glu Glu
 1               5                  10
```

```
<210> SEQ ID NO 8
<211> LENGTH: 14
<212> TYPE: PRT
<213> ORGANISM: Homo sapiens

<400> SEQUENCE: 8

Thr Leu Asn Gln Pro Asp Ser Gln Leu Gln Leu Thr Thr Gly
 1               5                  10
```

```
<210> SEQ ID NO 9
<211> LENGTH: 4
<212> TYPE: PRT
<213> ORGANISM: Homo sapiens

<400> SEQUENCE: 9

Phe Gly Glu Arg
 1
```

```
<210> SEQ ID NO 10
<211> LENGTH: 7
<212> TYPE: PRT
<213> ORGANISM: Homo sapiens

<400> SEQUENCE: 10

Tyr Leu Tyr Glu Ile Ala Arg
 1               5
```

```
<210> SEQ ID NO 11
<211> LENGTH: 9
<212> TYPE: PRT
<213> ORGANISM: Homo sapiens

<400> SEQUENCE: 11

Gln Thr Ala Leu Val Glu Leu Val Lys
 1               5
```

```
<210> SEQ ID NO 12
<211> LENGTH: 10
<212> TYPE: PRT
<213> ORGANISM: Homo sapiens

<400> SEQUENCE: 12

Leu Val Asn Glu Val Thr Glu Phe Ala Lys
 1               5                  10
```

```
<210> SEQ ID NO 13
<211> LENGTH: 12
<212> TYPE: PRT
<213> ORGANISM: Homo sapiens

<400> SEQUENCE: 13

Ala Val Met Asp Asp Phe Ala Ala Phe Val Glu Lys
 1               5                  10

<210> SEQ ID NO 14
<211> LENGTH: 14
<212> TYPE: PRT
<213> ORGANISM: Homo sapiens

<400> SEQUENCE: 14

Lys Val Pro Gln Val Ser Thr Pro Thr Leu Val Glu Val Ser
 1               5                  10

<210> SEQ ID NO 15
<211> LENGTH: 14
<212> TYPE: PRT
<213> ORGANISM: Homo sapiens

<400> SEQUENCE: 15

Arg Pro Cys Phe Ser Ala Leu Glu Val Asp Glu Thr Tyr Val
 1               5                  10

<210> SEQ ID NO 16
<211> LENGTH: 14
<212> TYPE: PRT
<213> ORGANISM: Homo sapiens

<400> SEQUENCE: 16

Val Phe Asp Glu Phe Lys Pro Leu Val Glu Glu Pro Gln Asn
 1               5                  10

<210> SEQ ID NO 17
<211> LENGTH: 4
<212> TYPE: PRT
<213> ORGANISM: Homo sapiens

<400> SEQUENCE: 17

Leu Val Asp Lys
 1

<210> SEQ ID NO 18
<211> LENGTH: 4
<212> TYPE: PRT
<213> ORGANISM: Homo sapiens

<400> SEQUENCE: 18

Glu Leu Asp Arg
 1

<210> SEQ ID NO 19
<211> LENGTH: 5
<212> TYPE: PRT
<213> ORGANISM: Homo sapiens

<400> SEQUENCE: 19

Val Pro Met Met Lys
 1               5
```

```
-continued

<210> SEQ ID NO 20
<211> LENGTH: 7
<212> TYPE: PRT
<213> ORGANISM: Homo sapiens

<400> SEQUENCE: 20

Ser Pro Leu Phe Met Gly Lys
 1               5

<210> SEQ ID NO 21
<211> LENGTH: 8
<212> TYPE: PRT
<213> ORGANISM: Homo sapiens

<400> SEQUENCE: 21

Gln Ile Asn Asp Tyr Val Glu Lys
 1               5

<210> SEQ ID NO 22
<211> LENGTH: 14
<212> TYPE: PRT
<213> ORGANISM: Homo sapiens

<400> SEQUENCE: 22

Leu Gln His Leu Glu Asn Glu Leu Thr His Asp Ile Ile Thr
 1               5                  10
```

FLUORESCENT PHOSPHOLIPASE ASSAY, PHOSPHOLIPASE A2 INHIBITOR AND STIMULATOR, AND THE USE THEREOF

CROSS-REFERENCE TO RELATED APPLICATIONS

This application claims the benefit of U.S. provisional application Ser. No. 60/357,188, filed on Feb. 13, 2002 and U.S. provisional application Ser. No. 60/407,114, filed on Aug. 30, 2002.

STATEMENT REGARDING FEDERALLY SPONSORED RESEARCH OR DEVELOPMENT

This invention was made with United States government support awarded by the following agency: NIH, grant numbers HL38744 and AI48624. The United States has certain rights in this invention.

BACKGROUND OF THE INVENTION

The inflammatory response governs a wide range of illness from injury to infections and allergies. Initiation of inflammation involves the activation of immune cells that increases synthesis and release of certain cytokines. The released cytokines further activate the appropriate target cells and trigger the phospholipase $A_2$ ($PLA_2$)-involved inflammatory processes. $PLA_2$s are a diverse family of enzymes that hydrolyze the sn-2 fatty acyl bond of phospholipids producing free fatty acids and lysophospholipids (lysoPLs). These enzymes are abundant in pancreatic juice and venoms of snakes and bees. They are also present in small amounts in many types of cells. $PLA_2$s have a wide range of functions involving dietary phospholipid digestion, cellular phospholipid metabolism and turnover, membrane phospholipid remodeling, and the critical roles in the inflammatory processes. $PLA_2$ is a key enzyme regulating the synthesis of a number of bioactive lipid mediators including prostaglandins (PG), thromboxanes (TX) and leukotrienes (LT), collectively called eicosanoids, and platelet activating factor (PAF). Eicosanoids are synthesized from a common precursor of $PLA_2$ enzymatic product, arachidonic acid (AA) released from the sn-2 position of cell membrane phospholipids hydrolyzed by $PLA_2$. These potent lipid mediators play important roles in inflammatory processes and numerous critical illnesses (1, 2). For example, excessive production of these mediators has been linked to inflammation, allergy, brain injury, cancer development and metastasis, and cardiovascular disorders (39, 46, 48). When inflammation occurs in the lung, activated immune response cells release the inflammatory lipid mediators that can induce airway hyperresponsiveness, act as nonspecific chemoattractants to increase leukocyte recruitment, and cause vascular permeability and bronchoconstriction (3, 4). In addition, $PLA_2$ and its enzymatic reaction product lysoPL present in the extracellular fluids may also cause tissue damage (5-7).

Three types of $PLA_2$ have been found in mammalian tissues, the secretory $PLA_2$, the cytosolic $PLA_2$, and the calcium-independent $PLA_2$ (8). At least ten secretory $PLA_2$ isoforms have been identified in the humans and these enzymes have molecular weights around 14 kDa (8-10). Among these proteins the $PLA_2$-IB and $PLA_2$-IIA have been most extensively studied. $PLA_2$-IB is considered as a pancreatic enzyme whose function mainly involves digestion of dietary phospholipids. $PLA_2$-IIA is a non-pancreatic enzyme and has been found to correlate with local and systemic inflammatory responses (11). This enzyme is present in platelets and inflammatory cells including neutrophils and has been found in circulating blood and rheumatoid arthritic synovial fluid (11-13). The primary structure of human $PLA_2$-IIA in platelets and synovial fluid has been determined and its gene cloned (13, 14). Most secretory $PLA_2$ enzymes including $PLA_2$-IB and $PLA_2$-IIA are not specific for AA at the 2-position of phospholipids, however, a recombinant $PLA_2$ of the recently discovered form namely $PLA_2$-X efficiently released AA from adherent mammalian cells (54). Although, the secretory $PLA_2$ enzymes are not specific for AA at the sn-2 position of phospholipids, its enzymatic products of lysoPL and free fatty acid may further activate a cytosolic $PLA_2$ with molecular weight of 85 kDa which specifically releases AA from membrane phospholipids (15, 16). Both $PLA_2$-I and $PLA_2$-II have been implicated in human diseases, particularly the $PLA_2$-IIA in inflammatory diseases (17). High levels of secretory $PLA_2$-IIA have been found in the plasma of patients with acute sepsis, in synovial fluids from patients with arthritis, and in peritoneal fluids from patients with peritonitis (11, 17). $PLA_2$-IIA may also act as an antibacterial agent to destroy bacteria during infection (18). This is because of the nature of the high cationic charge of $PLA_2$-IIA (pI>10.5) that, in conjunction with bactericidal/permeability-increasing protein, $PLA_2$-IIA can readily penetrate the cell wall of gram-negative bacteria and disrupt the anionic bacterial membrane. Expression of pancreatic $PLA_2$ in the lung (19, 20) and its presence, together with $PLA_2$-IIA, in bronchoalveolar lavage fluid (BALF) (21, 22) suggest a role of $PLA_2$-IB in addition to its function as a digestive enzyme. However, the function of the secretory $PLA_2$ in the lung is not clear.

Despite the various isoforms of secretory $PLA_2$, the catalytic reactions of these enzymes, in terms of phospholipid hydrolysis, are the same, i.e., hydrolyzing the fatty acyl group at the sn-2 position of phospholipids at the air/water interface. They require millimolar calcium for their enzymatic reactions and interact strongly with membranes containing anionic phospholipids but interact weakly with an interface composed of zwitterionic phosphatidylcholine (PC) except $PLA_2$-X, which binds tightly to PC vesicles (54). Once $PLA_2$ is secreted into the extracellular fluid, the enzyme has to interact with the outer plasma membrane of cells to exert its action. The interaction between $PLA_2$ and the cell surface may involve the binding of $PLA_2$ with $PLA_2$-specific receptors or with anionic heparan sulfate proteoglycans (HSPG), or by direct interfacial binding and hydrolyzing of membrane phospholipids (23). Interfacial binding is important for plasma membrane fatty acid release catalyzed by secretory $PLA_2$ (24). The major lipid component of the eukaryotic cell outer membrane is PC with a small amount of sphingomylin. Thus, mammalian cells in general are poor substrates for secretory $PLA_2$s. It is not clear how the secretory $PLA_2$s exert their action on cells in terms of phsopholipid hydrolysis without indiscriminately destroying the cells.

Inhibition of lipid mediator production has long been considered for therapeutic purposes (2). However, drugs that have been developed to inhibit production of target lipid mediators or to restrain $PLA_2$ activity have serious side effects and sometimes even exacerbate the pathological conditions. This is, in part, due to the observation that when a target mediator is inhibited, the inhibited pathway often shifts to unwanted over production of another mediator. Also, complexity of the super-family genes of $PLA_2$ makes drug design to control the specific type of $PLA_2$ that is involved in inflammatory disease more difficult (25).

Cystic fibrosis (CF) is caused by the defect of the gene encoding the CF transmembrane conductance regulator (CFTR), a large, membrane-spanning protein that regulates ion flux through the apical surfaces of epithelial cells. Pulmonary complications due to progressive bronchiectasis are the major cause of morbidity and mortality of the CF patients (26). Lung disease in CF is characterized by bacterial infection and intense, neutrophil-dominated inflammation. Lower respiratory tract secretions of most CF patients contain high amounts of proteases, particularly the elastase from polymorphonuclear neutrophils (PMN). The abundant neutrophil elastase (NE) is thought to be a major cause of the epithelial tissue damage that leads to bronchiectasis and bronchial obstruction (27, 28).

The most potent endogenous inhibitor of NE is alpha-1-antitrypsin ($\alpha$1-AT) (29). The $\alpha$1-AT in the airspaces is thought to protect fragile bronchoalveolar tissues from destruction by NE. However, intact and functional $\alpha$1-AT is primarily deficient in the airspaces of patients with CF. $\alpha$1-AT is a member of the serpin superfamily of proteins. $\alpha$1-AT is a 52 kDa secreted glycoprotein with 394 amino acid residues that is mainly synthesized by hepatocytes and produced in small amounts by other cells including neutrophils and alveolar macrophages (38). $\alpha$1-AT is the most abundant proteinase inhibitor in the plasma, and its normal level ranges from 20 $\mu$M to 50 $\mu$M (38). It inactivates NE in a 1:1 molar ratio to form an $\alpha$1-AT-NE complex. Inherited $\alpha$1-AT deficiency is linked to early onset of emphysema and to liver disease (29). In the inflamed CF lung, the deficiency of $\alpha$1-AT is not due to lack of this protein as occurs in hereditary $\alpha$1-AT. Rather, the deficiency is due to proteolytic cleavage of the intact $\alpha$1-AT to yield a truncated 48 kDa $\alpha$1-AT, which cannot bind and inactivate NE (45). Contrarily, the amount of $\alpha$1-AT in the serum of most CF patients was more than two-times higher than that in healthy persons, and $\alpha$1-AT from sera of patients with CF is fully active against NE (50). Although treatment with exogenous $\alpha$1-AT has been attempted, either by infusion into the systemic circulation or via aerosol inhalation (33), significant clinical benefits of $\alpha$1-AT replacement have not been demonstrated to date.

It has long been recognized that elevation of AA in the lung of patients with CF is linked to the pathogenesis of chronic lung inflammation (30). High AA is also associated with phospholipids in lung tissue of CFTR gene knockout cftr$^{-/-}$ mice (31), and the high level of AA has been linked to low amounts of phospholipid-bound docosahexaenoic acid (DHA) in involved tissues (32). Epithelial cell lines with the deltaF508 mutation in their CFTR gene also released abnormally high levels of AA when induced by $Ca^{2+}$ (31). Little is known about the regulation of the production of the high level of AA and the synthesis of the lipid mediators in the CF lung and airway.

The massive influx of neutrophils into infected CF airways is thought to be induced by a number of substances including bacterial products, LTB4 and interleukin (IL)-8 (33). LTB4 is the most abundant eicosanoid found in CF BALF, together with PG and TX. The levels of all of these lipid mediators are markedly elevated in the airways of patients with CF (34). High levels of LTB4 have also been found in sputum and urine of CF children (35) and sputum of CF adults (36). LTB4 not only acts as a chemoattractant to increase leukocyte recruitment, but it also activates neutrophils to release more elastase. LTB4 also induces airway hyperresponsiveness and causes vascular permeability and bronchoconstriction (4). As a result, a cycle of enhanced LTB4 production from AA, chemoattraction of neutrophils, and intense inflammation due to neutrophil flux into lung tissue occurs and further stimulates LTB4 generation from AA, sustaining chronic inflammation and progressively damaging the CF lung. Also, the function of surfactant in the CF lung is impaired, and the surfactant phospholipid level is low. All these seem to suggest that $PLA_2$-mediated inflammation may play a critical role in the CF lung injury.

To investigate whether the increase in AA in bronchial secretions of CF patients is due to the increase in $PLA_2$ activity, Tsao previously discovered that BALF from subjects with CF markedly induced $PLA_2$ activity in vitro (U.S. Pat. No. 6,180,596) (37). This revealed that there might be a $PLA_2$ stimulating factor in the BALFs of CF subjects.

SUMMARY OF THE INVENTION

In one aspect, the present invention relates to a method of measuring the activity of a phospholipase by using a unique fluorescently labeled liposome disclosed in the present invention, which contains a nonfluorescent phosphatidylcholine (PC), a nonfluorescent, negatively charged molecule selected from a negatively charged phospholipid or a negatively charged organic compound, and a fluorescently labeled molecule selected from a fluorescently labeled PC or a fluorescently labeled, negatively charged phospholipid wherein hydrolizaton of the phospholipid components of the liposome by the phospholipase causes a fluorescence intensity change. The method involves contacting the phospholipase with the liposome and detecting the fluorescence intensity change due to the hydrolization of phospholipid components of the liposome to determine the activity of the phospholipase.

In another aspect, the present invention relates to a kit for measuring the activity of a phospholipase. The kit contains the fluorescently labeled liposome of the present invention and the phospholipase.

In another aspect, the present invention relates to a method for identifying an agent that can alter the activity of a phospholipase. The method involves measuring the phospholipase activity in the presence of a test agent using the method described above. A control group is run in parallel except that the test agent is not included. The phospholipase activity of the test agent group is than compared to that of the control group. A higher than control activity indicates that the agent is a stimulator of the phospholipase and a lower than control activity indicates that the agent is an inhibitor of the phospholipase. This method can be readily adapted to detect the activity of a $PLA_2$ modulator by employing $PLA_2$ as the phospholipase and substituting a $PLA_2$ stimulator for the test agent.

In another aspect, the present invention relates to a method for determining whether a human or non-human animal subject has an abnormally high $PLA_2$ activity. The method involves using the method disclosed in the present invention to measure the $PLA_2$ activity in the presence of a biological sample prepared from the subject for measuring a $PLA_2$ inhibitor activity or a $PLA_2$ stimulator activity. The $PLA_2$ activity is then compared to that of a control that is measured in the absence of the biological sample to determine the $PLA_2$ inhibitor or stimulator activity in the biological sample. Optionally, both the $PLA_2$ inhibitor and stimulator activities in the biological sample are determined. Lastly, the $PLA_2$ inhibitor activity, the $PLA_2$ stimulator activity, or the relative activity of the inhibitor to the stimulator or the stimulator to the inhibitor of the biological sample is compared to a normal range obtained from healthy subjects of the same species. A lower than normal range inhibitor activity or inhibitor to stimulator relative activity, or a higher than normal range stimulator activity or stimulator to inhibitor relative activity indicates that the subject has an abnormally high $PLA_2$ activity.

In another aspect, the present invention relates to another method for determining whether a human or non-human animal subject has an abnormally high $PLA_2$ activity. The method involves measuring the endogenous $PLA_2$ activity of a biological sample prepared from the subject in the presence of a $PLA_2$ stimulator and comparing the $PLA_2$ activity to a normal range obtained from healthy subjects of the same species. A higher than normal range $PLA_2$ activity indicates that the subject has an abnormally high $PLA_2$ activity.

In another aspect, the present invention relates to a method for stimulating the activity of a monomeric $PLA_2$ by exposing the $PLA_2$ to a polypeptide containing a truncated $\alpha 1$-AT in an amount sufficient to increase the activity of the $PLA_2$.

In another aspect, the present invention relates to a method for inhibiting the activity of a monomeric $PLA_2$ by inhibiting the $PLA_2$ stimulatory activity of $\alpha 1$-AT sufficiently to lower the stimulated activity of $PLA_2$.

In another aspect, the present invention relates to another method for determining whether a human or non-human animal subject has an abnormally high $PLA_2$ activity. The method involves determining the amount of mercaptalbumin, the amount of $\alpha 1$-AT or both from an appropriate biological sample prepared from the subject and comparing the amount of mercaptalbumin, the amount of $\alpha 1$-AT, or the relative amount of mercaptalbumin to $\alpha 1$-AT or $\alpha 1$-AT to mercaptalbumin to a normal range obtained from healthy subjects of the same species wherein a lower than normal level or relative level of mercaptalbumin, or a higher than normal level or relative level of $\alpha 1$-AT indicates the subject has an abnormally high $PLA_2$ activity In another aspect, the present invention relates to a method for diagnosing lung inflammation in CF patients by determining the presence of a truncated $\alpha 1$-AT in bronchial tubes, BALF or sputum.

In another aspect, the present invention relates to a method for treating a disorder associated with an abnormally high level of $PLA_2$ activity in a human or nonhuman animal subject by inhibiting the $PLA_2$ stimulatory activity of $\alpha 1$-AT in the subject.

In another aspect, the present invention relates to a method for inhibiting $PLA_2$ activity by exposing $PLA_2$ to a polypeptide containing mercaptalbumin in an amount sufficient to inhibit $PLA_2$ activity.

In another aspect, the present invention relates to a method for stimulating $PLA_2$ activity by inhibiting the $PLA_2$ inhibitory activity of mercaptalbumin sufficient to stimulate the inhibited $PLA_2$ activity.

In another aspect, the present invention relates to another method for treating a disorder associated with an abnormally high level of $PLA_2$ activity in a human or nonhuman animal subject by increasing the $PLA_2$ inhibitory activity of mercaptalbumin in the subject.

In another aspect, the present invention relates to a method for identifying an agent that can alter the $PLA_2$ stimulatory activity of $\alpha 1$-AT or the $PLA_2$ inhibitory activity of mercaptalbumin. The method involves exposing a composition that contains a $PLA_2$ and $\alpha 1$-AT or mercaptalbumin to a test agent and measuring the $PLA_2$ activity of the composition. A control group is run in parallel except that the test agent is not included. Then, the $PLA_2$ activity of the test agent group is compared to that of the control group, and if a difference is observed, the test agent is further tested to eliminate the possibility that it modulates the activity of $PLA_2$ directly.

In another aspect, the present invention relates to a method for inhibiting phospholipase C (PLC) activity by exposing PLC to a polypeptide containing $\alpha 1$-AT in an amount sufficient to inhibit PLC activity.

In another aspect, the present invention relates to a method for stimulating PLC activity by inhibiting PLC inhibitory activity of $\alpha 1$-AT sufficiently to stimulate the inhibited PLC activity.

In another aspect, the present invention relates to a method for identifying an agent that can alter the PLC inhibitory activity of $\alpha 1$-AT. The method involves exposing a composition that contains PLC and $\alpha 1$-AT to a test agent, measuring the PLC activity of the composition, and comparing the PLC activity to that of a control composition that is not exposed to the test agent. If a difference is observed, the test agent should be further tested to eliminate the possibility that it modulates the PLC activity directly.

In another aspect, the present invention relates to a method of measuring the activity of a lipase. The method involves contacting PLC with a liposome of the present invention in which the fluorescently labeled molecule contains a fluorescently labeled fatty acid moiety. Diacylglycerol will form by the action of PLC. The lipase is then brought into contact with diacylglycerol leading to the release fluorescent-labeled fatty acids and hence an increase in fluorescence intensity. The increase in fuorescence intensity is monitored for determination of the lipase activity.

DETAILED DESCRIPTION OF THE INVENTION

Figure 1:
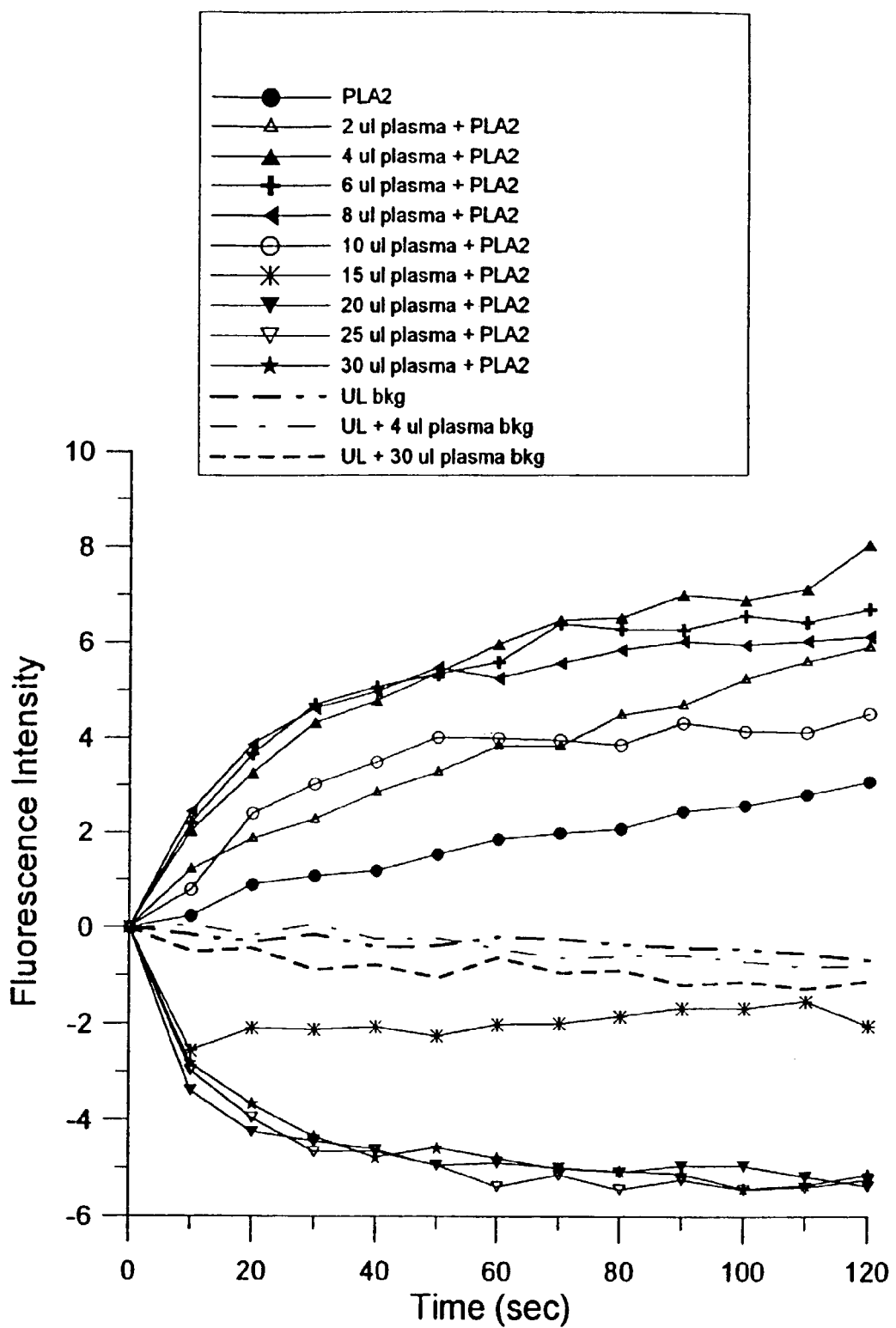
FIG. 1 shows the presence of $PLA_2$-stimulator ($PLA_2$-s) and $PLA_2$-inhibitor ($PLA_2$-i) activity in human plasma.

The term "biological sample" is used in the specification and claims to mean a tissue or fluid sample from a human or non-human animal subject, a sample from cultured cells or culture medium, or a preparation derived from any of the foregoing.

The term "$PLA_2$ modulator" is used in the specification and claims to encompass both $PLA_2$ stimulators and $PLA_2$ inhibitors.

The term "α1-AT" is used in the specification and claims to mean the full length α1-AT, a truncated form of α1-AT or both. A truncated form of α1-AT is an α1-AT that is shorter than the full length α1-AT but at minimum contains the amino acid sequence of 16His to 357Pro of SEQ ID NO:1 or its equivalent in other α1-AT sequences.

The term "substantially pure" is used in the specification and claims to describe preparations of $PLA_2$ or $PLA_2$ stimulators or inhibitors that are purified to a degree so that any impurities contained therein do not interfere with any of the assays of the present invention to an unacceptable level.

Presented below is a new fluorescent assay for measuring the activity of a phospholipase. Using the assay, the inventors successfully detected $PLA_2$ stimulating and inhibiting activities in a variety of biological samples such as plasma, serum and BALF collected from healthy individuals and individuals who suffered from inflammation symptoms. The inventors further identified that the $PLA_2$ stimulating activity is from either albumin or α1-AT and the $PLA_2$ inhibiting activity is from a specific form of albumin, mercaptalbumin. It has long been known that albumin inhibits $PLA_2$ activity by depleting the substrate or stimulates $PLA_2$ activity by relieving product inhibition, depending on the assay conditions (44). What is new here is the identification of α1-AT as a new $PLA_2$ stimulator and mercaptalbumin, but not other albumins, as a $PLA_2$ inhibitor. As other albumins, mercaptalbumin acts as a $PLA_2$ stimulator at low concentrations by relieving product inhibition. However, at high concentrations, mercaptalbumin acts as a $PLA_2$ inhibitor. Without intending to be limited by theory, the inventors believe that mercaptalbumin inhibits $PLA_2$ activity by blocking $PLA_2$'s action on cellular membranes; the inventors further provide evidence that α1-AT stimulates $PLA_2$ activity by binding to the head group of phospholipids (especially negatively charged phospholipids) so that the phospholipid molecules rearrange to a loose form to allow $PLA_2$ penetration and hydrolyzation of the fatty acyl groups.

As shown in the examples below, $PLA_2$ stimulator and inhibitor activities could be detected in the plasma and serum of both healthy individuals and CF or COPD patients with lung inflammation. While the $PLA_2$ stimulator activity for healthy and CF or COPD individuals are about the same, the inhibitor activity is lower in the CF and COPD patients. When BALF collected from CF and COPD patients were tested for $PLA_2$ stimulator and inhibitor activities, only stimulator but not inhibitor activity was detected. The $\alpha1$-AT in the plasma and serum is the full length $\alpha1$-AT and the stimulator activity in the plasma and serum is a reflection of the total stimulator activity of albumin and $\alpha1$-AT. The stimulator activity in the BALF of the CF and COPD patients is that of a truncated $\alpha1$-AT as only the truncated $\alpha1$-AT was found in the BALF. CF or COPD patients have higher plasma and serum $\alpha1$-AT levels than healthy individuals but their plasma and serum albumin levels are about the same as healthy individuals. Since albumin is much more abundant in plasma and serum than $\alpha1$-AT, the total $PLA_2$ stimulator activity, which include that of both albumin and $\alpha1$-AT, are about the same in healthy and CF or COPD individuals. The inventors found that the $PLA_2$ stimulatory and inhibitory activities of albumin are heat sensitive and the $PLA_2$ stimulatory activity of $\alpha1$-AT is heat resistant. Thus, one can detect the difference in $\alpha1$-AT $PLA_2$ stimulatory activity between healthy individuals and CF or COPD patients by heat inactivating albumin in the plasma and serum.

The new fluorescent phospholipase assay and the identification $\alpha$-AT and mercaptalbumin as a $PLA_2$ stimulator and inhibitor respectively provide new tools for diagnosis and treatment of disorders that are associated with an increase in $PLA_2$ activity in human and non-human animals.

I. Fluorescent Phospholipase Assay

A. Measuring the Activity of a Phospholipase

In one aspect, the present invention relates to a method of measuring the activity of a phospholipase such as $PLA_2$, phospholipase $A_1$ ($PLA_1$), phospholipase C (PLC), and phospholipase D (PLD). A common feature of all these phospholipases is their ability to hydrolyze PC and negatively charged phospholipids. For example, $PLA_2$ hydrolyzes the fatty acyl group at the sn-2 position of phosphatidylcholine (PC) and $PLA_1$ hydrolyzes the fatty acyl group at the sn-1 position of PC; PLC hydrolyzes PC to yield 1,2-diacylglycerol and choline phosphate and PLD releases choline from PC to produce phosphatidic acid. To measure the activity of a phospholipase, the present invention provides a unique liposome that contains a nonfluorescent PC, at least one of a nonfluorescent/negatively charged phospholipid and a nonfluorescent/negatively charged organic compound, and at least one of a fluorescently labeled PC and a fluorescently labeled/negatively charged phospholipid, wherein hydrolizaton of the phospholipid components of the liposome by a phospholipase causes a fluorescence intensity change. The change can be an increase or decrease depending on the particular phospholipase and the specific group labeled in the PC or the phospholipid. For example, when a liposome that contains dioleoyl phosphatidylcholine (DOPC), phosphatidylglycerol (PG) and fluorescently labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) is used, the action of a $PLA_2$ leads to an increase in fluorescence intensity by releasing the fluorescent group the fluorescence from which has initially been quenched in the liposome. On the other hand, the action of a PLC leads to a decrease in fluorescence intensity by liberating 1, 2-diacylglycerols that are more hydrophobic and increase quenching of the fluorescence of the fatty acyl group.

To form a liposome of the present invention, any PC can be used. Examples of PCs that can be used include but are not limited to DOPC, dipalmitoyl PC and PCs with other fatty acyl groups. DOPC is a preferred PC for the purpose of the present invention. PCs obtained from egg yolk, soybean and other sources can all be used. The fluorescently labeled PC and the non-labeled PC can be the same or different. The exact position at which a PC is labeled is not critical so long as fluorescence intensity changes upon hydrolization of the phospholipid components of the liposome by a phospholipase whose activity is being measured. Examples of fluorescently labeled PCs that can be used in the present invention include but are not limited to Bis-BODIPY FL $C_{11}$-PC and 1,2-bis-(1-pyrenebutanoyl)-sn-glycero-3-phosphocholine.

Examples of negatively charged phospholipids that can be used to form the liposome of the present invention include but are not limited to phosphatidylglycerol (PG), phosphatidylserine (PS), phosphatidylinositol (PI), and phosphatidic acid (PA). An example of negatively charged organic compounds that can be used to form the liposome of the present invention is dicetyl phosphate.

Any fluorescently labeled phospholipids (preferably negatively charged), including but are not limited to fluorescently labeled PG, PS, PI and PA, can be used to form the liposome of the present invention. The exact position at which a phospholipid is labeled is not critical so long as fluorescence intensity changes upon hydrolization of the phospholipid components of the liposome by a phospholipase whose activity is being measured.

The liposome of the present invention is preferably but does not have to be unilamellar.

In the method of the present invention, the activity of a phospholipase can be determined based on fluorescence data collected at a single time point or recorded on a continuous basis. The latter provides more reliable results because potential bias due to idiosyncrasies of particular time points can be avoided. The term continuous recordation or continuous measurement is used in the specification and claims to refer to fluorescence intensity recordation at a defined interval or intervals over a specific period time. The defined intervals can be zero second or a longer time period. For instance, a recordation of fluorescence intensity once every 10 sec (defined interval) over a period of two minutes is considered a continuous recordation for the purpose of the present invention.

The advantage of continuous recordation is clearly shown in the examples presented below. For example, in FIG. 6 of Example 1, when 20 µl plasma of subjects with inflamed lungs was included in the $PLA_2$ reaction mixture for measuring $PLA_2$-i activity, it appeared that $PLA_2$ activity was slightly inhibited in the first 30 sec of reaction, then gradually stimulated afterwards. The initial rate of the reaction would not truly reflect the level of $PLA_2$-i activity. A total of 12 data points across the 2 min reaction period reflect the enzymatic activity more accurately than the initial rate.

The method of the present invention can be used to identify agents that can alter the activity of a phospholipase. In this case, the activity of a phospholipase is measured in the absence and presence of a test agent and the effect of the agent on the activity of the phospholipase can be determined.

In another aspect, the present invention relates to a kit for measuring the activity of a phospholipase. The kit will contain a liposome of the present invention and a phospholipase.

When the phospholipase is $PLA_2$, the kit may further contain a calcium source.

B. Measuring $PLA_2$ Activity

In one embodiment, the method of present invention for measuring the activity of a phospholipase is used to measure the activity of a $PLA_2$. Examples of $PLA_2$s whose activity can be measured include but are not limited to $PLA_2$-IIA, pancreatic $PLA_2$ and bee venom $PLA_2$.

As an example to practice the method of the present invention, a liposome of the present invention is mixed with a $PLA_2$ reaction buffer to form a pre-reaction mixture. The $PLA_2$ reaction buffer can support the reaction catalyzed by the $PLA_2$. The fluorescence intensity of the pre-reaction mixture is recorded after which the $PLA_2$ is added into the pre-reaction mixture to form a reaction mixture. The fluorescence intensity of the reaction mixture is then measured and the $PLA_2$ activity can be determined by comparing the fluorescence intensity of the reaction mixture and the fluorescence intensity of the pre-reaction mixture.

A skilled artisan is familiar with the buffer systems that can support the reactions catalyzed by a phospholipase such as a $PLA_2$. Examples of buffer systems that can be used include but are not limited to Tris-HCl, phosphate, acetate, citrate and glycine. The pH value of a buffer system can range from about 2 to about 10, preferably from about 6 to about 10, and most preferably about 7.4. In the case of the Tris-HCl system, the Tris-HCl concentration can range from about 0.001 M to about 1.0 M, preferably from about 0.005 M to about 0.2 M, and most preferably about 0.01 M. When the activity of a calcium-dependent $PLA_2$ is measured, a calcium source is also added into the buffer system. Examples of calcium sources that are useful in the present invention include but are not limited to $CaCl_2$, calcium fluoride and calcium carbonate. The $Ca^{2+}$ concentration in the buffer system can be from 0 to about 1.0 M, preferably from about 0.0001 M to about 0.1 M, and most preferably about 0.01 M. It is noted that other metals such as magnesium can replace calcium for the purpose of measuring the $PLA_2$ activity.

When the method of the present invention is used to measure the activity of $PLA_2$ in a complex composition such as a biological sample, certain factors (e.g., proteins) in the composition may cause a relatively substantial increase in fluorescence intensity to mask any increase caused by the $PLA_2$ contained therein. This problem may be solved by including a $PLA_2$ stimulator such as α1-AT in the reaction. Since the $PLA_2$ stimulator can only further increase the increase of fluorescence intensity caused by $PLA_2$ but not other factors, the difference between the fluorescence increase in the presence and absence of the stimulator correlates with the $PLA_2$ activity. Examples of biological samples whose $PLA_2$ activity can be measured as such include but are not limited to plasma, serum, BALF, sputum, urine, synovial fluid, amniotic fluid, peritoneal fluid, cerebrospinal fluid, pleural fluid, pericardial fluid, white blood cells, and alveolar macrophages. It should be noted that the suitable temperature at which the $PLA_2$ activity in a biological sample is measured may be different from that for measuring the $PLA_2$ activity in a substantially pure source. The suitable temperature can be readily determined by a skilled artisan. An example of measuring the $PLA_2$ activity in the plasma of CF and COPD patients and in the synovial fluid of arthritis patients are described in Example 3. Since BALF rather than a substantially pure source of $PLA_2$ stimulator α1-AT was used in the studies presented in Example 3, the BALF was boiled at 100° C. for 5 min in advance to inactivate the components that may interfere with the assay.

Conventionally, $PLA_2$ activity is measured by methods that involve the use of radioactive materials, which are inconvenient, time-consuming and biohazardous. A fluorescent liposome-based method has been described but the method is of low sensitivity in comparison to the radioactive methods (49). Another available fluorescence method involves incorporation of fluorescent bis-BODIPY FL $C_{11}$-PC into the cellular membrane and it can only measure the $PLA_2$ activity indirectly (51). Other prior art methods include the pH titration method and the monolayer method, both of which require bulk volumes of reaction solutions, substrates and enzymes.

In comparison to the above prior art methods, the method of the present invention is advantageous in that it is simple, sensitive and involves no hazardous materials. Further, the method of the present invention allows continuous recordation of fluorescent intensity making the result more reliable. In addition, the method of the present invention can be readily applied to multi-well plates and thus adapted to high throughput applications.

C. Measuring $PLA_2$-s and $PLA_2$-i Activity.

In another aspect, the present invention relates to a method for measuring the activity of a $PLA_2$-s or $PLA_2$-i. The method involves running the assay described in Part IA with $PLA_2$ in the presence and absence of a stimulator or inhibitor. The difference in $PLA_2$ activity as measured in the presence and absence of the stimulator or inhibitor reflects the activity of the stimulator or inhibitor.

In one embodiment, the $PLA_2$-s or $PLA_2$-i activity of a biological sample is measured. Suitable biological samples whose $PLA_2$-s or $PLA_2$-i activity can be measured include but are not limited to plasma, serum, BALF, sputum, urine, synovial fluid, amniotic fluid, peritoneal fluid, cerebrospinal fluid, pleural fluid, pericardial fluid, white blood cells, and alveolar macrophages. As shown in the examples below, the volume of a biological sample can dictate whether a stimulator or inhibitor activity is measured. When both stimulator and inhibitor activities are present in the sample, the volume suitable for measuring the inhibitor activity is typically larger than that suitable for measuring the stimulator activity. In addition, the amount of exogenous $PLA_2$ used in the assay also affects the appropriate volumes for measuring the stimulator or inhibitor activity. For example, the $PLA_2$-s and $PLA_2$-i assays conducted in Example 3 employed less $PLA_2$ than Example 1, the volumes of the biological samples for measuring the stimulator or inhibitor activity were also less in Example 3. Specific assay conditions with regard to sample volume can be readily determined by a skilled artisan.

As shown in Example 2 below, the $PLA_2$-s activity in the CF BALF only stimulated the activity of monomeric $PLA_2$s (e.g., $PLA_2$-IIA, pancreatic $PLA_2$ and bee venom $PLA_2$) but not that of a dimeric $PLA_2$ (e.g., snake venom $PLA_2$). This is consistent with the fact that most $PLA_2$s, especially those involved in inflammation conditions, are monomers. The $PLA_2$-s activity in the BALF is that of a truncated α1-AT. Thus, when the assay is used to measure the $PLA_2$-s activity of a biological sample that contains α1-AT, a monomeric $PLA_2$ should be used.

D. Determining Whether a Subject has an Abnormally High $PLA_2$ Activity.

In another aspect, the present invention relates to a method for determining whether a human or non-human animal subject has an abnormally high $PLA_2$ activity. As described in Part IB, a biological sample obtained from a human or nonhuman subject may contain certain factors that can make the detection of $PLA_2$ activity contained therein difficult. Part IB offers one solution to the problem by including a $PLA_2$ stimulator in the $PLA_2$ assay. Therefore, in one embodiment of the method, the $PLA_2$ activity in a biological sample from the human or non-human subject is measured in the presence of a $PLA_2$ stimulator and the activity is then compared to a normal range established by using the same method and the same type of biological sample obtained from healthy subjects of the same species. A higher than normal range value indicates that the subject has an abnormally high $PLA_2$ activity.

Another solution to the problem is to use the $PLA_2$ stimulator and/or inhibitor activities in a biological sample as indicators of the $PLA_2$ activity therein. In healthy human and non-human animals, $PLA_2$ stimulators and inhibitors work together to keep $PLA_2$ activity in check and hence the production of lipid mediators in balance. Under pathological conditions, a decrease in $PLA_2$-i activity and/or an increase in $PLA_2$-s activity will lead to an increase in $PLA_2$ activity, which stimulates the production of lipid mediators. Therefore, $PLA_2$ stimulator and/or inhibitor activities can be used as indicators for the $PLA_2$ activity. Thus, in another embodiment of the method for determining whether a human or non-human animal subject has an abnormally high $PLA_2$ activity, the $PLA_2$-s activity, the $PLA_2$-i activity or the relative activity of $PLA_2$-s and $PLA_2$-i (e.g., the $PLA_2$-i/$PLA_2$-s activity ratio and the $PLA_2$-s/$PLA_2$-i activity ratio) in a sample obtained from the subject is determined using the method described in Part IC. The activity is then compared to a normal range established by using samples obtained from healthy subjects of the same species. If the particular subject has a lower than normal $PLA_2$-i activity or $PLA_2$-i to $PLA_2$-s relative activity, or a higher than normal $PLA_2$-s activity or $PLA_2$-s to $PLA_2$-i relative activity, the subject is determined to have an abnormally high $PLA_2$ activity. As shown in the examples below, a higher relative activity of $PLA_2$-s to $PLA_2$-i can mean a lower absolute value of a negative $PLA_2$-i/$PLA_2$-s activity ratio, a higher absolute value of a negative $PLA_2$-s/$PLA_2$-i activity ratio, or a positive $PLA_2$-i/$PLA_2$-s or $PLA_2$-s/$PLA_2$-i activity ratio.

An abnormally high $PLA_2$ activity is associated with many disorders such as bacterial infection, viral infection, inflammation, CF, allergy, arthritis, sepsis, brain injury, cancer and cardiovascular disorders. The method of the present invention can help identifying individuals with such disorders and implementing appropriate treatment and symptom relief strategies.

While a plasma or serum sample is suitable in the method of the present invention to determine whether a human or non-human subject has a high $PLA_2$ activity in general, analysis of a more specific sample may be required depending on the particular disorder in question. For example, for lung inflammation, an analysis of the $PLA_2$-s and $PLA_2$-i activities in BALF is preferred. As another example, for rheumatic arthritis, an analysis of the synovial fluid may be necessary. Other examples of biological samples that can be used in the method of the present invention include but are not limited to sputum, urine, amniotic fluid, peritoneal fluid, cerebrospinal fluid, pleural fluid, pericardial fluid, white blood cells, and alveolar macrophages. A skilled artisan can readily determine which samples are suitable for a particular disorder of interest.

E. Measuring the Activity of a Lipase

As demonstrated in Example 3 below, the fluorescent method of the present invention can be used to measure the activity of a lipase. To do so, a liposome of the present invention in which the fluorescently labeled molecule contains a fluorescently labeled fatty acid moiety is brought into contact with PLC so that diacylglycerol is produced, which leads to a decrease in fluorescence intensity. Next, a phospholipase is added to hydrolize diacylglycerol leading to the release of fluorescent-labeled fatty acids and hence an increase in fluorescence intensity. Thus, measuring the fuorescence intensity change allows the determination of the lipase activity.

II. $PLA_2$ Stimulator and Inhibitor

A. α1-AT and Mercaptalbumin as $PLA_2$ Stimulator and Inhibitor

The inventors have identified the full length α1-AT and the truncated α1-AT from 16His to 357Pro (amino acids 16 to 357 of SEQ ID NO:1) as $PLA_2$ stimulators. It is expected that any truncated form of α1-AT that retains at least the part of 16His to 357Pro has $PLA_2$ stimulatory activity. The inventors further identified mercaptalbumin as a $PLA_2$ inhibitor when present at a sufficiently high level. The exact amount of mercaptalbumin needed to display the inhibitory activity may vary depending on conditions of a specific application but can be readily determined by a skilled artisan.

α1-AT as a stimulator is only effective for monomeric $PLA_2$s (e.g., $PLA_2$-IIA, pancreatic $PLA_2$ or bee venom $PLA_2$) but not dimeric $PLA_2$s (e.g., snake venom $PLA_2$, see Example 2 below).

Although the identification of the $PLA_2$ stimulators and inhibitor were made with human samples and proteins, it is expected that human α1-AT (including truncated forms) and mercaptalbumin homologues in other species (e.g., other animal species) also have $PLA_2$ stimulatory and inhibitory activities. It is noted that α1-AT amino acid sequences in other species may differ from the human sequence. A skilled artisan can use an alignment program to identify the amino acids in those sequences that correspond to the 16His and 357Pro of the human sequence. In addition, one skilled in the art of molecular biology would appreciate that minor deletions, additions and mutations may not change the attributes of a $PLA_2$ stimulator and inhibitor. To determine whether or not a modified sequence will retain the essential stimulatory or inhibitory functions, one only need to produce the modified sequence and test it using one of the assays described in the present invention.

The $PLA_2$ stimulatory activity of α1-AT is resistant to heat inactivation while the $PLA_2$ stimulatory activity of albumin and the $PLA_2$ inhibitory activity of mercaptalbumin are sensitive to heat inactivation. For example, boiling at 100° C. for 5 min can destroy the stimulatory and inhibitory activities of albumin and mercaptalbumin. However, the stimulatory activity of α1-AT remained intact under the same conditions. Although determining the $PLA_2$ stimulatory activity of α1-AT in a biological sample such as plasma and serum is desirable under many circumstances, it proved to be difficult with the fluorescent method because the stimulatory activity of α1-AT is masked by that of the more abundant albumin (e.g., the albumin concentration (4.0 g/dL) is 20 times higher than the α1-AT concentration (0.2 g/dL) in human plasma). Heat inactivation of such a sample can destroy the activities from albumin and allow the activity of α1-AT to be successfully measured. Heat inactivation has the additional benefit of destroying other factors in a sample that may potentially interfere with the detection of the stimulatory activity of α1-AT. Therefore, even for a biological sample such as BALF that may or may not contain a significant amount of albumin, heat inactivation is still preferred. Boiling at 100° C. for 5 min is a suitable heat inactivation condition. Other suitable conditions can be readily determined by a skilled artisan.

In CF patients, neutrophil elastase (NE) is believed to play a major role in the damage of airway cells and supporting tissues, which lead to bronchiectasis and bronchial obstruction. α1-AT is the most potent endogenous inhibitor of NE. In CF patients, the amount of α1-AT in the serum is typically about two-times higher than the normal level and the protein was fully active against NE (50). However, α1-AT is largely broken down and useless for inhibiting NE in bronchial tubes of the inflamed CF lung. Treating CF patients with α1-AT via aerosol inhalation has not clearly provided any benefit. The finding disclosed here that α1-AT can stimulate the activity of $PLA_2$ may provide an explanation as to why the treatment is not effective and suggests a different treatment strategy for these patients, i.e., to inhibit the $PLA_2$ stimulatory activity of truncated α1-AT.

B. Applications of α1-AT and Mercaptalbumin

In one aspect, the present invention relates to a method for increasing the activity of a monomeric $PLA_2$ by exposing $PLA_2$ to a polypeptide that contains α1-AT in an amount sufficient to increase the activity of $PLA_2$.

In another aspect, the present invention relates to a method for inhibiting the activity of $PLA_2$ by exposing $PLA_2$ to a polypeptide that contains mercaptalbumin in an amount sufficient to inhibit the activity of $PLA_2$.

In another aspect, the present invention relates to a method of inhibiting the activity of a monomeric $PLA_2$ stimulated by α1-AT by inhibiting the $PLA_2$ stimulating activity of α1-AT sufficient to lower the stimulated $PLA_2$ activity.

In another aspect, the present invention relates to a method of increasing the activity of $PLA_2$ inhibited by mercaptalbumin by inhibiting the $PLA_2$ inhibitory activity of mercaptalbumin to increase the inhibited $PLA_2$ activity.

There are many ways that the $PLA_2$ stimulatory activity of α1-AT or the $PLA_2$ inhibitory activity of mercaptalbumin can be inhibited and a skilled artisan is familiar with these ways. For example, antibodies against α1-AT or mercaptalbumin can be made and used to inhibit their activities. Other agents that can inhibit the $PLA_2$ stimulatory activity of α1-AT or the $PLA_2$ inhibitory activity of mercaptalbumin can be identified by the method below.

In another aspect, the present invention relates to a method of identifying an agent that can alter the $PLA_2$ stimulatory activity of α1-AT or the $PLA_2$ inhibitory activity of mercaptalbumin. The method involves exposing a composition containing $PLA_2$ and α1-AT or mercaptalbumin to a test agent, measuring the $PLA_2$ activity of the composition in the presence of the test agent, and comparing the $PLA_2$ activity to that of a control composition that is not exposed to the test agent. If a difference is observed, the test agent should be further tested to eliminate the possibility that it altered the $PLA_2$ activity directly. In the method, α1-AT and mercaptalbumin can be provided in a biological sample. However, one needs to heat inactivate the biological sample when used in identifying agents for altering the stimulatory activity of α1-AT if the sample contains substantial amount of albumin. In addition, a monomeric $PLA_2$ should be used in the method for identifying agents that can alter the stimulatory activity of α1-AT since α1-AT only inhibits the activity of monomeric $PLA_2$s.

One source of agents that can be screened is various chemical libraries including peptide libraries. Examples of such libraries include those from ASINEX (i.e. the Combined Wisdom Library of 24,000 manually synthesized organic molecules) and from CHEMBRIDGE CORPORATION (i.e. the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds) and linear library, multimeric library and cyclic library (Tecnogen (Italy)). Once an agent with desired activity is identified, a library of derivatives of that agent can be screened for better agents.

In another embodiment, the present invention relates to a method of determining whether a human or non-human subject has an abnormally high $PLA_2$ activity. The method involves determining the amount of α1-AT, mercaptalbumin or both in an appropriate biological sample prepared from the subject. Then, the amount of α1-AT, the amount of mercaptalbumin or the relative amount of α1-AT and mercaptalbumin is compared to a normal range established form the same type of sample obtained from healthy subjects of the same species. A higher than normal level or relative level of α1-AT, or a lower than normal level or relative level of mercaptalbumin would indicate that the subject has an abnormally high $PLA_2$ activity.

An abnormally high $PLA_2$ activity is associated with many disorders such as bacterial infection, viral infection, inflammation, CF, allergy, arthritis, sepsis, brain injury, cancer and cardiovascular disorders. The method of the present invention can help identifying individuals with such disorders and implementing appropriate treatment and symptom relief strategies.

While a plasma or serum sample is suitable in the method of the present invention to determine whether a human or non-human subject has a high $PLA_2$ activity in general, analysis of a more specific sample may be required depending on the particular disorder in question. For example, for lung inflammation, an analysis of the $PLA_2$-s and PLA2-i activities in BALF is preferred. As another example, for rheumatic arthritis, an analysis of the synovial fluid may be necessary. Other examples of biological samples that can be used in the method of the present invention include but are not limited to sputum, urine, amniotic fluid, peritoneal fluid, cerebrospinal fluid, pleural fluid, pericardial fluid, white blood cells, and alveolar macrophages. A skilled artisan can readily determine which samples are suitable for a particular disorder of interest.

In another embodiment, the present invention relates to a method of determining whether a human or non-human subject has lung inflammation caused by CF. The method involves determining the presence of a truncated α1-AT in bronchial tubes, BALF or sputum of the subject.

In another embodiment, the present invention relates to a method of treating a disorder associated with an abnormally high level of $PLA_2$ in a human or non-human animal subject by inhibiting the $PLA_2$ stimulatory activity of α1-AT or increasing the $PLA_2$ inhibitory activity of mercaptalbumin. A skilled artisan is familiar with the ways that the stimulatory activity of α1-AT can be inhibited and the inhibitory activity of mercaptalbumin can be increased. For example, antibodies and other α1-AT blocking agents can be administered to the subject. Strategies directed at suppressing the expression of α1-AT (e.g., the anti-sense technology) can also be used. To increase the inhibitory activity of mercaptalbumin, a polypeptide containing mercaptalbumin can be administered into the subject directly or an expression vector encoding the polypeptide can be introduced into the subject and the expression thereof can then be induced. Alternatively, mercaptalbumin levels in the subject can be increased by strategies such as enhancing endogenous albumin expression and inhibiting albumin oxidization. Agents that can increase the inhibitory activity of mercaptalbumin can also be used.

III. PLC Inhibitor

As shown in Example 3 below, α1-AT can inhibit the activity of PLC. In one aspect, the present invention relates to a method of inhibiting the activity of PLC by exposing PLC to a polypeptide that contains α1-AT in an amount sufficient to inhibit PLC activity.

In another aspect, the present invention relates to a method of stimulating PLC activity by inhibiting the PLC inhibitory activity of α1-AT sufficiently to stimulate the inhibited PLC activity. There are many ways that the PLC inhibiting activity of α1-AT can be inhibited and these ways have been described in connection with inhibiting the $PLA_2$ inhibitory activity of α1-AT.

In another aspect, the present invention relates to a method for identifying an agent that can alter the PLC inhibitory activity of α1-AT. The method involves exposing a composition containing PLC and α1-AT to a test agent, measuring the PLC activity of the composition in the presence of the test agent, and comparing the PLC activity to that of a control composition that is not exposed to the test agent. If a difference is observed, the test agent should be further tested to eliminate the possibility that the test agent altered the PLC activity directly. Examples of sources of agents that can be screened are described in connection with a similar method for $PLA_2$ inhibitory activity of α1-AT.

The invention will be more fully understood upon consideration of the following non-limiting examples.

EXAMPLE 1

Materials and Methods

Bronchoalveolar lavage fluid: Bronchoalveolar lavage fluids were obtained from normal volunteers and patients with CF as described previously (52). The fluid was filtered through two layers of a sterile gauze into a 50 ml tube, then centrifuged at 1,200 rpm for 10 min at 4° C. using a Beckman Model TJ-6 centrifuge. The cell-free BALF was stored at −70° C. before use. The cell pellets were washed with about 35 ml incomplete Hanks balanced salt solution (HBSS) and spun at 1,000 rpm at 4° C. for 10 min. The pellets were suspended in 1-2 ml HBSS. Total and viable cells were counted by mixing an aliquot of cell suspension and trypan blue solution using a hemacytometer. An amount of 15,000 to 20,000 cells was taken for each cytospin slide preparation for morphological analyses using Diff-Quik Stain Set (Dade Behring AG, Dudingen, Switzerland). The rest of the cell suspension was spun at 1,000 rpm and the supernatant was discarded. The pellets were suspended in HBSS buffer; approximately $5 \times 10^6$ cells were homogenized in 100 μl buffer containing 2 mM phenylmethylsulfonyl fluoride (PMSF) and 1 mM EDTA and sonicated for 30 sec two times on ice using a Virsonic cell disrupter. The cell homogenate was centrifuged at 10,000 rpm for 1 min; the supernatant was saved and stored at −70° C. before use and the pellet was discarded.

A portion of the BAL cell free fluid was concentrated 50-fold to less than 0.2 ml using an Amicon microconcentrator-10 (membrane cut-off molecular weight 10,000) as described previously (52). The condensed BALF was stored at −70° C. before use. The protein content in each sample was determined by the method of Lowry modified for 96-well plate analysis.

Sputum: Sputum is induced by inhalation of a 3% saline mist generated from an ultrasonic nebulizer. Wearing noseclips, subjects inhale the saline mist with tidal breaths and with an inspiration of total lung capacity once every minute. Every 4 min subjects are instructed to blow their noses and rinse their mouse with water before expectoration to minimize nasal contamination of the sample. This procedure continues for 12-24 min until an adequate volume of sputum is produced. Sputum is stored in a sterile container on ice and processed immediately (within 1 hour).

Sputum is transferred to a 50 ml conical polypropylene tube and its weight is determined. The sputum sample is mixed with 10% Sputolysin (Calbiochem, Biosciences, Inc., Lo Jolla, Calif.) and the mixture is incubated at 37° C. in a shaking incubator for 15 min. The solution is centrifuged at 2,000 rpm at 20° C. for 5 min. The supernatant and cells in the pellet are separated for further analysis.

Isolation of neutrophils, mononuclear leukocytes and plasma from peripheral blood: Blood was collected into a heparinized tube from a normal healthy subject or from subjects with CF or COPD. Neutrophils, mononuclear leukocytes and plasma were isolated using the neutrophil isolation media (NIM, Cardinal Associates, Santa Fe, N. Mex.) as described by the manufacturer's protocol. Cell differentiation and purity were analyzed by cytospin and morphological analysis using Diff-Quik Stain Set (Dade Behring AG, Dudingen, Switzerland). Cells were suspended in HBSS buffer containing 2 mM PMSF and 1 mM EDTA and sonicated for 30 sec two times on ice using a Virsonic cell disrupter. Approximately $5 \times 10^6$ cells were homogenized in 100 μl buffer. The cell homogenate was centrifuged at 10,000 rpm for 1 min; the supernatant was saved and stored at −70° C. before use and the pellet was discarded. The plasma was stored at −20° C. before use.

Preparation of $PLA_2$ and fluorescently labeled liposomes: Porcine pancreatic $PLA_2$ (EC3.1.1.4), $PLA_2$ from bee venom (*Apis mellifera*) and $PLA_2$ from snake venom (*Crotalus durissus terrificus*) were purchased from Sigma Chemical (St. Louis, Mo.). The working solution of $PLA_2$ was freshly prepared by diluting about 10 units of $PLA_2$ to 1 ml with 0.01 M Tris-HCl, pH 7.4 and kept at 4° C. prior to use. Dioleoyl phosphatidylcholine (DOPC) and phosphatidylglycerol (PG) were purchased from Sigma Chemical. Fluorescently-labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) was obtained from Molecular Probes (Eugene, Oreg.). Fluorescently-labeled unilamellar liposomes (UL) were used as substrate for in vitro measuring of $PLA_2$ activity, similar to that described previously for rapid screening of a $Ca^{2+}$-independent $PLA_2$ isolated from rat lung (49). In this study fluorescent liposomes were prepared as previously described (40) by mixing 2.04 μml DOPC, 2.04 μmol PG, and 0.018 μmol Bis-BODIPY FL $C_{11}$-PC in a molar ratio 10:10:0.14 in chloroform. After chloroform was evaporated to dryness under a stream of nitrogen, lipids were suspended in 1.5 ml sucrose/Tris buffer (0.25 M sucrose, 50 mM Tris-HCl, 0.02% sodium azide), pH 7.4. The suspension was stirred occasionally with vortex within 30 min. Then, the lipid suspension was sonicated 3 min on ice using a Virsonic cell disrupter (VirSonic, Gardiner, N.Y.). The liposomes were stored at 4° C. before use. Radioactively labeled liposomes were made of 2.04 μmol DOPC and 2.04 μmol PG in the presence of 1 μCi of L-α-[1-$^{14}$C]dioleoyl PC (NEN Du Pont, Wilmington, Del.) in 1.5 ml sucrose/Tris buffer as described (43).

Fluorescent assay of $PLA_2$: The $PLA_2$ assay was conducted in a cuvet in which 2.95 ml 0.01M Tris-HCl, pH 7.4, 30 μl of 1 M $CaCl_2$, and 10 μl of liposomes (27.3 nmol phospholipids) were each added. The solution was mixed well after the addition of each component. The fluorescence intensity of the solution was measured at room temperature using a Perkin-Elmer Luminescence Spectrometer LS50B equipped with FL WinLab software (Perkin-Elmer Instruments, Norwalk, Conn.) at 488 nm excitation (slit 2.5) and 530 nm emission (slit 5.0) to obtain the background reading. Then, an aliquot of $PLA_2$ (0.01-0.5 μg) working solution was added to the reaction mixture followed by rapid inversion of the cuvet three times (the final volume of the reaction mixture was 3 ml). Fluorescence intensity readings were immediately recorded every 10 sec for 2 min. In some tests, the fluorescence intensity of the reaction solution without the presence of $PLA_2$ was recorded for up to 2 min. To test $PLA_2$ activity in biological samples, an aliquot of sample solution was introduced to the reaction mixture prior to the addition of $PLA_2$ and the fluorescence intensity was determined for up to 2 min. Then, $PLA_2$ was added and fluorescence intensity was recorded as described above. Porcine pancreatic $PLA_2$ was routinely used in this and following studies unless otherwise specified.

Radioactive assay of $PLA_2$: In a 5 ml glass test tube, the $PLA_2$ reaction mixture contained 0.1 ml of 0.01 M Tris-HCl buffer (pH 7.4), 10 mM $CaCl_2$, 5 nmol $^{14}C$-labeled liposomes and 0.5 μg of pancreatic $PLA_2$. In some tests, 25-100 μg of CF BALF proteins, or 10 μg of rabbit lung annexin I or annexin VIII or both were added to the reaction mixture as specified. The reaction was carried out at room temperature for 30 sec and stopped by adding 2 ml of chloroform:methanol (1:2 vol) followed by addition of 0.4 ml water, and 10 μl of egg PC and lysoPC (20 nmol) which was used as carrier. The test tube was stirred using a Vortex. Lipids were extracted by adding additional 0.6 ml water and 0.6 ml chloroform. After agitating on a vortex, the mixture was centrifuged at 2,000 rpm for 10 min. The chloroform layer was withdrawn and transferred to a new test tube using a Pasteur pipette. Chloroform was evaporated to dryness under a flow of nitrogen. PC and lysoPC were isolated by the methods of silica gel thin-layer chromatography (TLC) using a developing solvent system of chloroform/methanol/water in a ratio of 65/45/5 as described previously (52). Lipids on the TLC plate were visualized by exposure of the TLC plate in an iodine tank. The PC, lysoPC and FA spots on the plate were scraped into a scintillation vial and a cocktail of scintillation fluid was added to the vial. Radioactivity in the vial was determined by using a beta scintillation counter. $PLA_2$ activity was expressed as either decrease in PC radioactivity or increase in fatty acid or lysoPC radioactivity as described previously (52).

Heat treatment of BALF and plasma: A portion of BALF or plasma was incubated in boiling water for 5 min followed by centrifugation at 10,000 rpm for 5 min. The supernatant was removed from the pellet. The pellet was suspended in the same volume of the supernatant and sonicated for 30 sec on ice. The protein content in both supernatant and pellet fractions were determined as described above. An aliquot of the supernatant or pellet was added to the $PLA_2$ reaction mixture as specified.

Results

Figure 2:
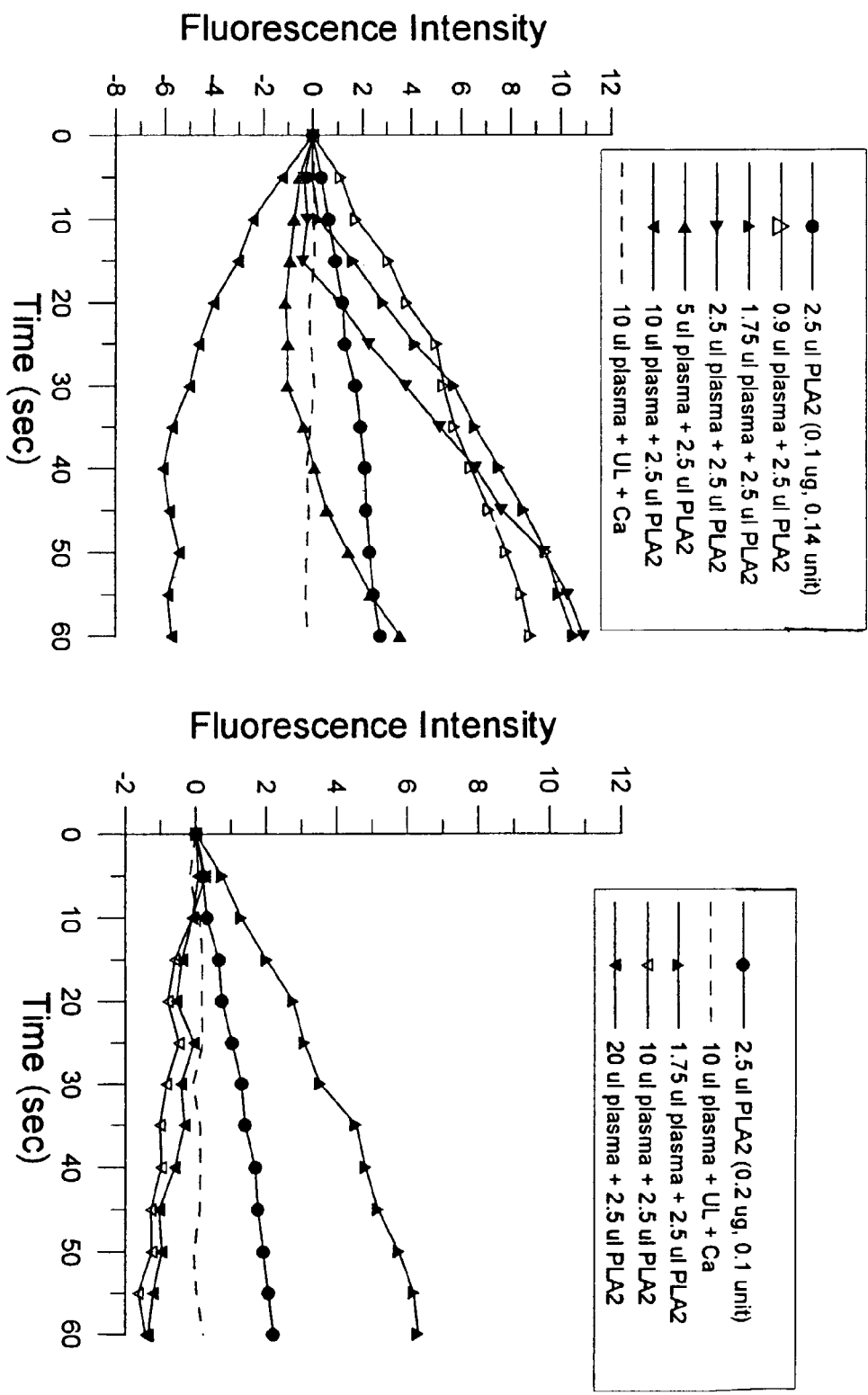
FIG. 2 shows the effects of human plasma on been venom $PLA_2$ and snake venom $PLA_2$.

Presence of $PLA_2$-s and $PLA_2$-i activities in human plasma: In the fluorescent assay an initial reading was recorded at zero time and then readings were recorded every 10 sec for 2 min. To present $PLA_2$ activity, the initial reading was subtracted from the subsequent readings and $PLA_2$ activity was expressed as fluorescence intensity vs. time (sec). The fluorescence intensity of the reaction mixture containing buffer, $CaCl_2$ and fluorescently-labeled liposomes remained relatively unchanged for up to 2 min (FIG. 1). Introduction of 0.1 μg of porcine pancreatic $PLA_2$ into the reaction mixture caused a linear increase in fluorescence intensity for up to 2 min. The presence of plasma collected from a normal, healthy subject (N1) (plasma 061301) increased the $PLA_2$ activity in a dose-dependent manner up to 4-6 μl of plasma (FIG. 1). Above 4-6 μl, the plasma exhibited an inhibitory property against $PLA_2$ activity and the $PLA_2$-stimulating activity, also in a dose dependent manner (FIG. 1). The plasma at 15 μl not only completely inhibited $PLA_2$ activity and the $PLA_2$-stimulating activity, it also reduced the fluorescence intensity of liposomes below the baseline values (FIG. 1). At 20 μl or larger volume, the plasma further reduced the fluorescence intensity to the lowest values. The intensity that was lower than the initial reading was in the negative range. These results show that plasma from a healthy person had $PLA_2$-stimulating activity (namely $PLA_2$ stimulator or $PLA_2$-s) and $PLA_2$ inhibitory activity (namely $PLA_2$ inhibitor or $PLA_2$-i). Whether $PLA_2$ activity is stimulated or inhibited by plasma in the in vitro reaction depends on the amounts of plasma present in the reaction mixture. In the absence of $PLA_2$ in the reaction mixture, plasma itself (e.g., 4 μl and 30 μl) had little effect on liposome fluorescence intensity (FIG. 1). Similarly, plasma stimulated and inhibited $PLA_2$ from bee venom (*Apis mellifera*) and to a lesser extent $PLA_2$ from snake venom (*Crotalus durissus terrificus*) (FIG. 2). It is noted that the volumes of plasma needed to show the optimal stimulating and inhibitory effects of $PLA_2$ from venom were less than that used in the pancreatic $PLA_2$ studies. This is because the sensitivity of the $PLA_2$ assay varies from batch to batch of the commercial products of $PLA_2$ and phospholipids. In the following studies, a plasma dose-dependent effect on $PLA_2$ was routinely performed for each batch of $PLA_2$ and liposomes to determine the volumes of plasma required to show optimal $PLA_2$-stimulating and -inhibitory activity.

Figure 3:
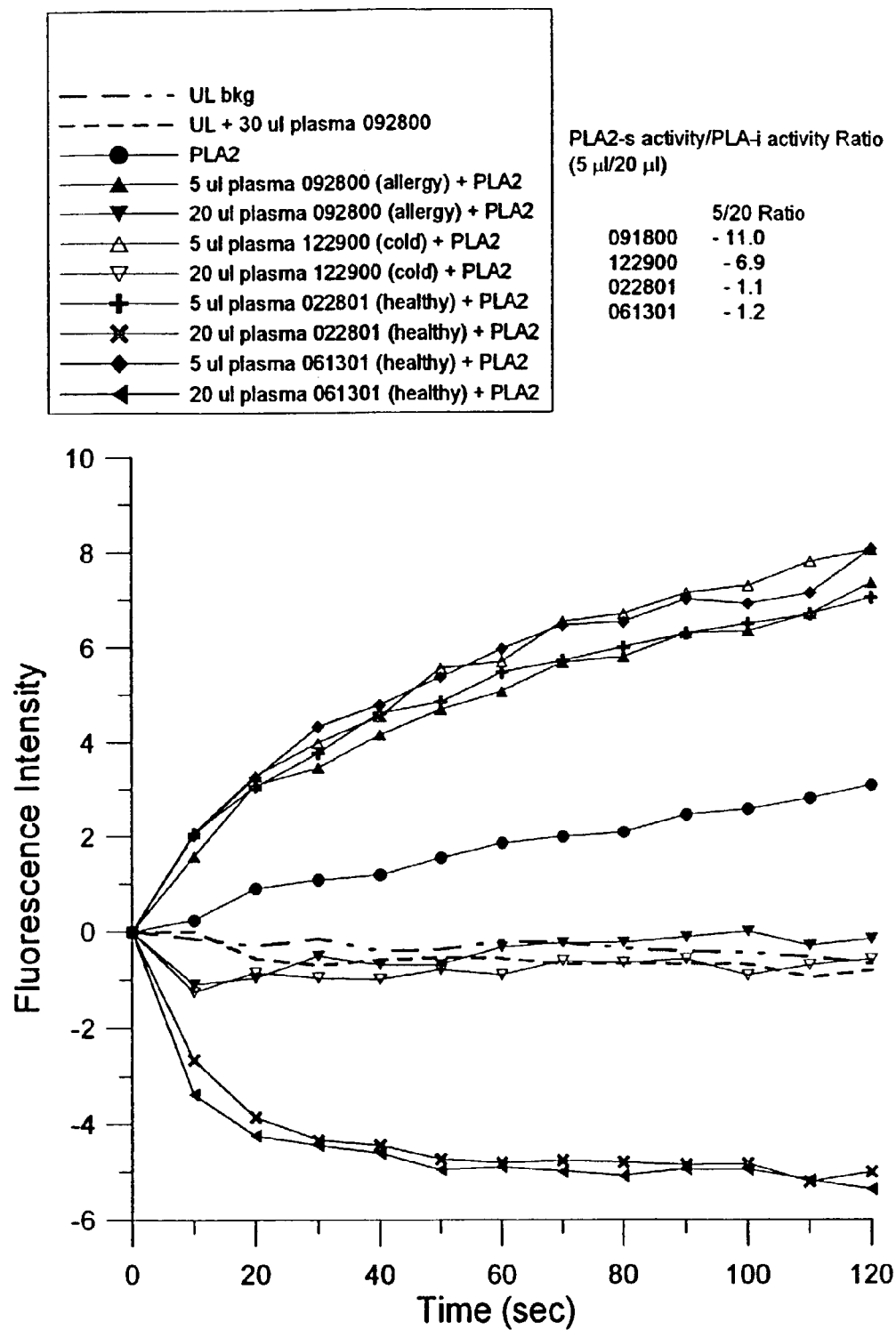
FIG. 3 compares the $PLA_2$-s and $PLA_2$-i activities in the plasma of a human subject when the subject was healthy and when the subject was suffering from allergy or cold.

Comparison of $PLA_2$-s and $PLA_2$-i activities in plasma from healthy subjects and subjects with inflamed lungs: Interestingly, two different plasma samples from subject N1, one collected when the subject had allergic rhinitis (plasma 092800) and the other one collected when the subject had a viral respiratory infection (plasma 122900), had distinct $PLA_2$-i activity as compared to that shown in FIG. 1. At 5 μl these plasma samples exhibited similar $PLA_2$-s activity (FIG. 3) as that shown in FIG. 1. However, at 20 μl these two plasma samples diminished $PLA_2$ and $PLA_2$-s activities only to the baseline values of liposomes (FIG. 3). Later, a plasma sample was collected when the subject was healthy (plasma 022801), and $PLA_2$-i activity was back to the level similar to that shown in FIG. 1 (FIG. 3).

Figure 4:
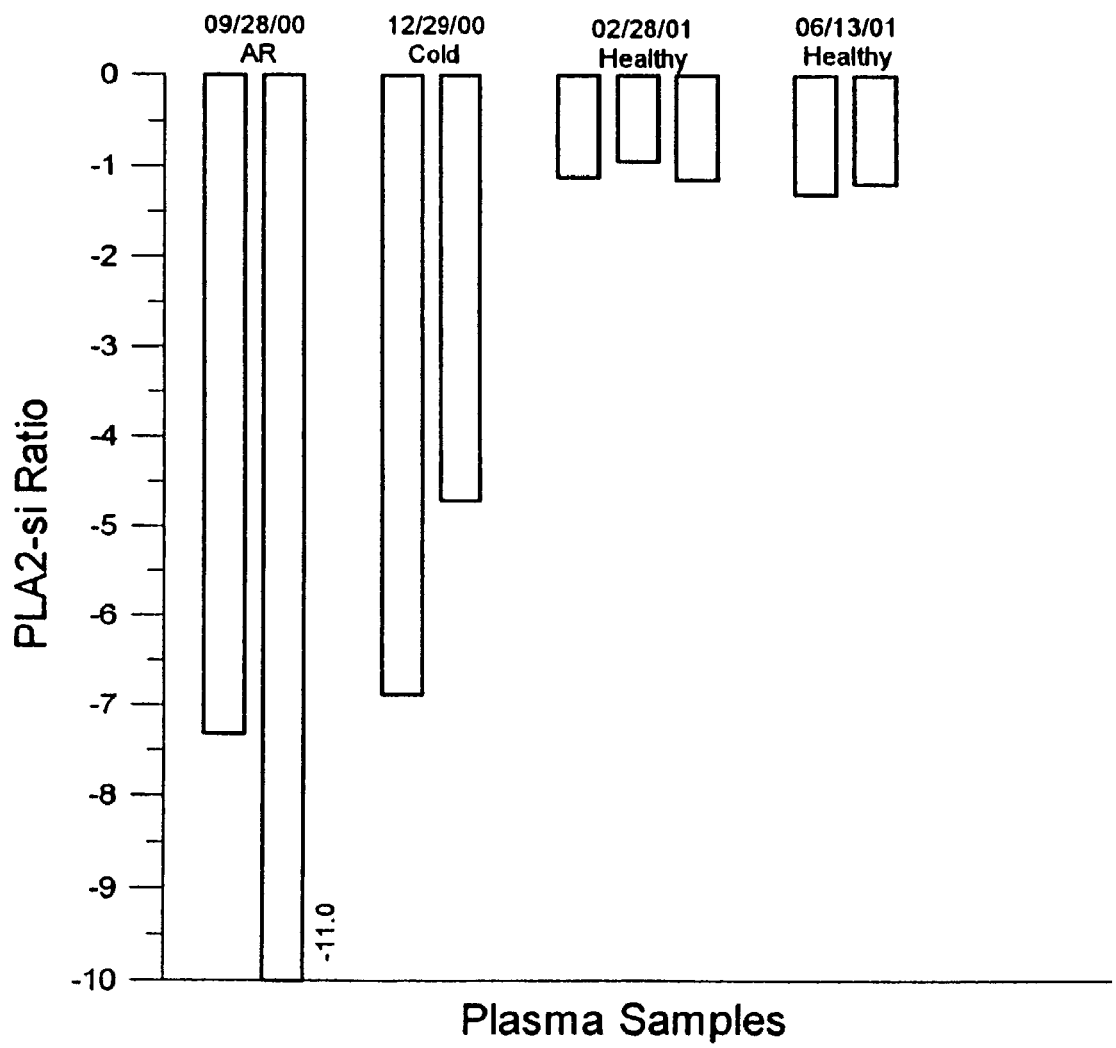
FIG. 4 compares the ratio of $PLA_2$-s to $PLA_2$-i in the plasma of a human subject when the subject was healthy and when the subject was suffering from allergy or cold.
Figure 5:
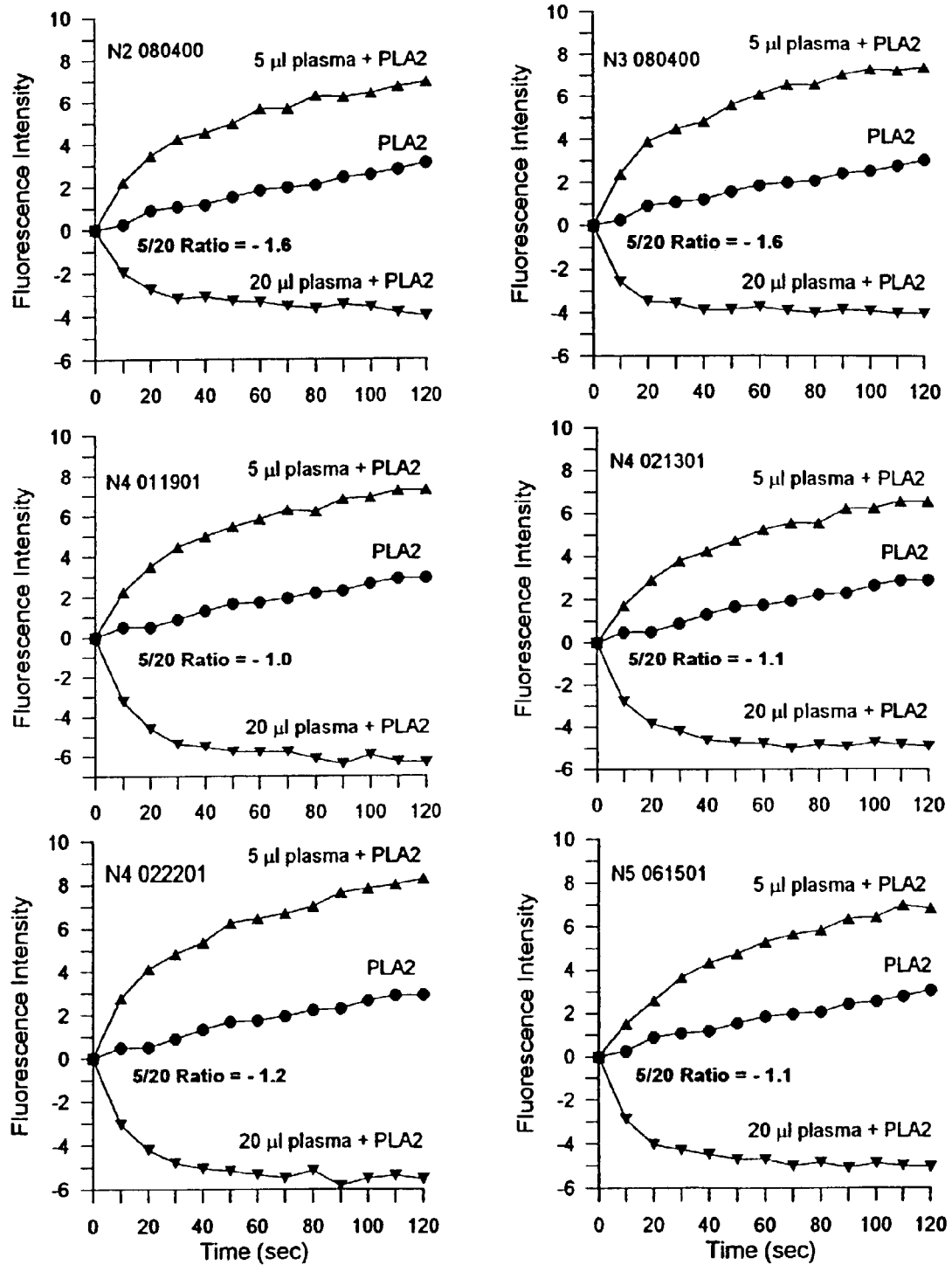
FIG. 5 shows that plasma obtained from four healthy human subjects had both $PLA_2$-s and $PLA_2$-i activities.
Figure 6:
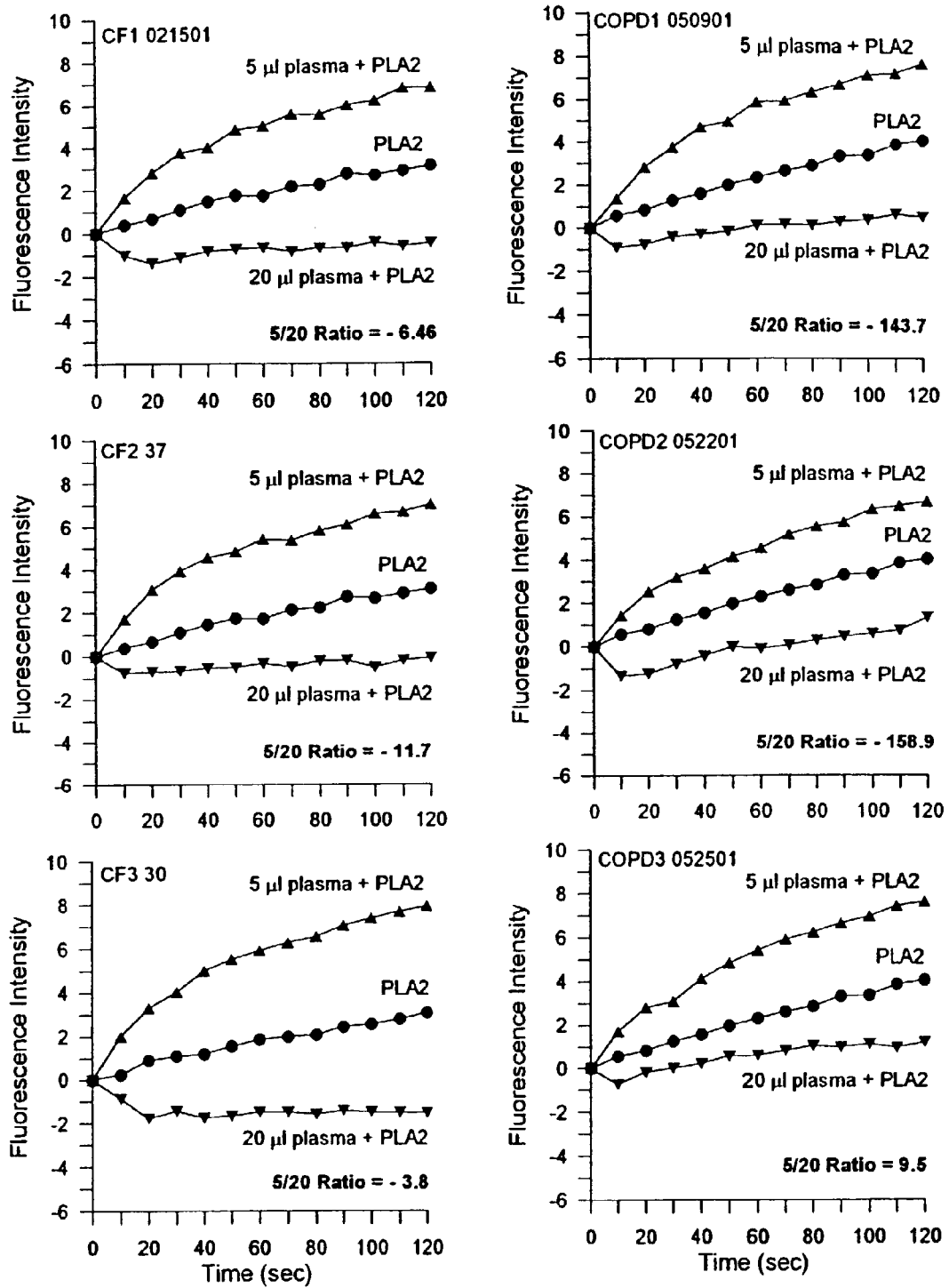
FIG. 6 shows that plasma obtained from four CF and COPD (Chronic Obstructive Pulmonary Disease) human subjects had only $PLA_2$-s activity.
Figure 7:
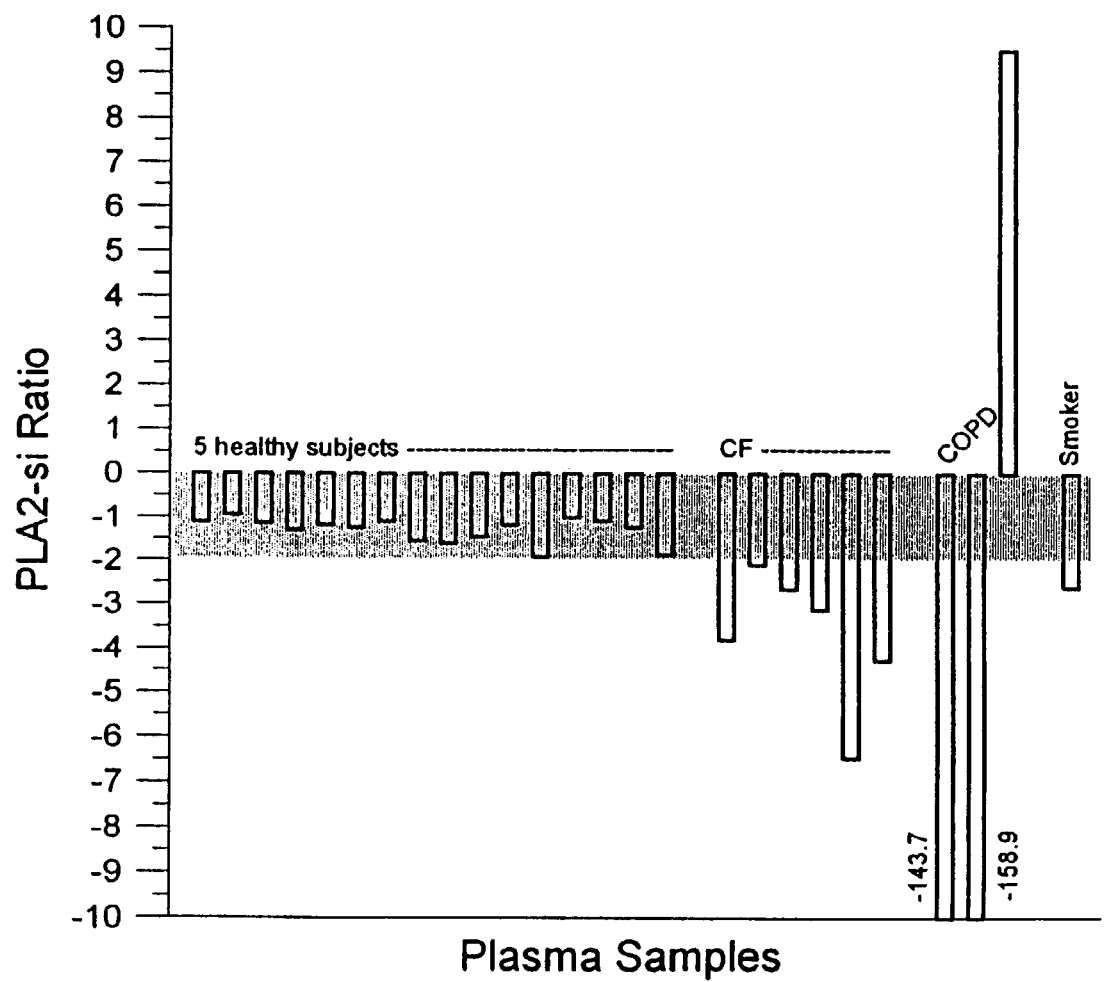
FIG. 7 shows the $PLA_2$-s to $PLA_2$-i ratios of plasma from healthy human subjects, human subjects with inflammation symptoms and a smoker.

A ratio of the $PLA_2$-s activity (5 μl plasma) over the $PLA_2$-i activity (20 μl plasma) was calculated from each total activity within 2 min period of reaction and named as "$PLA_2$-s/$PLA_2$-i ratio or $PLA_2$-si ratio". The $PLA_2$-si ratios of the four plasma samples of N1 subject were determined and each of the samples was assayed two to three times on different days. The ratios are summarized in FIG. 4. The absolute value of the negative ratio was less than 1.5 when blood was withdrawn when subject N1 was healthy (plasma 02/08/01 and plasma 06/13/01). However, the absolute value of the negative ratio was greater than 4 when blood was withdrawn when the subject had either allergy (plasma 09/28/00) or a viral respiratory infection (plasma 12/29/00). Negative ratio was obtained because of the negative value of total $PLA_2$-i activity. The higher the $PLA_2$-i activity, the lower the absolute value of the negative ratio. Several more plasma samples were obtained from four normal healthy subjects and the effects of these plasma samples on $PLA_2$ activity were tested; multiple plasma samples were obtained from one subject at different days. These plasma samples all exhibited PLA$_2$-s activity (5 μl plasma) and PLA$_2$-i activity (20 μl plasma) with a PLA$_2$-si ratio between −1.0 and −1.6 (FIG. 5). Contrarily, plasmas collected from three subjects with CF and three subjects with COPD all showed PLA$_2$-s activity, but these plasma samples all had PLA$_2$-i activity deficiency (FIG. 6). The PLA$_2$-si ratios of these samples ranged from −3.8 to −159 (the greater the absolute value of the negative ratio, the less PLA$_2$-i activity in the negative fluorescence intensity range). One COPD plasma sample had a ratio of +9.5, which means at 20 μl this sample had a total PLA$_2$-i activity in the positive range (i.e., greater PLA$_2$-i deficiency). The PLA$_2$-si ratios of plasma from healthy subjects, subjects with inflammation symptoms, and a smoker are summarized in FIG. 7. The cut-off point of the absolute values of the negative ratio for healthy subjects appears to be less than 2.0 (FIG. 7 light gray area). A negative ratio whose absolute value is greater than 2.0 or a positive ratio is likely associated with inflammation. It is interesting to note that a cigarette smoker, who appeared to be healthy, except for a chronic, intermittently productive cough, had a PLA$_2$-si ratio value of −2.6.

Figure 8:
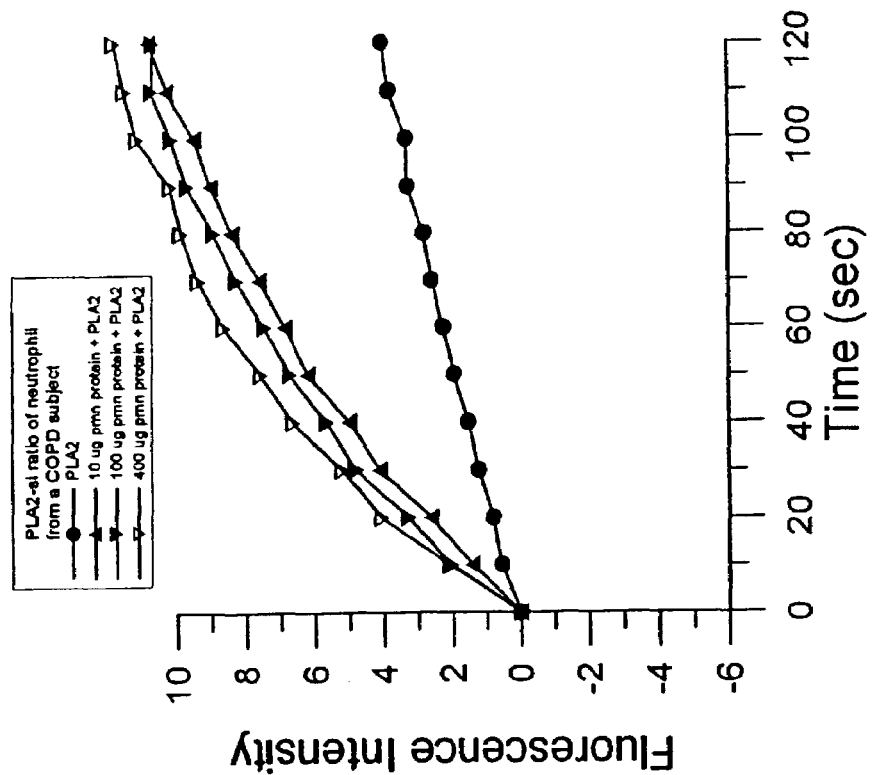
FIG. 8 shows $PLA_2$-s and $PLA_2$-i activities in neutrophils from a healthy subject and a COPD subject.
Figure 8:
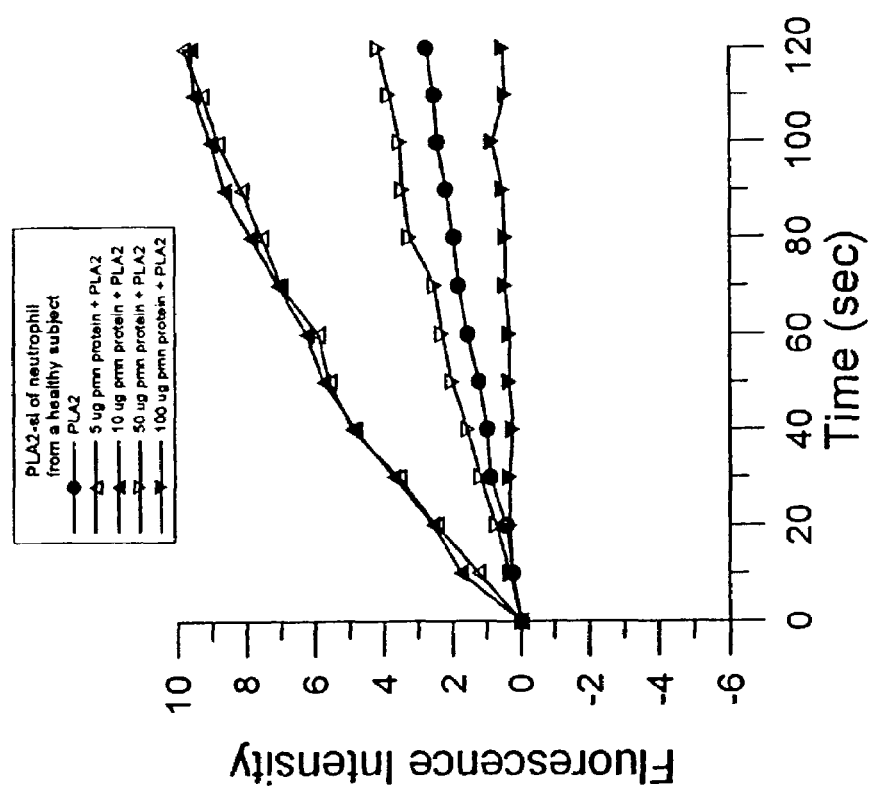

Distribution of PLA$_2$-s and PLA$_2$-i in blood and tissues: The patterns of PLA$_2$-s and PLA$_2$-i activities in the sera were similar to that observed in plasma. For example, the PLA$_2$-s/PLA2-i ratios of the sera from two healthy subjects were −1.2 and −0.6, whereas the ratios of the sera from two COPD subjects were −9.6 and −4.0. PLA$_2$-s and PLA$_2$-i activities were found in neutrophils, mononuclear leukocytes, and alveolar macrophages. An example of PLA$_2$-s and PLA$_2$-i activities in neutrophils from a healthy subject and a COPD subject is shown in FIG. 8. PLA$_2$-i deficiency was observed in neutrophils from a subject with COPD. In the presence of 0.1 mg neutrophil proteins from a healthy subject, PLA$_2$ and PLA$_2$-s activities were totally inhibited, whereas even in the presence of 0.4 mg proteins from a COPD subject's neutrophils, no PLA$_2$-i inhibitory activity was observed (FIG. 8). Similarly, PLA$_2$-i was deficient in mononuclear leukocytes and macrophages from subjects with inflamed lungs.

Figure 9:
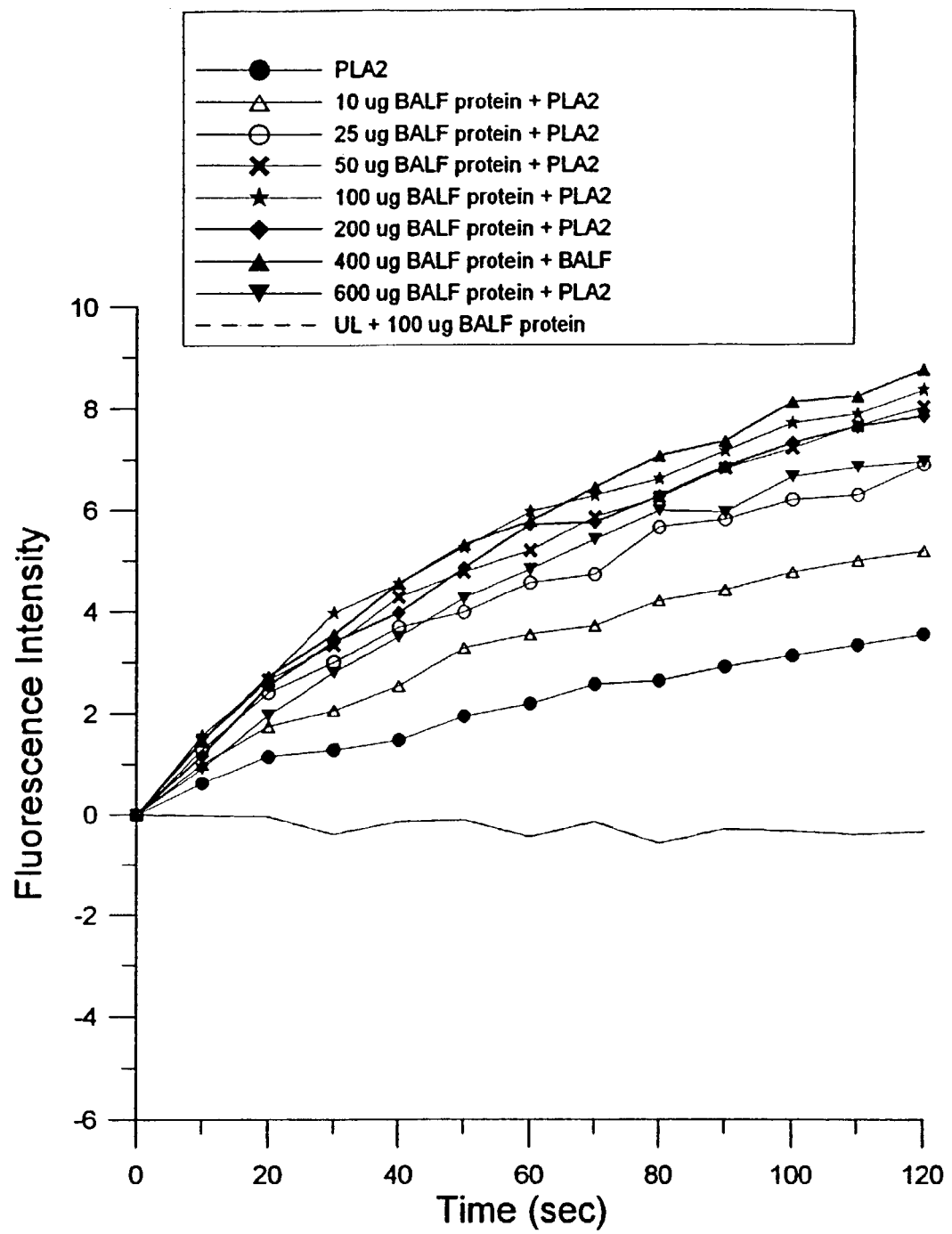
FIG. 9 shows $PLA_2$-s and $PLA_2$-i activities in BALF.
Figure 10:
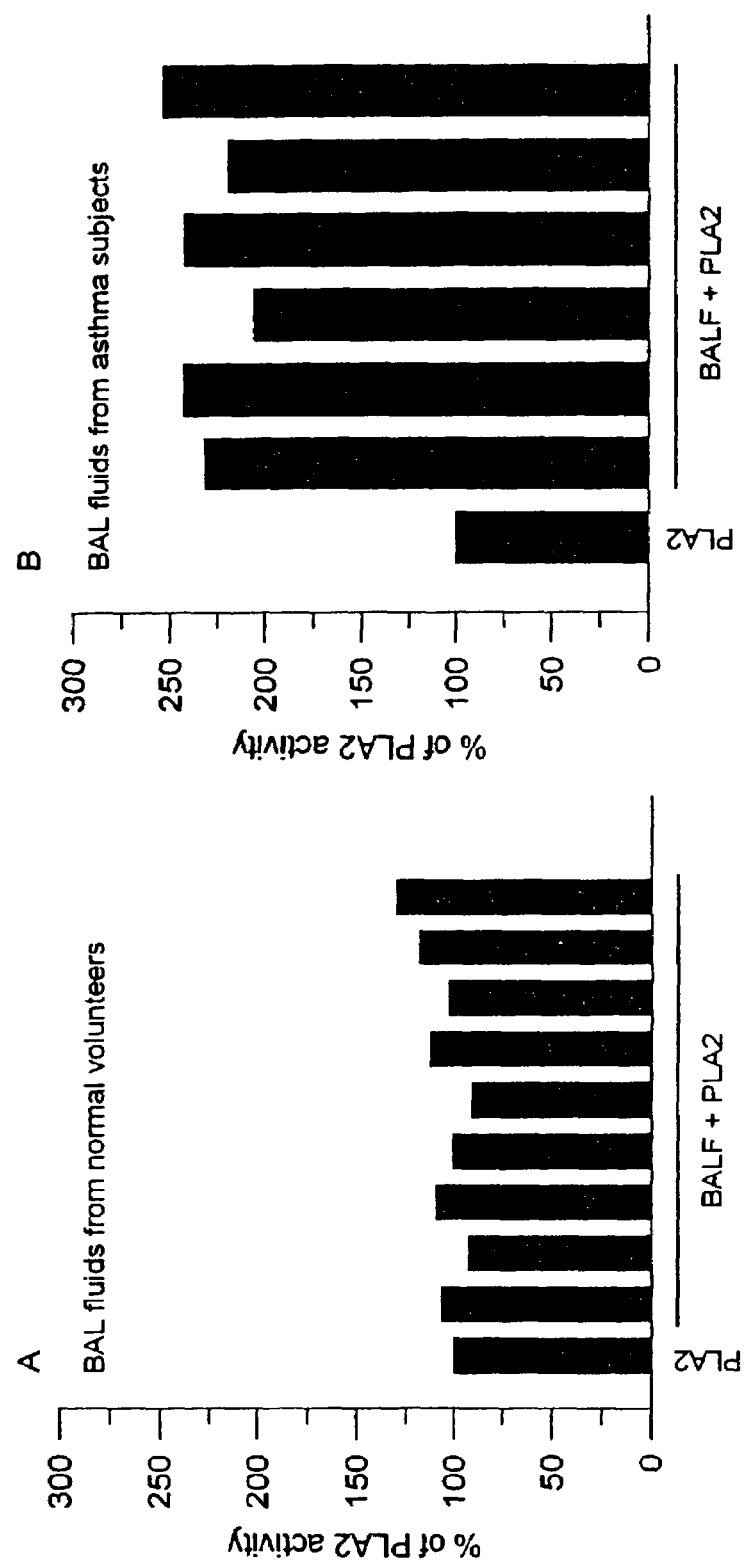
FIG. 10 shows the $PLA_2$-s activity of BALF from normal human subjects (A) and asthma human subjects (B).

PLA$_2$-s and PLA$_2$-i activities in BALF: BALF from a CF subject stimulated PLA$_2$ activity in a dose-dependent manner and the stimulation reached its optimum at 0.1 mg of BALF protein, indicating the presence of PLA$_2$-s in the fluid (FIG. 9). No PLA$_2$-i activity was detected in the BALF even up to 0.6 mg protein. Similar to the plasma, in the absence of PLA$_2$, BALF itself had no effect on liposome fluorescence intensity. BALFs from normal healthy individuals had little PLA$_2$-s activity under the same assay conditions (FIG. 10A). BALFs from subjects with allergic asthma stimulated PLA$_2$ activity by more than 2-fold (FIG. 10B).

Figure 11:
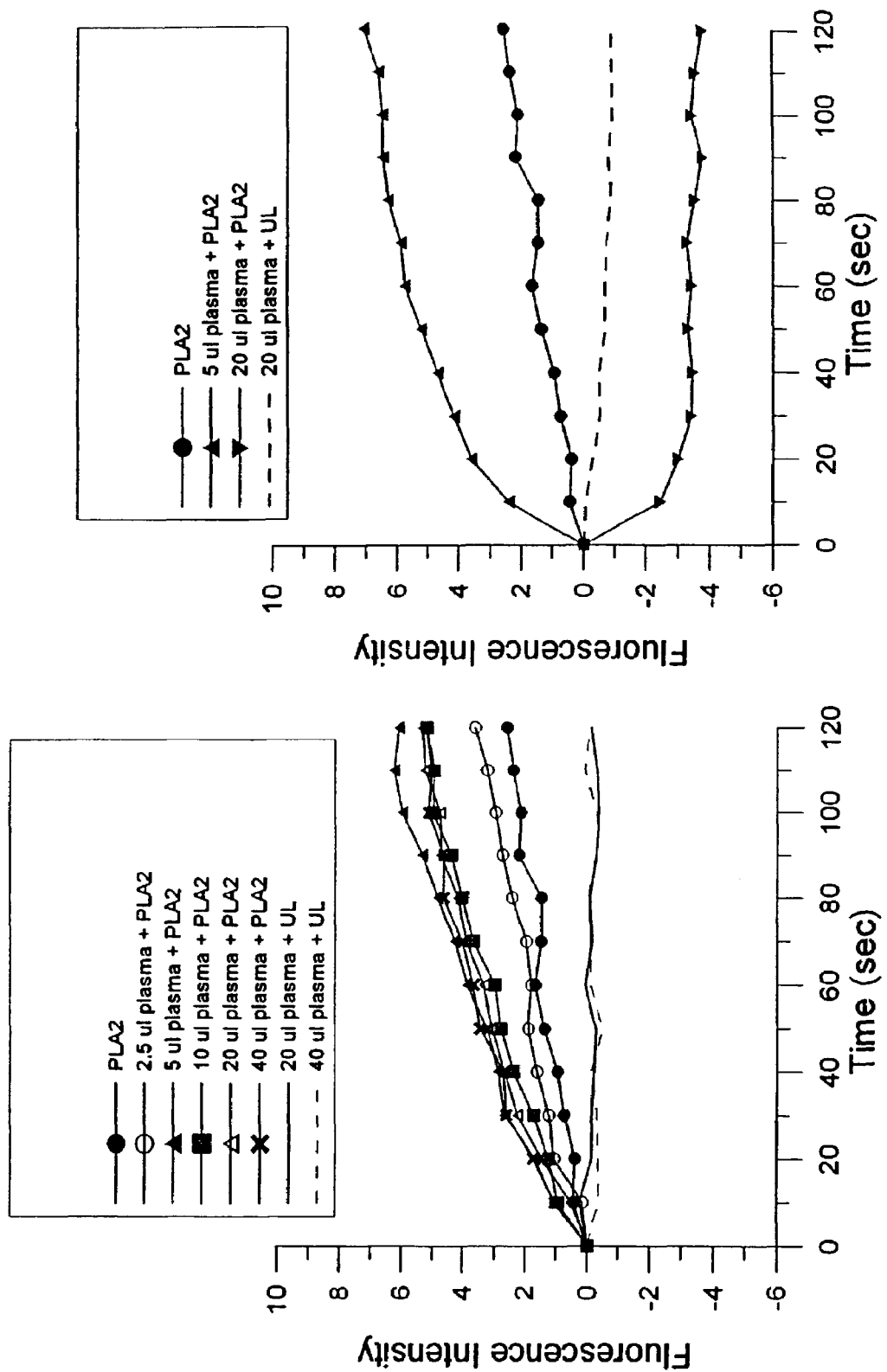
FIG. 11 shows the effect of heating on plasma $PLA_2$-s and $PLA_2$-i activities.
Figure 12:
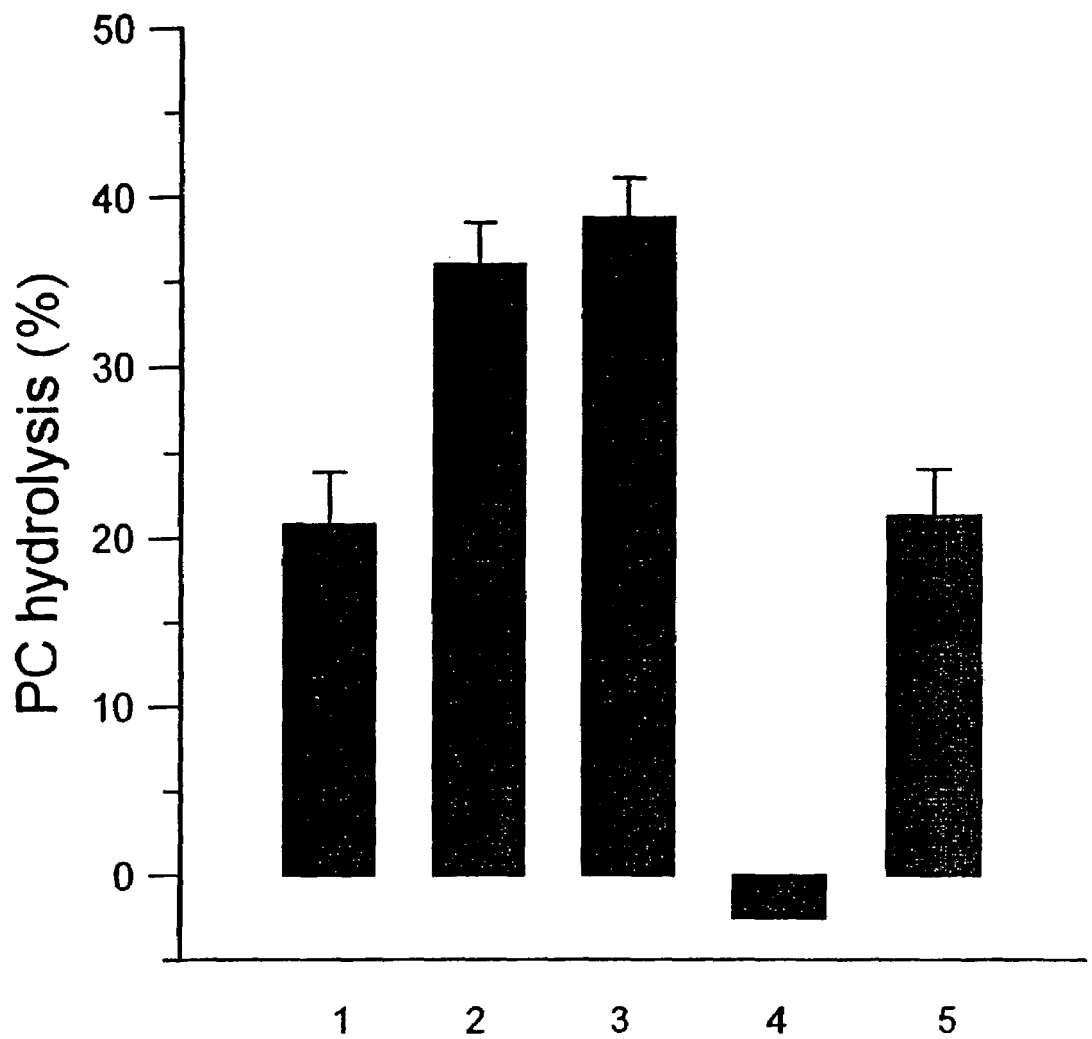
FIG. 12 compares the $PLA_2$-s activity of BALF from a normal human subject and a CF human subject using a radioactive assay.
Figure 13:
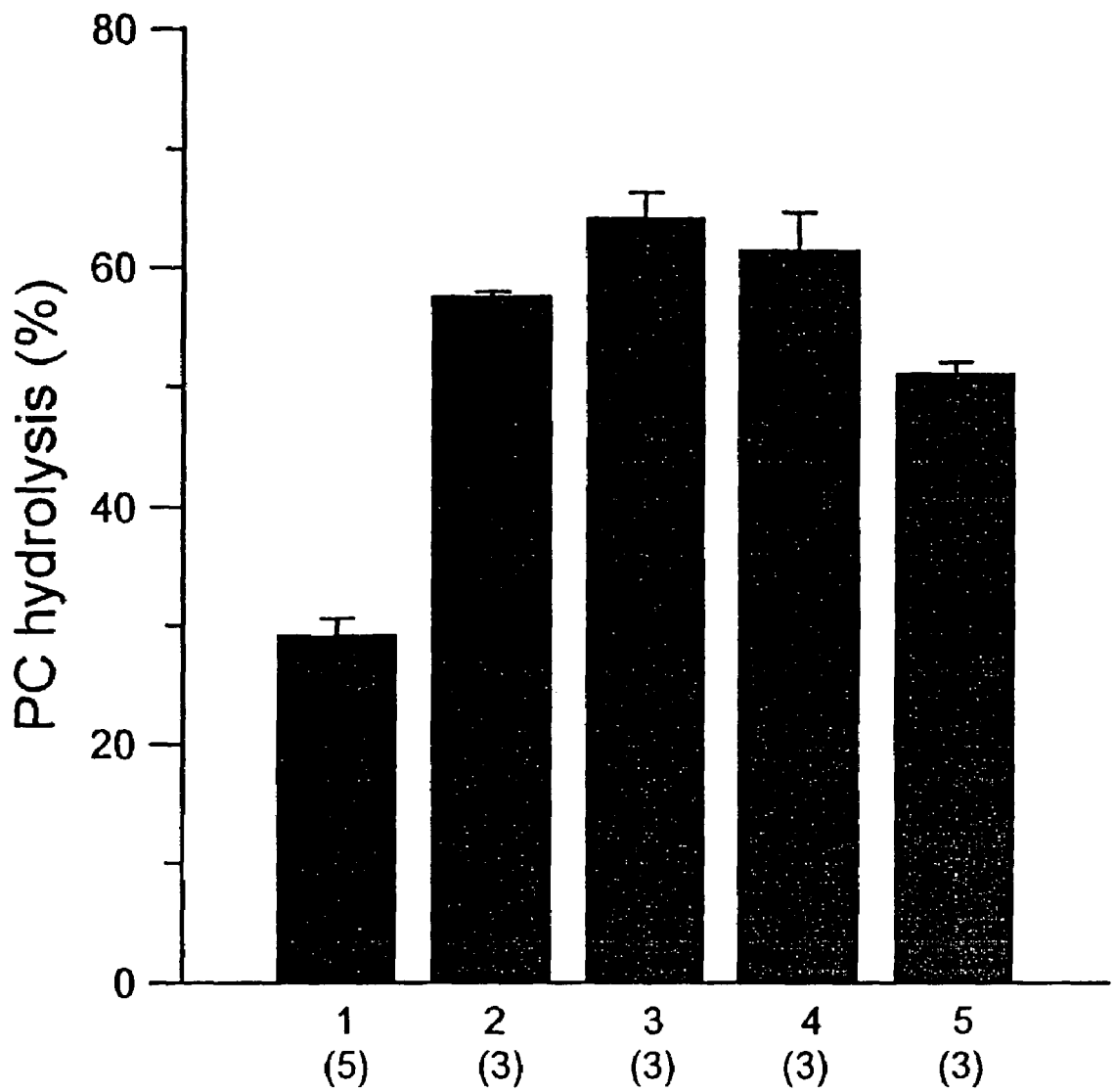
FIG. 13 shows the effect of heating on the $PLA_2$-s activity of BALF from a CF human subject using a radioactive assay.
Figure 14:
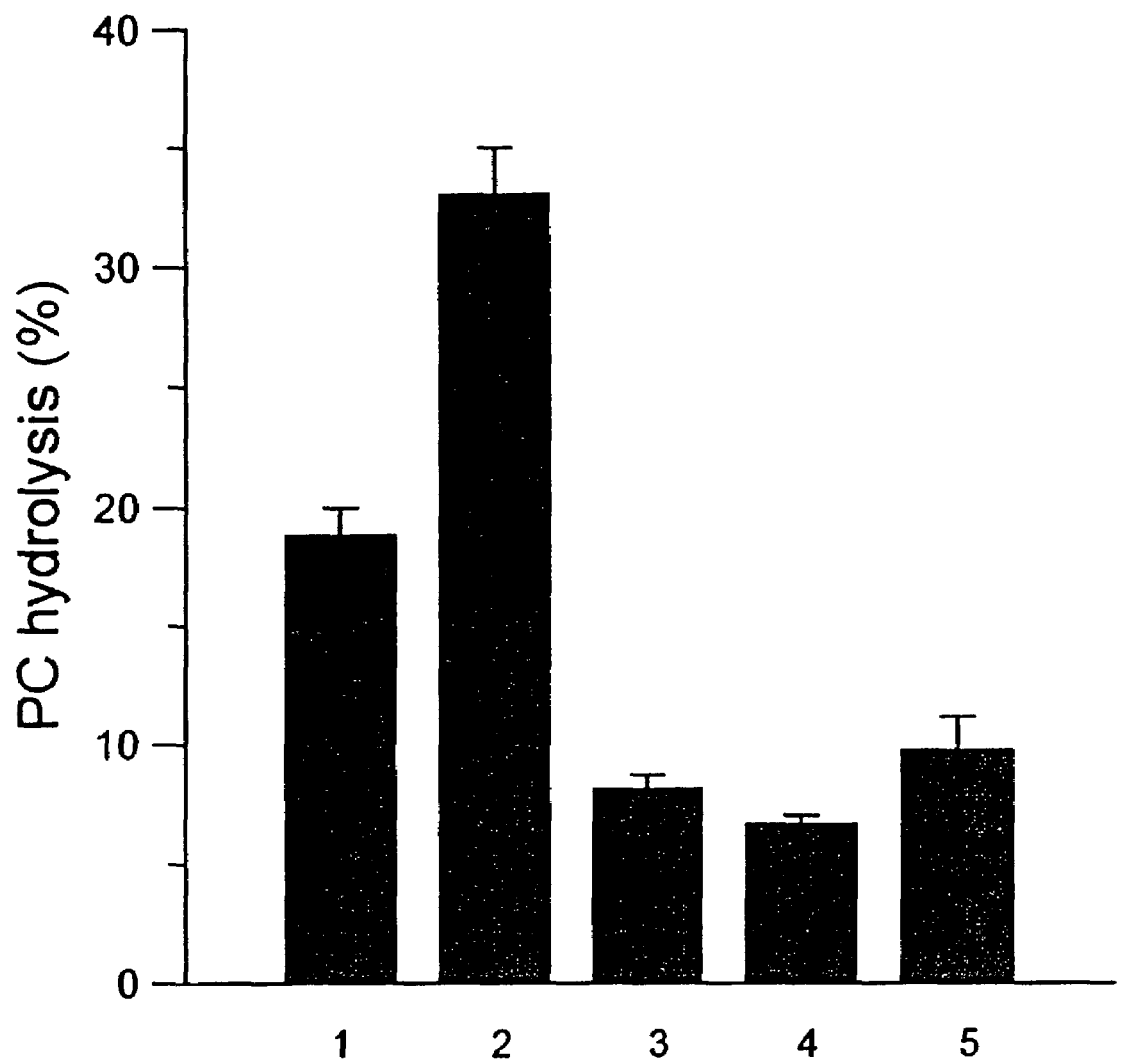
FIG. 14 shows that Annexins I and VIII can inhibit the $PLA_2$ activity and the $PLA_2$-s activity.

Characterization of PLA$_2$-s and PLA$_2$-i: Incubation of plasma in boiling water for 5-10 min considerably diminished PLA$_2$-i activity, but had little effect on PLA$_2$-s activity (FIG. 11). This indicates that PLA$_2$-i and PLA$_2$-s are two different moieties. The molecular weights of PLA$_2$-s and PLA$_2$-i were estimated to be larger than 10 k because both factors were retained in the concentrator with membrane of 10 k molecular weight cut off after BALF or serum was concentrated in the device. Liposomes containing radioactively labeled [1-$^{14}$C] dioleoyl PC were used as PLA$_2$ substrate to determine that the enzymatic products observed in the fluorescently-labeled liposomes were derived from PC hydrolysis. After PLA$_2$ reaction, the amounts of radioactivity were found increasing in fractions of free fatty acids and lysoPC and decreasing in PC, indicating PC hydrolysis. BALFs from CF subjects increased PLA$_2$ activity by nearly 2-fold, whereas the CF BALF itself had no PLA$_2$ activity (FIG. 12). Again, BALFs from normal volunteers had no effect on PLA$_2$ activity (FIG. 12). Heat treatment of CF BALF in boiling water for 5 min also did not diminish PLA$_2$-s activity (FIG. 13). Interestingly, the native lung annexin I and annexin VIII proteins significantly inhibited PLA$_2$ and PLA$_2$-s activities (FIG. 14).

EXAMPLE 2

Effects of BALF on Pancreatic PLA$_2$ Activity

Continuous Fluorescent Assay: We developed a simple and sensitive continuous fluorescent assay of PLA$_2$ using fluorescently labeled unilamellar liposomes as substrate. The unilamellar liposomes were made of dioleoyl phosphatidylcholine (DOPC), phosphatidylglycerol (PG) and fluorescenctly labeled 1,2-bis-(4,4-difluoro-5,7-dimethyl-4-bora-3a,4a-diaza-s-indacene-3-undecanoyl)-sn-glycero-3-phosphocholine (Bis-BODIPY FL C$_{11}$-PC) (Molecular Probes, Eugene, Oreg.) in a molar ratio of 10:10:0.14 as described previously (40). The PLA$_2$ assay was conducted in a single quartz cuvet in which it contained 0.01 M Tris-HCl buffer, pH 7.4, 10 mM CaCl$_2$, 27.3 nmol liposomes phospholipids, and 10 ng porcine pancreatic PLA$_2$. The fluorescence intensity was recorded every 10 sec for 2 min at 21° C. The fluorescence intensity was measured using a Perkin-Elmer Luminescence Spectrometer LS50B equipped with FL WinLab software (Perkin-Elmer Instruments, Norwalk, Conn.) at 488 nm excitatopm (slit 2.5) and 530 nm emission (slit 5.0). To test factors that might affect PLA$_2$ activity in the BALF, an aliquot of the specimen was introduced to the reaction mixture prior to the addition of PLA$_2$.

Figure 15:
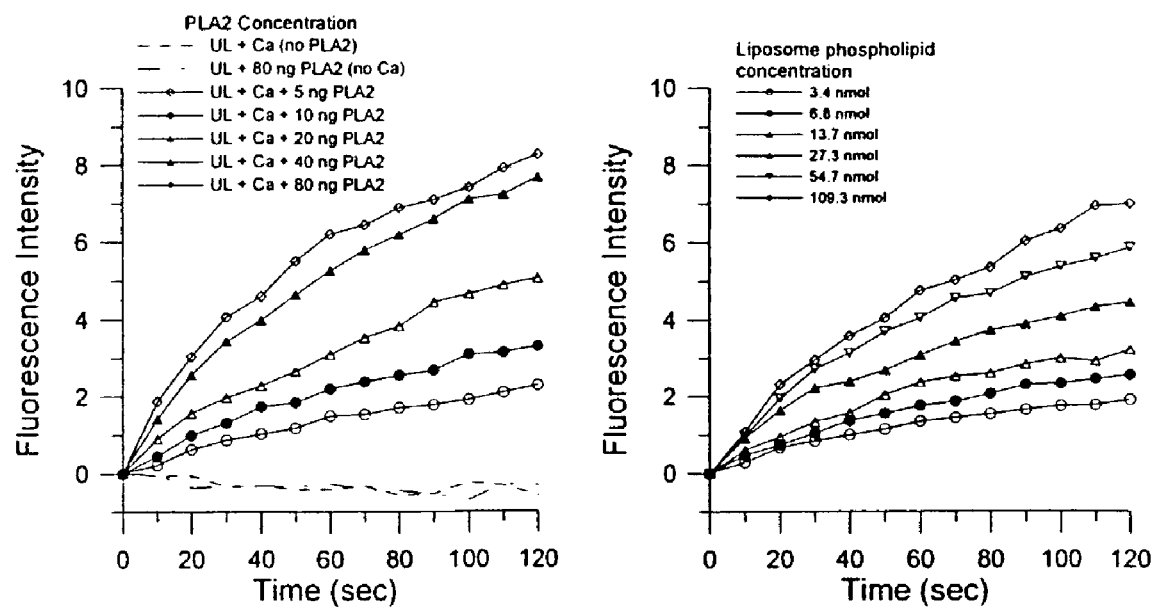
FIG. 15 shows protein and liposome concentration dependence of $PLA_2$ activity determined by the fluorescent assay. Porcine pancreatic $PLA_2$ was used as the enzyme source. Fluorescently labeled unilamellar liposomes were used as substrate.

There was no significant fluorescence intensity change in the reaction mixture containing liposomes and calcium without PLA$_2$, or mixture containing liposomes and PLA$_2$ but no calcium (FIG. 15). However, the fluorescence intensity of the mixture containing all three components increased in a time-dependent fashion within 2 min that was PLA$_2$-dose dependent between 5-80 ng and liposome phospholipid-dose dependent between 3-100 nmol (FIG. 15). The florescence intensity increase was due to the release of fluorescently labeled fatty acid and lysoPC from the quenched membrane environment. In the following studies the fluorescence intensity increase of the control PLA$_2$ reaction was maintained at linear range within 2 min (approximately 3-4 units increase at 2 min in the presence of 10 ng PLA$_2$ and 30 nmol liposome phospholipids).

Figure 16:
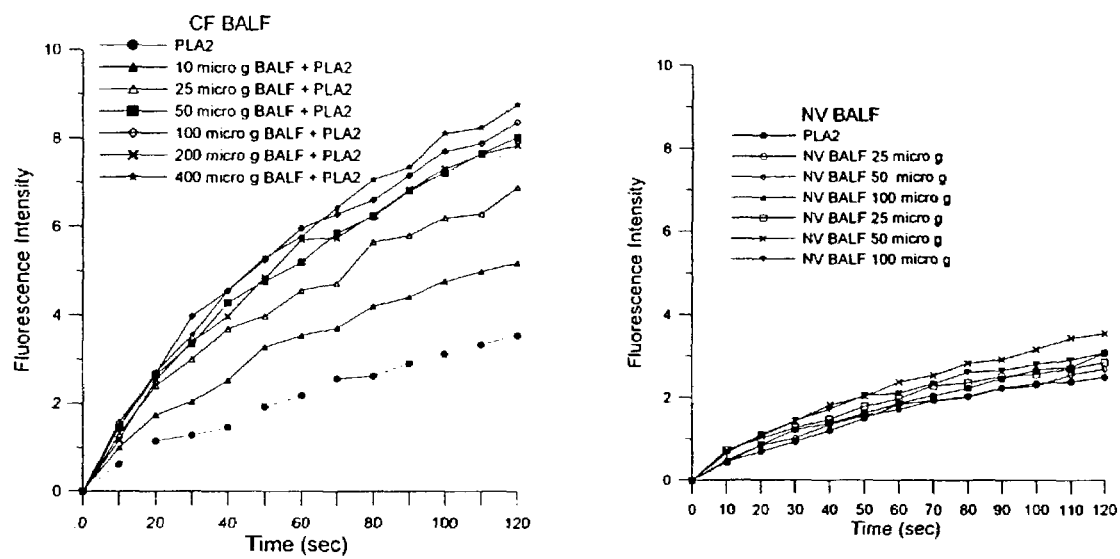
FIG. 16 shows the effect of BALF on $PLA_2$ activity. Left: CF BALF; Right: normal volunteer (NV) BALF.

The specimens of BALF from CF patients were obtained and prepared as previously described (52). Addition of an aliquot of CF BALF to the PLA$_2$ reaction mixture markedly stimulated the PLA$_2$ activity in a BALF dose-dependent manner (FIG. 16 Left). The stimulation reached to the optimal level at 100 μg BALF protein. The average percentage of the stimulation by BALF from 4 individuals with CF (100 μg protein per test sample) was 287.46±57.01%. BALF from normal volunteers (NV) had little effect on the PLA$_2$ activity (FIG. 16 Right). BALF itself had no effect on the fluorescence intensity, indicating that there was no detectable endogenous PLA$_2$ activity in the BALF under the assay conditions. Heat treatment of BALF from subjects with CF in boiling water for 5 min had no significant effect on the PLA$_2$-stimulating activity.

Effect of CF BALF on Bee Venom and Rattlesnake Venom PLA$_2$ Activity

Figure 17:
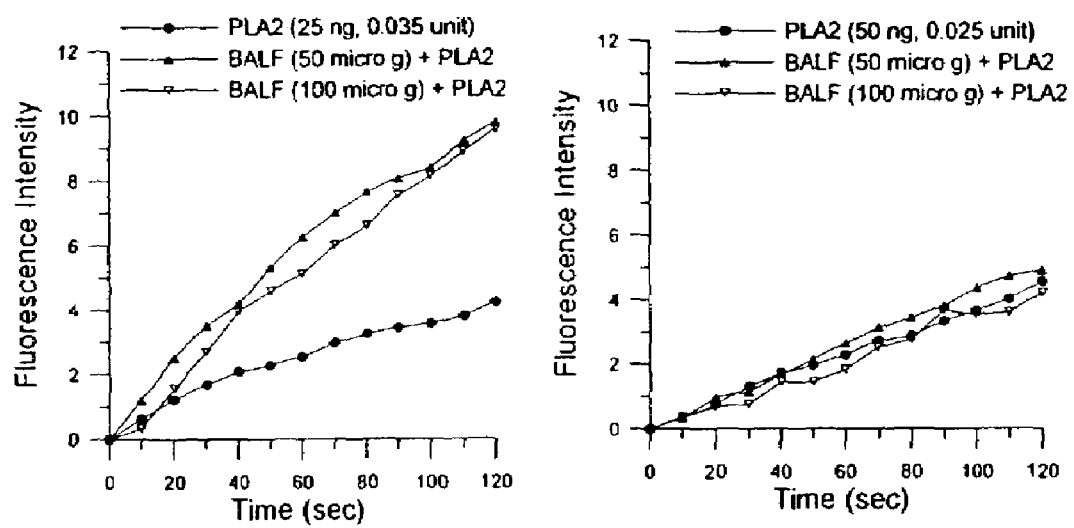
FIG. 17 shows the effect of CF BALF on bee venom $PLA_2$ (Left) and rattlesnake venom $PLA_2$ (Right).

The CF BALF that stimulated pancreatic PLA$_2$ also induced bee venom PLA$_2$ but had no effect on the snake venom PLA$_2$ activity (FIG. 17). Although all the secretory PLA$_2$ have similar molecular weights around 14 kDa, the rattlesnake venom PLA$_2$ is distinct from pancreatic and bee venom $PLA_2$ in that it is dimeric in structure and active in the dimeric state (53). These results suggest that the CF BALF stimulation was more specific for pancreatic- and non-pancreatic-type $PLA_2$ that includes the human $PLA_2$-I and $PLA_2$-II.

Isolation and Identification of the $PLA_2$-Stimulating Factor in the CF BALF

Figure 18:
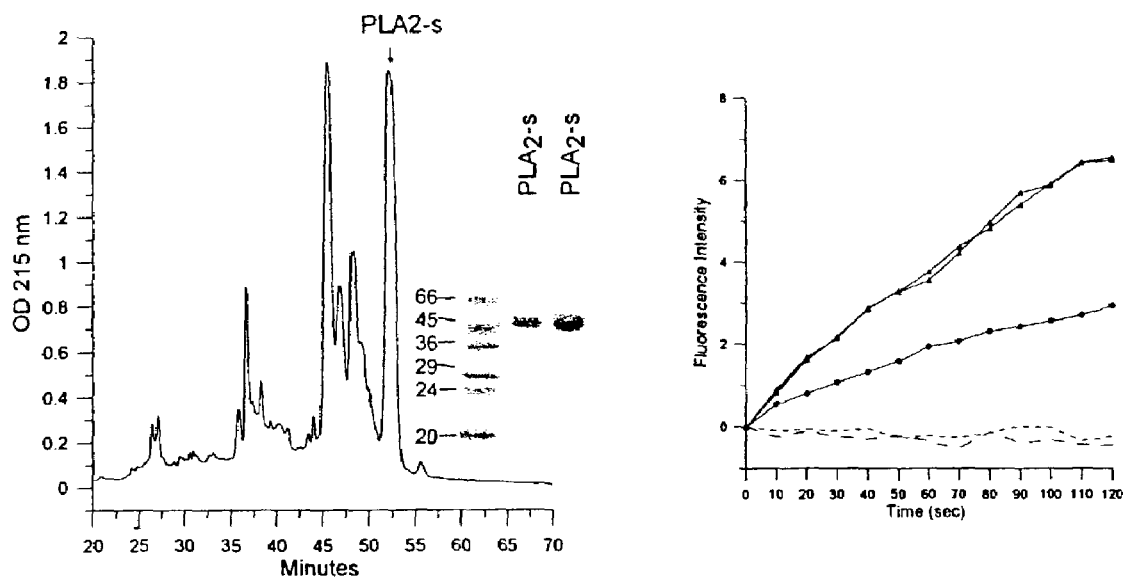
FIG. 18 shows reverse phase HPLC chromatogram and SDS gel electrophoresis of $PLA_2$-s (left) and the effect of the isolated $PLA_2$-s on pancreatic $PLA_2$ activity (right). The $PLA_2$-s samples applied to the SDS gel were from two HPLC preparations. An amount of 6 μg of $PLA_2$-s from two different HPLC preparations was tested by the fluorescent assay. The dotted lines represent the reaction containing $PLA_2$-s, liposomes and $Ca^{2+}$ but no $PLA_2$.

Protein isolation: A pool of BALF from two CF subjects (160 ml) were treated in boiling water for 7 min and the denatured proteins were discarded by centrifugation. The supernatant was concentrated and the concentrate was employed for protein isolation by the methods of gel filtration, anionic exchange, and reverse phase high performance liquid chromatography (HPLC). The activity of the $PLA_2$-stimulating activity was traced by using the fluorescent assay. One single protein possessing the $PLA_2$-stimulating activity (named $PLA_2$-s) was isolated. The $PLA_2$-s isolated by the reverse phase HPLC showed a single band with an apparent molecular weight of 48 kDa on sodium dodecyl sulfate polyacrylamide (SDS) gel (FIG. 18 Left). The purified $PLA_2$-s also exhibited $PLA_2$-stimulating activity (FIG. 18 Right).

Protein structure determination and identification: The protein band of $PLA_2$-s on the SDS gel was excised and digested with trypsin. The trypsin-digested peptides were used for mass and peptide sequence determination by the methods of "matrix-assisted laser desorption ionization" (MALDI) and tandem mass spectrometry (MS/MS) conducted at the Biotechnology Center (UWBC) on the University of Wisconsin campus. The $PLA_2$-s peptide sequences, after searching in the GenBank database, matched human $\alpha 1$-AT. The matched peptide sequences are shown in Table 1. SDS gel electrophoresis showed that the apparent molecular weight of the truncated a $\alpha 1$-AT was indeed less than the intact human serum $\alpha 1$-AT which is a 52 kDa protein.

TABLE 1

Peptide mass and sequence of $PLA_2$ stimulator isolated from BALF.

| Peptides | Amino acid sequences | Amino acid residue location at human α1-AT |
|---|---|---|
| 1 | IVDLVK | 169-174 |
| 2 | LSSWVLLMK | 235-243 |
| 3 | LSITGTYDLK | 291-300 |
| 4 | GTEAAGAMFLEAIP | 344-357 |
| 5 | ITPNLAEFAFSLYR | 26-39 |
| 6 | VFSNGADLSGVTEE | 311-324 |
| 7 | TLNQPDSQLQLTTG | 102-115 |

The native human $\alpha 1$-AT molecular weight is 52 kDa. Apparently, the purified 48 kDa $\alpha 1$-AT from CF BALF was the truncated $\alpha 1$-AT. This finding is consistent with previous report that $\alpha 1$-AT in the BALF from CF patients with inflamed lungs was a 48 kDa proteolytic product. It is known that the truncated $\alpha 1$-AT has no activity against neutrophil elastase (45).

EXAMPLE 3

Materials and Methods

Continuous fluorescent assay of $PLA_2$: Liposomes were prepared by the method as previously described (40). In this method phospholipids of 2.04 µmol dioleoyl phosphatidylcholine (DOPC), 2.04 µmol phosphatidylglycerol (PG) and 0.02 µmol fluorescenctly labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) (Molecular Probes, Eugene, Oreg.) were dissolved in about 1 ml chloroform. The chloroform was then evaporated to dryness under a stream of nitrogen. The dried phospholipid residues were suspended in 1.5 ml sucrose/Tris buffer (0.25 M sucrose, 50 mM Tris-HCl, 0.02% sodium azide, pH 7.4). The suspension was stirred occasionally with vortex within 30 min. Then, the phospholipid suspension was sonicated for 30 see on ice and repeated 6 times using a Virsonic cell disrupter (VirSonic, Gardiner, N.Y.). The 50%PC-50%PG liposomes were stored at 4° C. before use.

The $PLA_2$ assay was conducted in a 3 ml quartz cuvet in which 2.96 ml 0.01 M Tris-HCl containing 0.02% sodium azide, pH 7.4, was first added, followed by adding 30 µl of 1 M $CaCl_2$ and 10 µl of liposomes (27.3 nmol phospholipids). The solution was mixed well by three times inversion of the cuvet covered with a piece of parafilm. Then, an aliquot of $PLA_2$ working solution (0.01 µg in 2-3 µl) was added to the reaction mixture followed by rapid inversion of the cuvet three times. Fluorescence intensity was immediately recorded every 10 sec for 2 min at 21° C. (room temperature). The fluorescence intensity was measured using a Perkin-Elmer Luminescence Spectrometer LS50B equipped with FL WinLab software (Perkin-Elmer Instruments, Norwalk, Conn.) at 488 nm excitation (slit 2.5) and 530 nm emission (slit 5.0). To test factors that might affect $PLA_2$ activity in the plasma, serum or BALF, an aliquot of the specimen was introduced to the reaction mixture prior to the addition of $PLA_2$ in a final volume of 3 ml. Then, $PLA_2$ was added and fluorescence intensity was recorded. In some tests, the fluorescence intensity of the reaction solution without the presence of $PLA_2$ was recorded for up to 2 min to obtain the background reading.

Determination of endogenous $PLA_2$ activity in plasma and synovial fluid by fluorescent assay: To determine the endogenous $PLA_2$ activity in specimens, the assay was conducted at 37° C., instead of at room temperature. The reaction components were the same as that described above; 3 ml Tris buffer containing Bis-BODIPY FL $C_{11}$-PC-labeled liposomes (27.3 nmol) and 10 mM $CaCl_2$ in the presence or absence of specimens specified. The cuvet holder of the luminescence spectrometer was connected to a water bath with circulating water that kept the cuvet holder at 37° C. and the buffer was maintained at 37° C. in the water bath. Prior to determining the $PLA_2$ activity in the specimen, the cuvet that contained prewarmed buffer, liposome and calcium (in the absence or presence of CF BALF) was kept in the cuvet holder to allow the temperature to be equilibrated at 37° C. for 4 min. Then, the specimen to be tested was added to the reaction mixture and the reaction was carried out at 37° C. The fluorescence intensity was recorded every 10 sec for 2 min.

Isolation and characterization of $PLA_2$-i and $PLA_2$-s from human serum: Gel filtration—A total of 14 ml of human sera from healthy volunteers was employed to isolate $PLA_2$-i and $PLA_2$-s. One half of the serum was applied to a SEPHADEX G100 (Pharmacia, Piscataway, N.J.) column (2.6×55 cm) equilibrated with Tris-EDTA-NaCl buffer (0.01 M Tris-HCl, 5 mM 2-mercaptoethanol, 1 mM EDTA and 0.15 M NaCl, pH 7.4). The proteins were eluted with the Tris-EDTA-NaCl buffer at a flow rate of 12 ml per hour and collected in 2 ml per tube. Protein in each fraction was detected by absorbance at 280 nm and the $PLA_2$-i and $PLA_2$-s activities were determined by the fluorescent assay. The $PLA_2$-s activity was determined using 40 µl of the fraction and $PLA_2$-i activity was determined using 150 µl of the fraction. Fractions that contained $PLA_2$-i and $PLA_2$-s activities were pooled, equilibrated with 0.01 M Tris-HCl, pH 7.4, and concentrated to about 1 ml for next step of isolation. Similarly, the second half of the sera was run through the G100 column by the same manner.

To isolate $PLA_2$-s from BALF, a total of 160 ml BALF collected from two subjects with CF were heated in boiling water for 5 min. The denatured proteins were removed by centrifugation at 10,000 rpm. The supernatant was concentrated to 25 ml. An aliquot of 8 ml of the concentrated supernatant was applied to the SEPHADEX G100 column as described above. Three runs were performed. Fractions contained $PLA_2$-s activity from all three runs were pooled and concentrated to about 1 ml for next step isolation.

Isolation and characterization of $PLA_2$-i and $PLA_2$-s from human serum: Anionic exchange column chromatography—One half of the $PLA_2$-i/$PLA_2$-s solution (from serum) or $PLA_2$-s solution (from BALF) from SEPHADEX G100 column was applied to a high performance liquid chromatography (HPLC) anionic exchange MonoQ column (5×50 mm) (Pharmacia) equilibrated with 0.01 M Tris-HCl buffer, pH 7.4. The column was eluted with 0.01 M Tris buffer with an ascending gradient of 1 M NaCl in Tris buffer. The column was first eluted for 10 min with 0.01 M Tris buffer, then with 25% of 1 M NaCl for 100 min, 50% of 1 M NaCl for 30 min, and finally with 100% of 1 M NaCl for 10 min. The flow rate was 1 ml/min and the collected fraction volume was 1 ml per fraction tube. Protein in each fraction was determined by absorbance at 280 nm and the $PLA_2$-i and $PLA_2$-s activities were determined by the fluorescent method.

Isolation and characterization of $PLA_2$-i and $PLA_2$-s from human serum: Reverse phase column chromatography—The $PLA_2$-i/$PLA_2$-s or $PLA_2$-s fractions obtained from HPLC MonoQ column chromatography were pooled, concentrated and applied to a reverse phase HPLC Vydac C4 column (4.6×250 mm, Separations Groups, Hesperia, Calif.). The column was eluted with a gradient of solvent A of 0.1% trifluoroacetic acid (TFA) and solvent B of 0.086% TFA in 80% acetonitrile at a flow rate of 1 ml/min. The proteins were eluted with the following gradient program: 10% B for an initial 2 min, then a gradient of 10-70% B in 60 min. Protein in each fraction was determined by absorbance at 215 run and 280 nm and the $PLA_2$-i and $PLA_2$-s activities were determined by the fluorescent method.

Isolation and characterization of $PLA_2$-i and $PLA_2$-s from human serum: Sodium dodecyl sulfate polyacrylamide gel electrophoresis (SDS-PAGE)—The amounts of proteins were determined by the methods of Lowry et al. (41) with modifications suitable for microtiter plate assay. A specified amount of protein (1-10 μg) was employed for protein separation using a Bio-Rad Mini-PROTEAN 3 Cell Assembly Unit with the use of a 10% SDS Ready gel (Bio-Rad, Hercules, Calif.) under denaturing conditions. Proteins separated on the gel were stained with Coomassie brilliant blue solution followed by destaining.

Structure determination and identification of $PLA_2$-i and $PLA_2$-s: The protein band on the SDS gel was excised and placed into a 0.5 ml microcentrifuge tube. The gel was treated in 100 μl 25 mM $NH_4HCO_3$/50% acetonitrile to remove the Coomassie blue stain. The de-colored gel was dried in a vacuum centrifuge. The protein was reduced in 100 mM dithiothreitol followed by modification with 55 mM iodoacetamide. Then the protein was digested with trypsin (Sequencing Grade Modified, Promega) solution (20 μl of 0.006 mg/ml) at 37° C. for 24 hours. The peptides were collected by washing the gel with water followed by washing with 5% trifluoroacetic acid/50%acetonitrile. The washes were combined and dried in a vacuum centrifuge. The dried peptides were used for mass and peptide sequence determination using the methods of "matrix-assisted laser desorption ionization" (MALDI) and tandem mass spectrometry conducted at University of Wisconsin—Madison Biotechnology Center (UWBC, Madison, Wis.) on campus. The peptides of trypsin-digested protein in SDS gel were also used to determine the amino acid sequences by the tandem mass spectrometry (MS/MS) method using the TOF instruments at UWBC.

Fluorescent assay of phospholipase C (PLC) and lipase: The fluorescent assay of PLC (*Clostridium perfringens*, Sigma) was the same as $PLA_2$ fluorescent assay, except $PLA_2$ was replaced with a specified amount of PLC (0.01 to 0.05 unit) in the reaction mixture. The fluorescence intensity was recorded every 10 sec for 2 min after PLC was introduced into the reaction mixture. In some studies, an amount of 0.14 unit of porcine pancreatic lipase (Sigma) was added to the reaction mixture after 2 min of PLC reaction. Then, the fluorescence intensity was continuously recorded every 10 sec for another 2 min.

Radioactive labeling of neutrophils (PMN) with $^3$H-arachidonic acid and study of the effects of $PLA_2$, BALF and plasma on $^3$H-PMN: Neutrophils were isolated from peripheral blood from a normal volunteer using the neutrophil isolation media (Polymorphprep™, Axis-Shield PoC AS, Oslo, Norway). A total of $38.6\times10^6$ PMN were obtained from 20 ml peripheral blood. An amount of $5.5\times10^6$ PMN was added to 1 ml RPMI culture medium containing 5% fetal calf serum, 2 mM glutamine, 10 mM HEPES, penicillin (200 U/ml), streptomycin (200 U/ml), amphotericin (500 ng/ml), and 5 μCi $^3$H(N)-AA (Sigma) in a well of a 6-well dish. Neutrophils were cultured at 37° C. in a 5% $CO_2$ incubator for 20 hours. After incubation all radioactively labeled cells were harvested and combined. The medium was removed by centrifugation and cells were washed with 10 ml ice-cold incomplete Hanks balanced salt solution (HBSS) two times. The cells were suspended in 2 ml HBSS and used for $PLA_2$ studies. A small amount of PMN was cultured in non-radioactive medium under the same conditions as that of radioactive labeling of PMN and was used for cell viability and morphology analyses.

$PLA_2$ reaction was conducted in 1 ml HBSS containing 1 mM $CaCl_2$ and $2\times10^6$ $^3$H-labeled PMN in the presence or absence of pancreatic $PLA_2$, BALF, or plasma as specified in a 10-ml culture tube. The reaction tube was incubated at 37° C. for 10 min with frequent shaking. The reaction was stopped on ice followed by centrifugation at 2,000 rpm for 10 min to precipitate the cells. The supernatant was removed; the cells were washed with 10 ml ice-cold HBSS twice and washes discarded. The cells were suspended in 0.1 ml lysis buffer (0.01 M Tris-HCl, 1 mM EDTA, 5 mM 2-mercaptoethanol, 1% Igepal CA-630 nonionic detergent, and 2 mM PMSF, pH 7.4) and sonicated on ice for 30 sec. Lipids in cell homogenate were extracted with chloroform/methanol by the method of Bligh and Dyer (42). Phospholipids, lysophospholipids, neutral lipids and fatty acids were separated by thin-layer chromatography (TLC) and their radioactivity was determined as previously described (43).

Results

Figure 19:
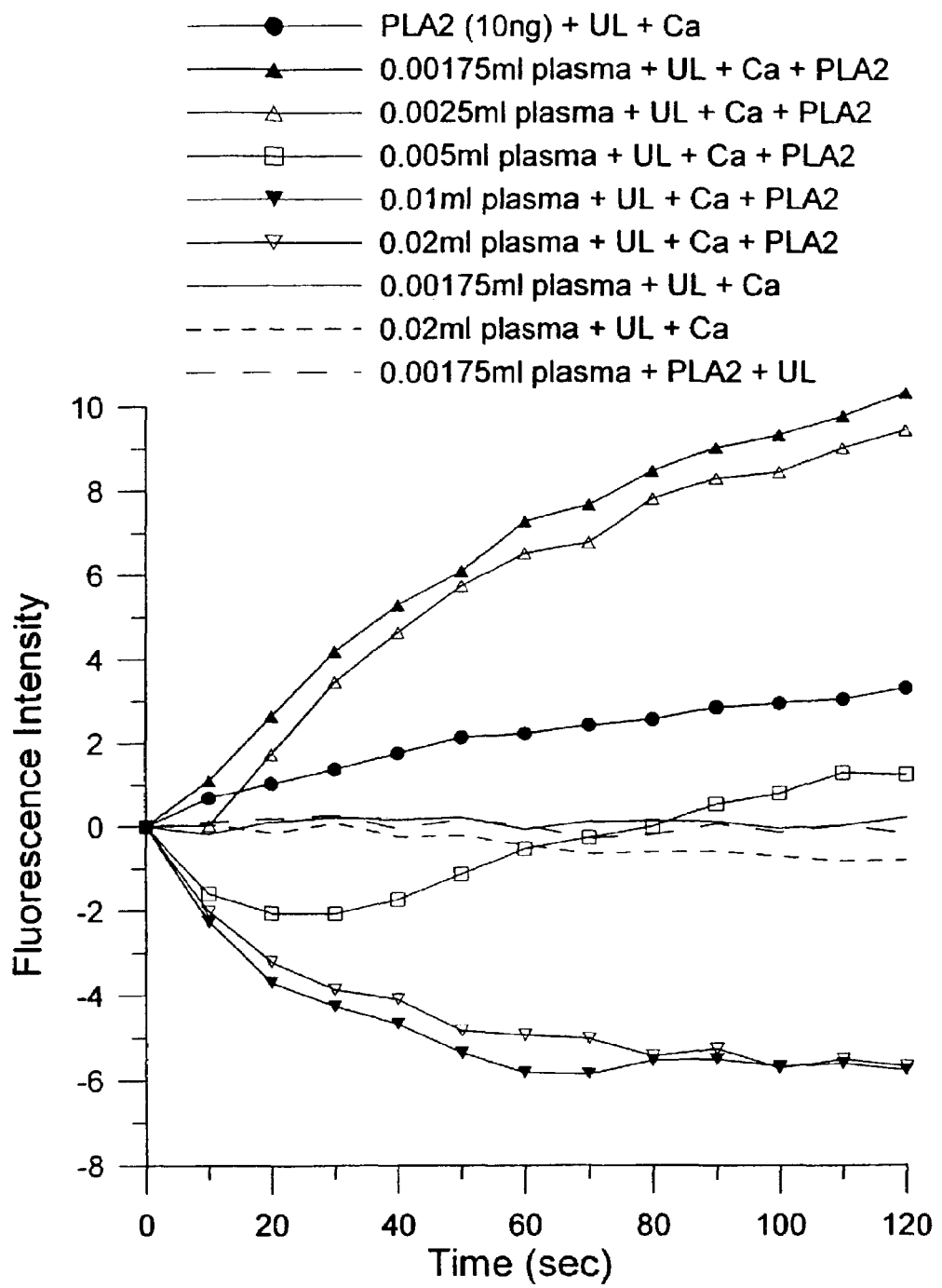
FIG. 19 shows the effects of plasma on pancreatic $PLA_2$ activity using the fluorescent assay. The assay mixture contained fluorescently labeled liposomes, 10 mM $CaCl_2$, and in the presence or absence of $PLA_2$ or plasma as detailed in the text. The reaction was carried out at room temperature.

Effects of plasma, serum and BALF on $PLA_2$Activity: The effects of plasma from healthy subjects on $PLA_2$ activity varied depending on the amount of plasma in the assay. In the presence of plasma less than 2.5 μl in the assay mixture, the $PLA_2$ activity expressed as fluorescence intensity increase was stimulated, and the stimulation was plasma dose-dependent (FIG. 19). However, when the volume of plasma in the assay increased, not only PLA$_2$ activity was inhibited, the fluorescence intensity also dropped below the baseline. For example, with the presence of 5 µl of plasma, the fluorescence intensity decreased in the first 30 sec, and then gradually increased afterward. When the plasma volume increased to 10 µl, the fluorescence intensity was reduced to the minimal levels far below the baseline. Further increase in plasma to 20 µl had nearly the same effect as 10 µl plasma. Similar results were obtained from plasma samples obtained from several healthy individuals. We observed that 1.75 µl plasma from a number of healthy subjects provided maximal PLA$_2$ stimulating effect and 10 µl plasma was the minimal volume that yielded optimal PLA$_2$ inhibitory effect. In the absence of PLA$_2$, the amounts of plasma ranging from 1.75 µl to 20 µl had no effect on the fluorescence intensity under the assay conditions at room temperature (21° C.) (FIG. 19).

Figure 20:
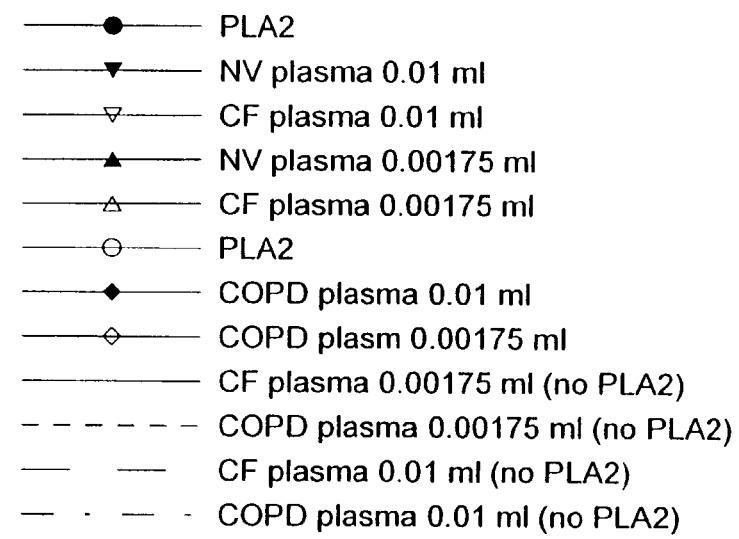
FIG. 20 compares the effects of plasma from a normal volunteer (NV) and subjects with CF or COPD on $PLA_2$ determined by the fluorescent assay.
Figure 20:
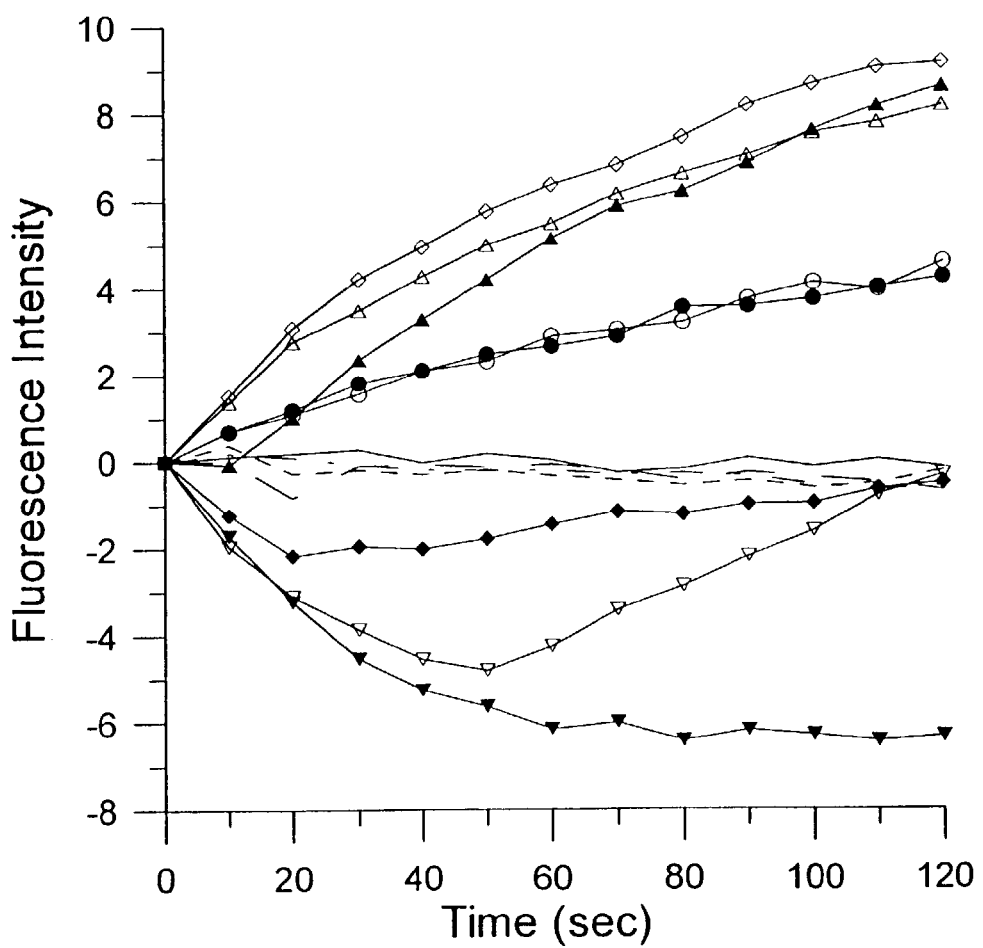

The presence of 1.75 µl of plasma from subjects with CF or COPD also stimulated PLA$_2$ activity similar to that stimulated by the plasma from healthy subjects. Representative examples are shown in FIG. 20. However, the effects of 10 µl plasma from subjects with CF or COPD had less PLA$_2$ and fluorescent intensity inhibitory effects than that from healthy subjects. Again, in the absence of PLA$_2$, the plasma had little effect on the fluorescence intensity under the assay conditions at room temperature (FIG. 20).

We quantified the total PLA$_2$ activity by adding up each fluorescence intensity change at 10 sec interval within 2 min reaction time. The total fluorescence intensity (TFI) is more reliable than a single reading of the initial rate. Also, because of both stimulating and inhibiting effects of plasma on PLA$_2$ activity and fluorescence intensity, TFI appears to be more representative of the effects of the plasma. The TFI of PLA$_2$-i (10 µl plasma) and PLA$_2$-s (1.75 µl plasma) were also determined by the same manner. The average TFI value of 29 different assays of PLA$_2$ was 23.37±4.77. The TFI values of PLA$_2$-i were in the negative range because of fluorescence quenching. Thus, higher negative value of TFI represents higher PLA$_2$-i activity. Among the tested specimens, the TFI values of 10 µl plasma from NV were about 40-50% higher than that from subjects with CF or COPD or from a cigarette smoker (Table 2). However, the PLA$_2$-s activities of all groups were insignificantly different. The plasma albumin levels of CF and COPD subjects were about 5% and 25% lower than that of the normal subjects, respectively (Table 2).

Figure 21:
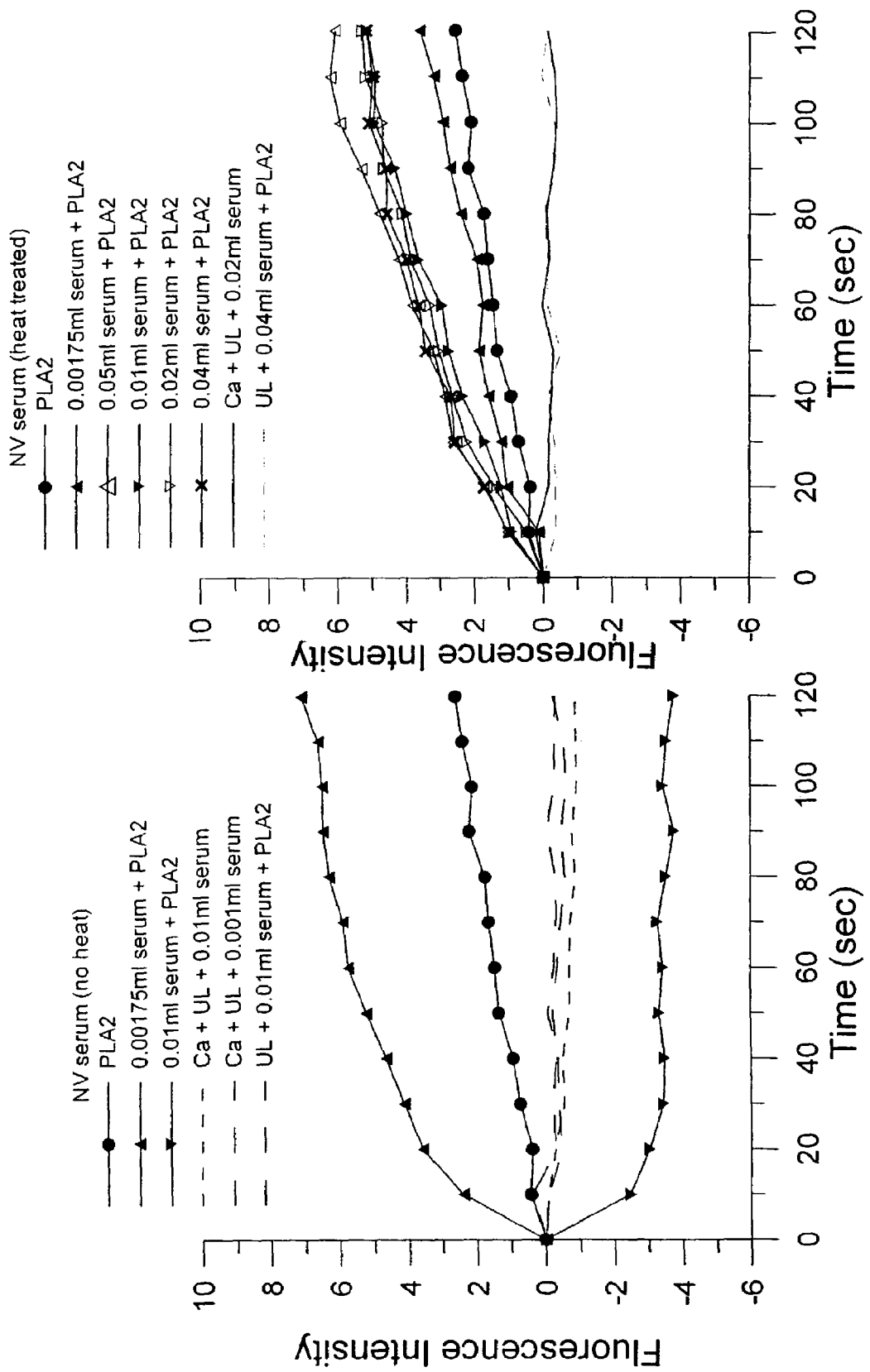
FIG. 21 shows effects of prior (left) or after (right) heat treatment of serum on $PLA_2$ activity determined by the fluorescent assay. Serum was obtained from a normal volunteer (NV). Heat treatment of serum was conducted by immersing serum in boiling water for 5 min followed by centrifugation to remove precipitated proteins. The supernatant was used for assay.

The PLA$_2$-s or PLA$_2$-i activities were also present in the serum (FIG. 21). Heat treatment of serum in boiling water for 5 min had markedly different effects on the PLA$_2$-i and PLA$_2$-s activities. With 1.75 µl heat-treated serum, the stimulating activity was nearly totally diminished. With 10 µl plasma, the inhibitory activity was completely abolished; instead, it showed stimulating activity. Increasing plasma to 20 µl or 40 µl still had no inhibitory activity; there was only stimulating activity. The stimulating activity reached the maximal level with 10 µl of serum. These results suggest that there are probably two separate factors, a heat-liable inhibitor (PLA$_2$-i) and a heat-stable stimulator (PLA$_2$-s) in the serum or plasma that affect the PLA$_2$ activity.

Plasma was isolated within 60 min after blood was drawn. Both PLA$_2$-s and PLA$_2$-i activities in the freshly isolated plasma had no significant change after plasma was set on ice for more than 5 hours or stored at −70° C. for more than three days.

Figure 22:
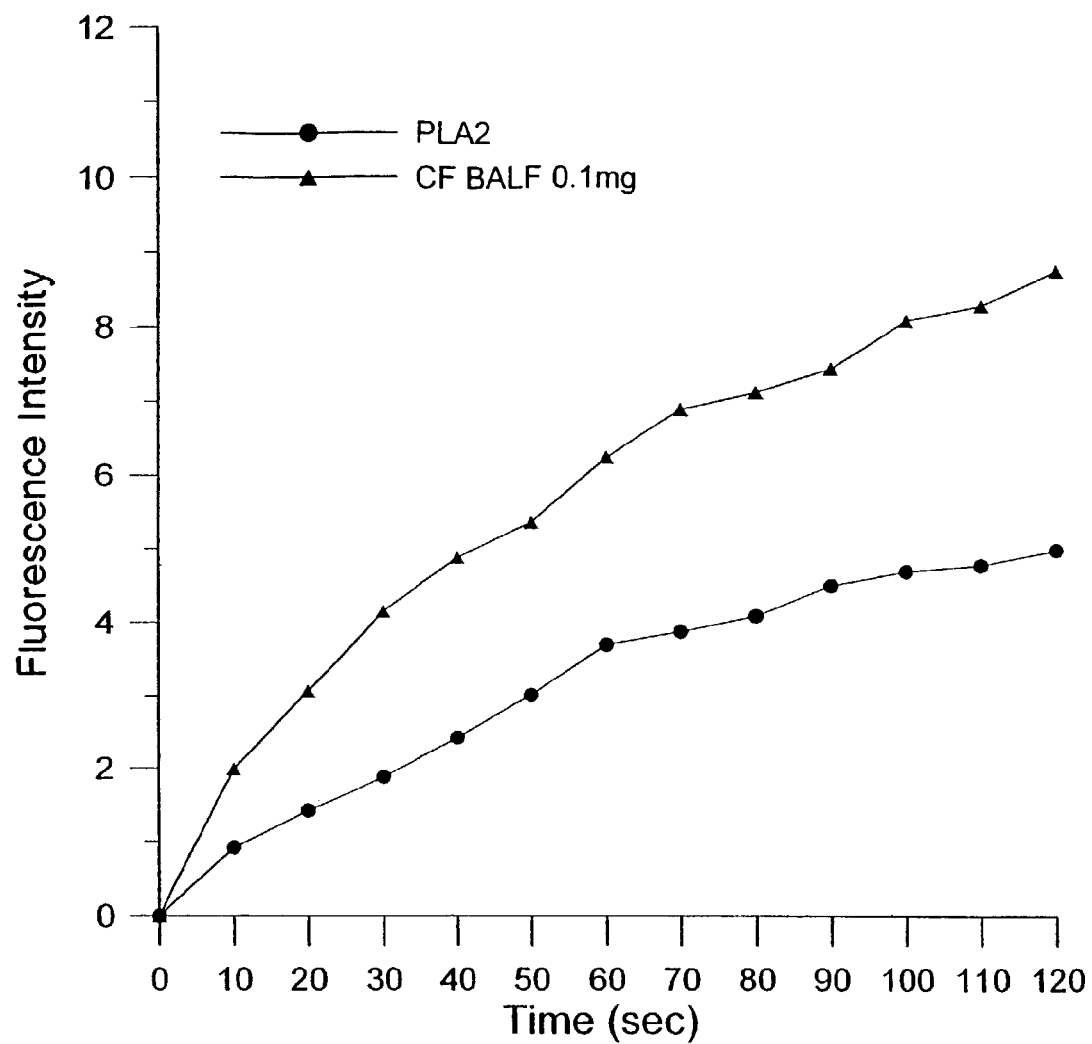
FIG. 22 shows the effect of BALF from CF subject on pancreatic $PLA_2$ activity determined by the fluorescent assay.

As described in Example 1, CF BALF also contained a PLA$_2$-s (FIG. 22). Much of the experiments and results of BALF PLA$_2$-s isolation and identification were described in Example 2.

Determination of endogenous PLA$_2$ activity in plasma and synovial fluid: When the fluorescent assay was carried out at room temperature, the plasma, either from NV or CF, did not produce any increase in fluorescence intensity (FIGS. 19 and 20), i.e., no endogenous PLA$_2$ activity in the plasma could be determined. However, when the assay temperature increased to 37° C., plasma in the reaction mixture caused a time-dependent increase in fluorescence intensity without addition of porcine pancreatic PLA$_2$. The amount of TFI generated by the plasma increased with increasing amount of plasma (from 1 µl to 2.5 µl) in the reaction mixture (Table 3). The increase in fluorescence intensity was probably due to factors other than PLA$_2$ in the plasma. This is probably why that there was no apparent difference in the amounts of TFI between NV and CF plasma. However, the presence of heat-treated CF BALF in the reaction mixture increased the fluorescence intensity of the CF plasma, but the stimulation diminished with plasma volume greater than 2.5 µl. In contrast, CF BALF had little effect on the fluorescence intensity of NV plasma among the tested samples ranging from 1 to 2.5 µl plasma (Table 3). The increase in fluorescence intensity in the CF plasma caused by

TABLE 2

Total fluorescence intensity (TFI) of PLA$_2$-i and PLA2-s and amount of albumin in plasma.

| Sample | PLA$_2$-i (TFI) Mean ± SD | % | PLA$_2$-s (TFI) Mean ± SD | % | s/i Ratio | Albumin Mean ± SD | % |
|---|---|---|---|---|---|---|---|
| Normal | −61.89 ± 5.61 (16) | 100 | 70.96 ± 18.95 (16) | 100 | −1.14 ± 0.26 | 3.9 ± 0.2 (8) | 100 |
| (Range) | (−53.10 to −74.11) | | (67.65 to 113.39) | | (−0.84 to −1.72) | | |
| CF | −37.22 ± 10.51 (7)* | 60.1 | 79.69 ± 20.04 (7) | 112.3 | −2.40 ± 1.20 | 3.7 ± 0.3 (5) | 94.9 |
| (Range) | (−18.02 to −50.61) | | (52.83 to 114.14) | | (−1.20 to −4.61) | | |
| COPD | −27.59 ± 14.56 (4)* | 44.6 | 56.65 ± 14.13 (4) | 79.8 | −2.59 ± 1.55 | 2.9 ± 0.4 (3) | 74.4 |
| (Range) | (−14.27 to −43.64) | | (37.69 to 64.52) | | (−1.16 to −4.62) | | |
| Smoker | −34.49 | 55.7 | 64.89 | 91.4 | −2.62 | | |

Numbers of samples are shown in parenthesis.
*p < 0.05 (t-test) compared to NV.
The value of TFI of the control PLA$_2$ was 23.37 ± 4.77 of 29 assays.

CF BALF was due to the stimulation of the endogenous PLA$_2$ activity in the CF plasma by CF BALF.

TABLE 3

Fluorescent assay of endogenous PLA$_2$ activity in plasma and the effect of CF BALF.
The reaction mixture contained 27.3 nmol PC-PG (50%-50%) UL labeled with Bis-BODIPY FL C$_{11}$-PC, 10 mM CaCl$_2$ in 3 ml 0.01 M Tris-HCl, pH 7.4 under conditions described in the Table. The assay was conducted at 37° C. for 2 min.

| Condition | Plasma volume (µl) | PLA$_2$ activity (TFI) | % control |
|---|---|---|---|
| CF plasma experiment | | | |
| Experiment 1 | | | |
| CF1 Plasma (control) | 1 | 6.23 | |
| CF1 Plasma + CF BALF* | 1 | 16.00 | 256.9 |
| CF1 Plasma (control) | 1.25 | 16.27 | |
| CF1 Plasma + CF BALF* | 1.25 | 25.17 | 154.7 |
| CF1 Plasma (control) | 2.5 | 38.28 | |
| CF1 Plasma + CF BALF* | 2.5 | 39.66 | 103.6 |
| Experiment 2 | | | |
| CF2 Plasma (control) | 1 | 5.16 | |
| CF2 Plasma + CF BALF* | 1 | 11.16 | 216.3 |
| CF1 Plasma (control) | 1.5 | 7.86 | |
| CF1 Plasma + CF BALF* | 1.5 | 11.88 | 151.1 |
| CF1 Plasma (control) | 1.5 | 9.10 | |
| CF1 Plasma + CF BALF* | 1.5 | 12.88 | 141.5 |
| CF3 Plasma (control) | 1.5 | 8.39 | |
| CF3 Plasma + CF BALF* | 1.5 | 12.0 | 143.0 |
| NV plasma | | | |
| Plasma (control) | 1 | 6.68 | |
| Plasma + CF BALF* | 1 | 7.52 | 112.6 |
| Plasma (control) | 1.5 | 15.34 | |
| Plasma + CF BALF* | 1.5 | 14.31 | 93.3 |
| Plasma (control) | 2.5 | 44.22 | |
| Plasma + CF BALF* | 2.5 | 45.90 | 125.3 |

*Heat-treated CF BALF with 100 µg protein.

The PLA$_2$ in the CF plasma stimulated by CF BALF was probably the secretory PLA$_2$-IIA, a subform of PLA$_2$ whose level increases in the circulating blood of patients with inflammatory diseases. Because PLA$_2$-IIA is enriched in rheumatoid arthritis synovial fluid (12, 13), we further tested the effect of CF BALF on synovial fluid PLA$_2$ activity using the fluorescent method. When the fluorescent assay was carried out at 37° C., synovial fluid also increased TFI value in a dose-dependent manner (Table 4). Similar to that observed with plasma, CF BALF stimulated synovial fluid PLA$_2$ activity and the stimulation decreased with increasing synovial fluid volume (Table 4).

TABLE 4

Fluorescent assay of endogenous PLA$_2$ activity in synovial fluid and effect of CF BALF.
The reaction mixture contained 27.3 nmol PC-PG (50%-50%) UL labeled with Bis-BODIPY FL C$_{11}$-PC, 10 mM CaCl$_2$ in 3 ml 0.01 M Tris-HCl, pH 7.4 under conditions described in the Table. The assay was conducted at 37° C. for 2 min.[a]

| Conditions | SF quantity | PLA$_2$ activity (TFI) | % Of control |
|---|---|---|---|
| Synovial fluid (control) | 12.5 µl | 18.62 | |
| | 12.5 µl | 18.05 | |
| | 12.5 µl | 17.41 | |
| Synovial fluid + BALF[b] | 12.5 µl | 30.22 | 167.6 |
| | 12.5 µl | 22.80 | 126.5 |
| | 12.5 µl | 28.38 | 157.4 |

TABLE 4-continued

Fluorescent assay of endogenous PLA$_2$ activity in synovial fluid and effect of CF BALF.
The reaction mixture contained 27.3 nmol PC-PG (50%-50%) UL labeled with Bis-BODIPY FL C$_{11}$-PC, 10 mM CaCl$_2$ in 3 ml 0.01 M Tris-HCl, pH 7.4 under conditions described in the Table. The assay was conducted at 37° C. for 2 min.[a]

| Conditions | SF quantity | PLA$_2$ activity (TFI) | % Of control |
|---|---|---|---|
| Synovial fluid (control) | 25 µl | 21.76 | |
| Synovial fluid + BALF[b] | 25 µl | 34.32 | 157.8 |
| Synovial fluid (control) | 50 µl | 36.64 | |
| Synovial fluid + BALF[b] | 50 µl | 44.71 | 122.0 |

[a]The reaction mixture temperature was equilibrated to 37° C. prior to addition of synovial fluid or PLA$_2$.
[b]Heat-treated CF BALF with 100 µg protein.

Because the catalytic activities of all secreted PLA$_2$ enzymes in vitro are alike, apparently the CF BALF stimulated the secretory PLA$_2$ activity including the pancreatic PLA$_2$ (PLA$_2$-IB) and PLA$_2$-IIA. For convenience, we used the commercially available porcine pancreatic PLA$_2$ as the enzyme source in this study.

Radioactively labeled PMN assay: To investigate whether the effects of CF BALF and plasma on PLA$_2$ are biologically significant, we conducted experiments using $^3$H-phospholipid labeled PMN as substrate, instead of liposomes, to test the effects of CF BALF and plasma on PLA$_2$ activity. We observed that after overnight incubation of PMN with $^3$H-AA in the culture medium, over 80% of total radioactivity (2.17× 10$^4$ CPM) in the lipid fraction was associated with PC. We determined CPM of lysoPC representing hydrolysis of PC catalyzed by PLA$_2$. The results showed that PLA$_2$ alone did not significantly hydrolyze PMN phospholipids (Table 5). However, in the presence of CF BALF, PLA$_2$ hydrolyzed PMN PC. We also observed that in the presence of NV plasma, PLA$_2$ did not hydrolyze PMN PC, but CF plasma significantly induced PC hydrolysis catalyzed by PLA$_2$. These results suggest the biological importance of the stimulation of PLA$_2$ by CF BALF and plasma. Isolation and identification of the factors in the CF BALF and plasma were attempted.

TABLE 5

Effects of BALF and plasma on neutrophil phospholipid degradation hydrolyzed by pancreatic PLA$_2$.
Neutrophils isolated from normal volunteer peripheral blood were cultured in medium containing $^3$H-AA for 22 hours. $^3$H-labeled PMNs were incubated in HBSS in conditions specified as follows.

| Experimental conditions | Lyso phospholipids (cpm) |
|---|---|
| PMN control | 2335.05 |
| PMN control | 1793.48 |
| PMN + CF BALF | 2242.45 |
| PMN + CF BALF | 3172.00 |
| PMN + PLA$_2$ | 1787.47 |
| PMN + PLA$_2$ | 1925.24 |
| PMN + CF BALF + PLA$_2$ | 4555.00 |
| PMN + CF BALF + PLA$_2$ | 3766.77 |
| PMN + NV plasma | 1682.84 |
| PMN + CF plasma | 1639.24 |
| PMN + NV plasma + PLA$_2$ | 1754.34 |
| PMN + CF plasma + PLA$_2$ | 3447.64 |

Isolation, characterization and identification of PLA$_2$-i and PLA$_2$-s from human serum and PLA$_2$-s from human BALF: Some of the results of isolation and identification of PLA$_2$-s in CF BALF that were presented in Example 2 are repeated in this example so that the properties of BALF PLA$_2$-s can be compared with that of serum PLA$_2$-s.

Figure 23:
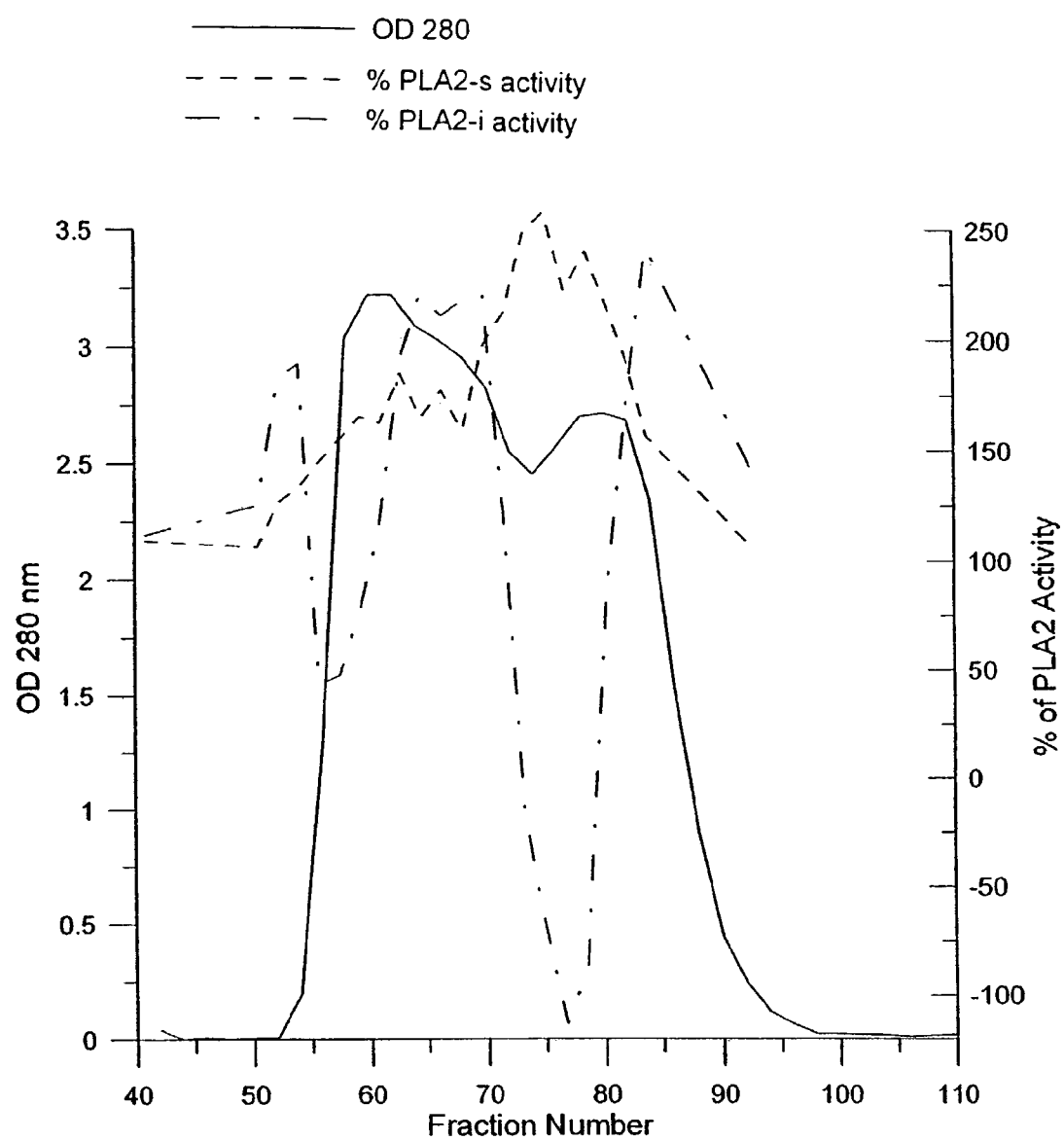
FIG. 23 shows gel filtration column chromatogram of serum. A total of 7 ml of serum from normal volunteers (NVs) was applied to a SEPHADEX G-100 column and serum components were eluted from column with Tris buffer as described in text. The amount of protein in fractions was determined by measuring the optical density at 280 nm; $PLA_2$-s and $PLA_2$-i activities were determined by the fluorescent assay and expressed as percentage of the control $PLA_2$ activity.

Gel filtration—After serum was applied to the SEPHADEX G100 column, most PLA$_2$-i and PLA$_2$-s activities were in fractions containing proteins in the range of molecular weights between 10 k-70 k (FIG. 23, Fractions #70-90). A small amount of PLA$_2$-i and PLA$_2$-s activities was found in fractions containing high molecular weight proteins (Fractions #54-67). The high molecular weight PLA$_2$-i and PLA$_2$-s was probably a product of protein aggregation. In this study we focused on the isolation of PLA$_2$-i and PLA$_2$-s in the low molecular weight fractions between #70 and #90.

Figure 24:
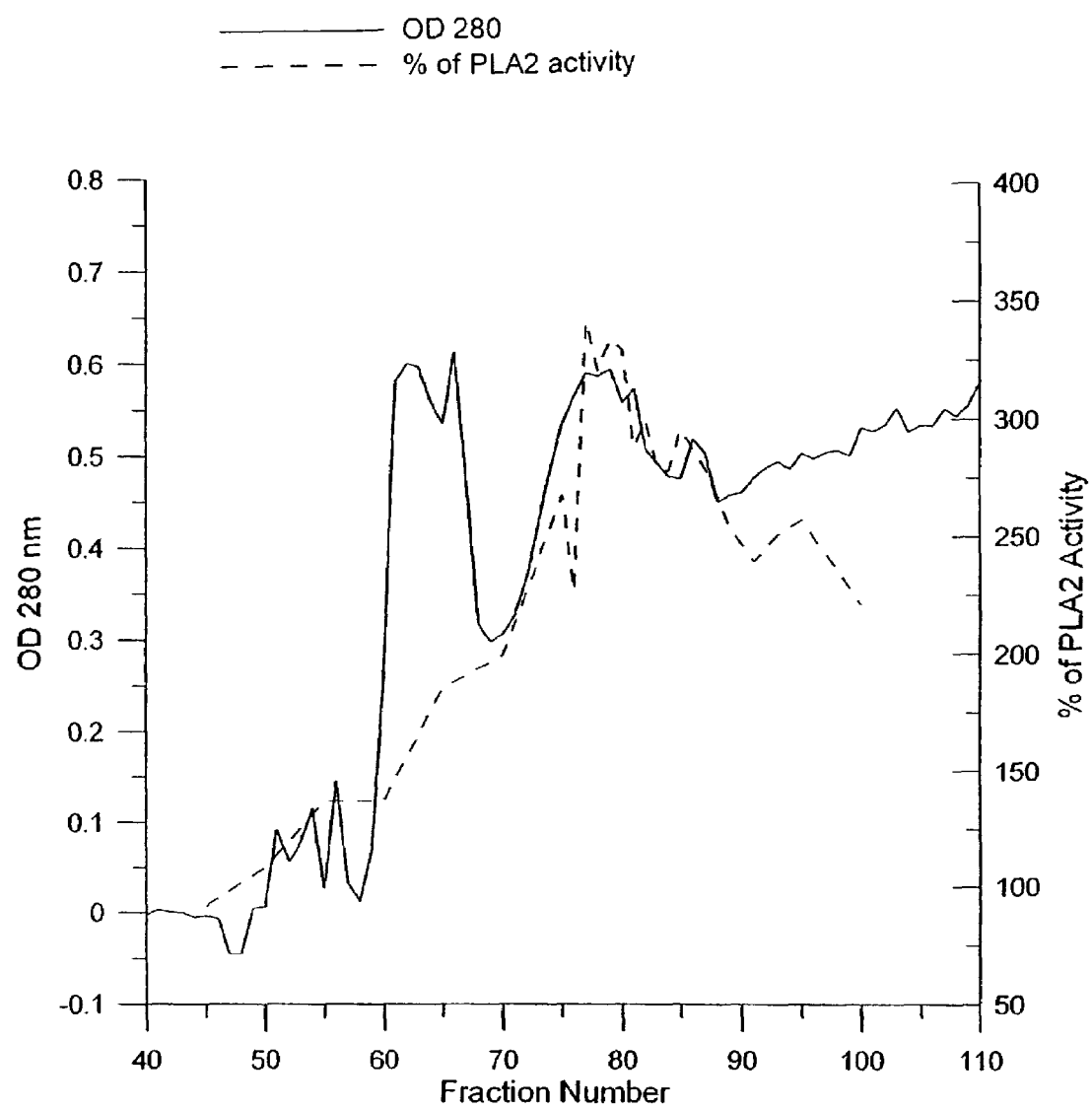
FIG. 24 shows gel filtration column chromatogram of heat-treated CF BALF. Protein and $PLA_2$-s activity in fractions were determined as described in FIG. 23.

After BALF proteins were eluted from Sephadex G100 column, the PLA$_2$-s activity was determined in the same number fractions as that of serum proteins (FIG. 24). No PLA$_2$-i activity was determined in all fractions.

Figure 25:
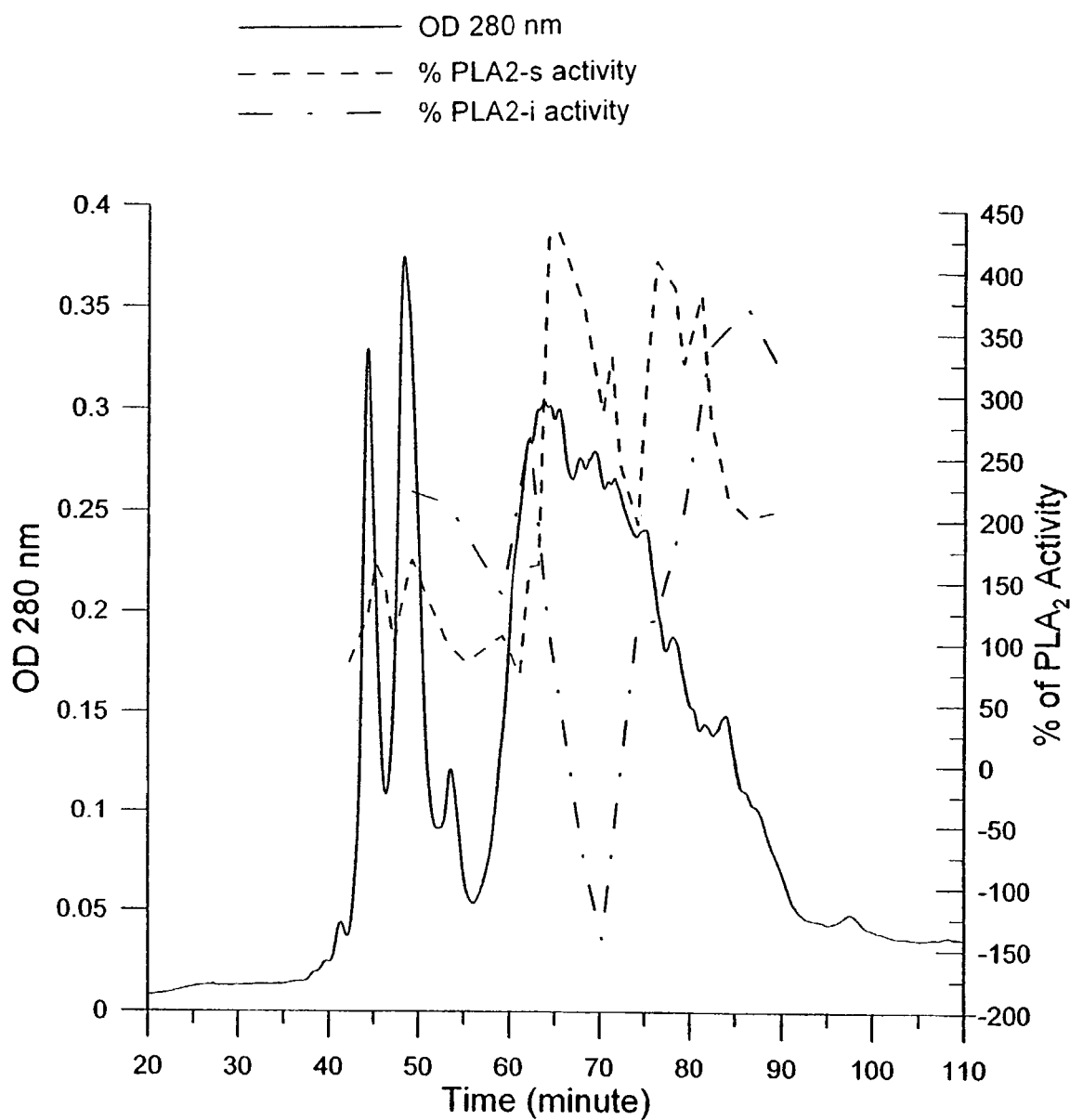
FIG. 25 shows HPLC anionic exchange column chromatogram of serum protein. The serum proteins were partially purified from gel filtration column chromatography (FIG. 23) and the proteins were applied to an HPLC MonoQ anionic exchange column and eluted with Tris buffer with NaCl salt gradient as described in text. Protein and $PLA_2$-i and $PLA_2$-s activities were determined as described in FIG. 23.

Anionic exchange HPLC—After the serum protein fractions collected from SEPHADEX G100 column were applied to the anionic exchange MonoQ column, most PLA$_2$-I and PLA$_2$-s activities were found in the fractions eluted between 0.07 M and 0.17 M NaCl gradient (between 60 to 90 min elution time) (FIG. 25). The protein profile in these fractions had a broad multiple protein peaks that overlapped one another. The PLA$_2$-i activity was more narrowly concentrated in fractions between 65 and 75 min elution time than PLA$_2$-s. Up till this step, PLA$_2$-i and PLA$_2$-s were not separable by the methods of column chromatography described. The next step we employed the reverse phase HPLC Vydac C4 column to isolate PLA$_2$-i and PLA$_2$-s. The fractions eluted between 60 and 90 min from MonoQ column were divided into four groups with each group having the same number of fractions in consecutive order. The fractions of each group were pooled, concentrated, and equilibrated in 0.01 M Tris-HCl buffer (pH 7.4) for applying to the reverse phase HPLC.

Figure 26:
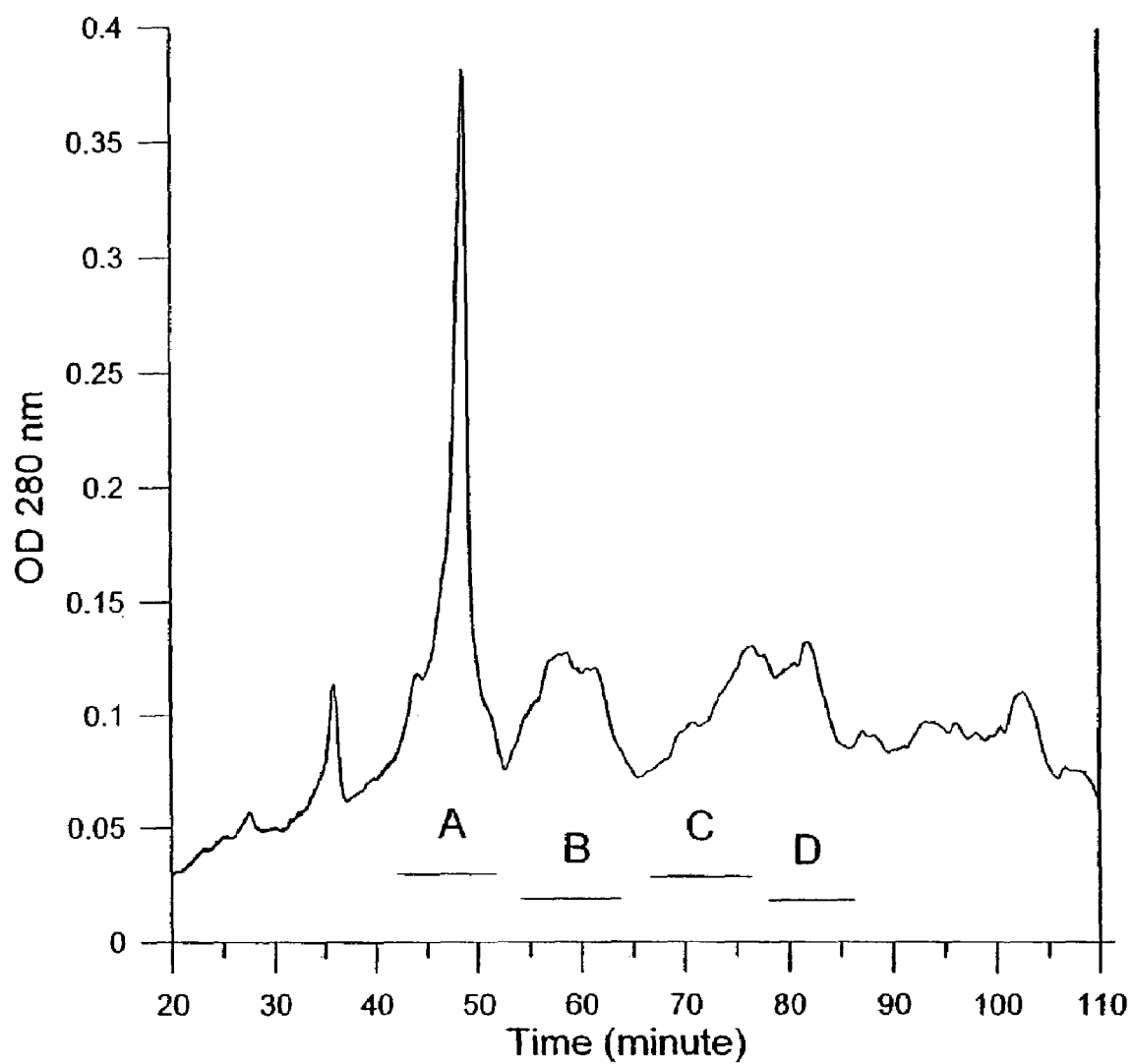
FIG. 26 shows HPLC anionic exchange column chromatogram of CF BALF proteins. The CF BALF proteins were partially purified from gel filtration column chromatography (FIG. 24) and the proteins were applied to an HPLC MonoQ anionic exchange column and eluted with Tris buffer with NaCl salt gradient as described in text. Protein and $PLA_2$-i and $PLA_2$-s activities were determined as described in FIG. 23.

The protein profile of BALF eluted from MonoQ column was different from the serum proteins (FIG. 26). Fractions between 42 and 87 min elution time were divided into four groups. Fractions of each group in successive order were pooled and concentrated as described above for reverse phase HPLC.

Figure 27:
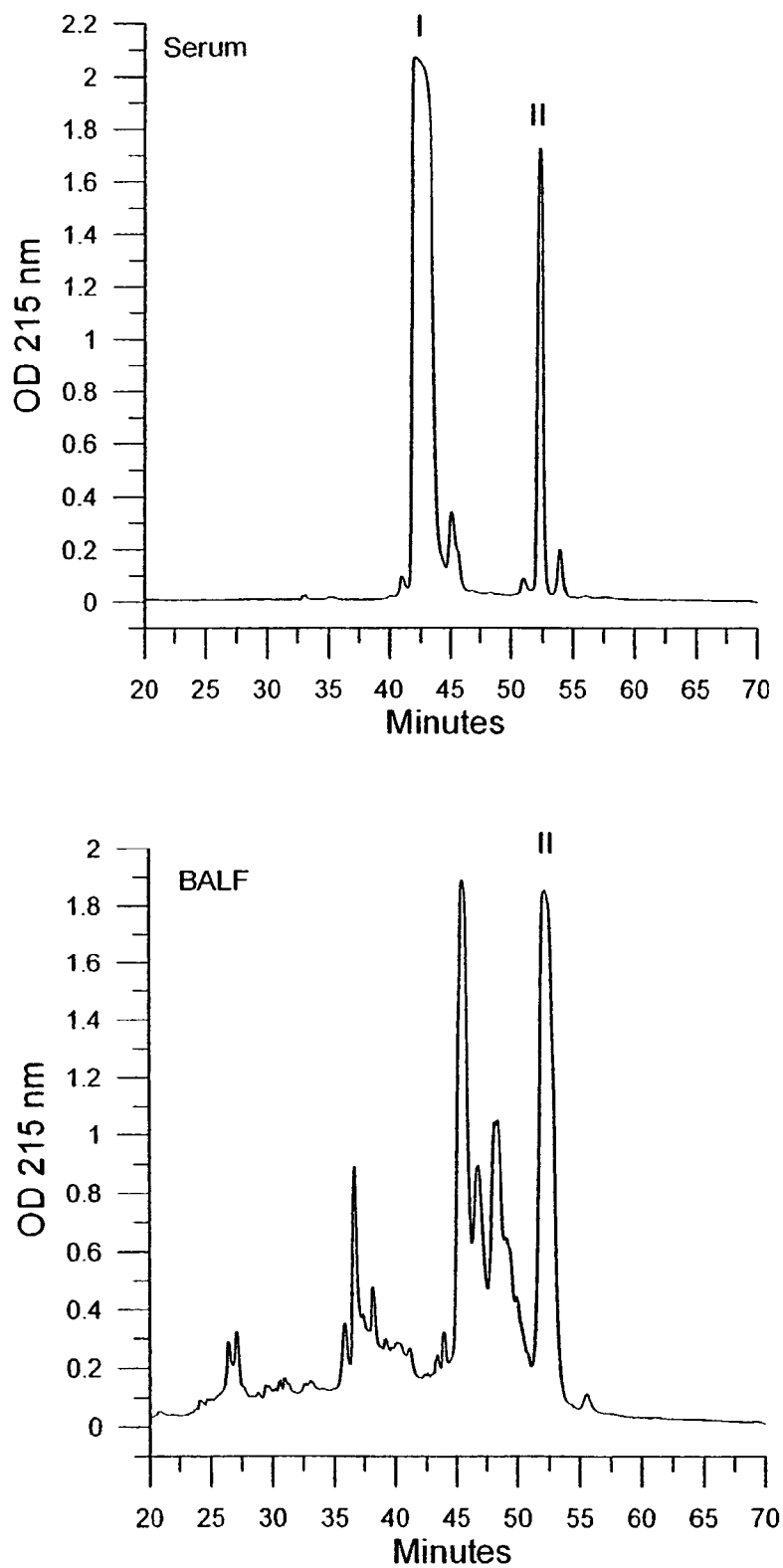
FIG. 27 shows HPLC reverse phase column chromatograms of serum protein and BALF protein. Both serum and BALF proteins were partially purified from MonoQ chromatography (FIGS. 25 and 26) and applied to the reverse phase HPLC. Protein I and Protein II represent the fractions that showed $PLA_2$-i activity and $PLA_2$-s activity, respectively.

Reverse phase HPLC—Two major protein peaks, namely protein-I and protein-II, were obtained from the reverse phase HPLC chromatograms of the serum samples (example shown in FIG. 27 top). The amount of serum Protein-II was about 3% of protein-I. Because the organic solvents used for the reverse phase HPLC interfered with the PLA$_2$ fluorescent assay, all protein fractions were re-equilibrated with 0.01 M Tris-HCl buffer, pH 7.4, and concentrated. Most BALF proteins were eluted from the column within the same time range of the serum proteins (FIG. 27 bottom).

Characterization of purified PLA$_2$-i and PLA$_2$-S: Both serum proteins I and II and BALF protein-II were highly purified as each of these proteins exhibited a single band on the SDS gel. The serum protein-I and protein-II had the same molecular weight around 52 kDa, whereas the BALF protein-II had an apparent molecular weight around 48 kDa.

Figure 28:
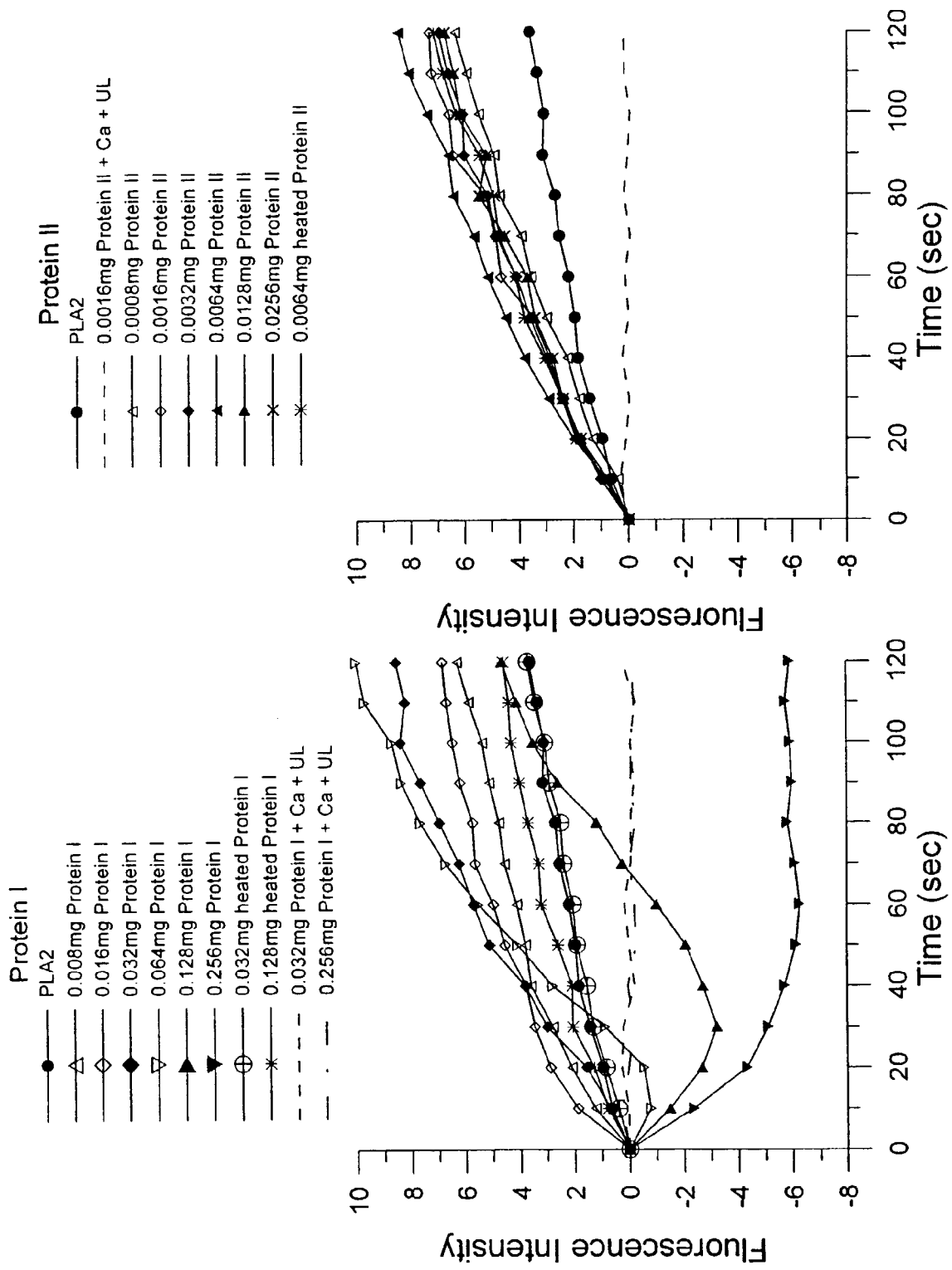
FIG. 28 shows effects of purified serum Protein I and Protein II on pancreatic $PLA_2$ activity using the fluorescent assay.
Figure 29:
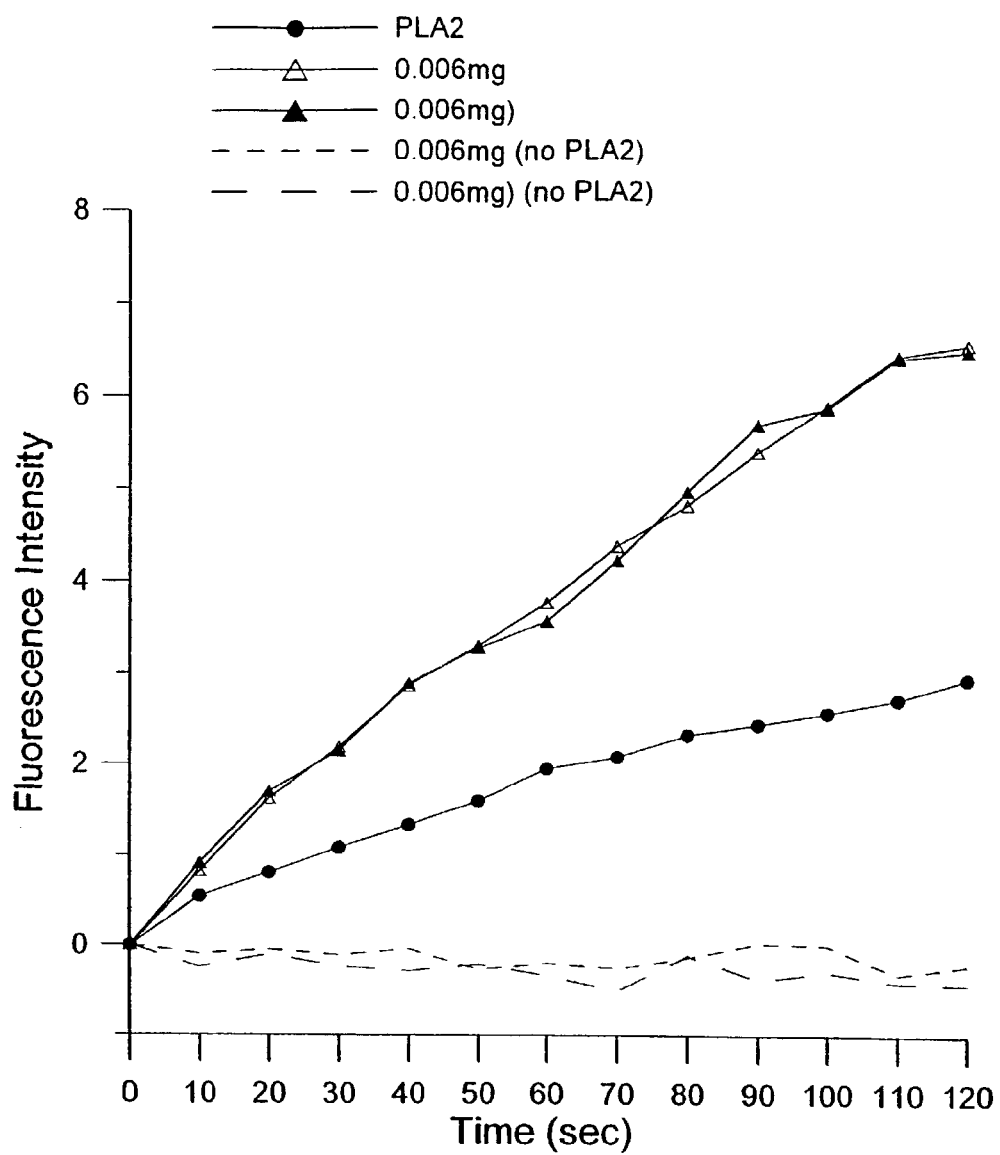
FIG. 29 shows effect of Protein II isolated from CF BALF using the fluorescent assay.

The fluorescent assay demonstrated that protein-I had both PLA$_2$-inhibiting and PLA$_2$-stimulating activities (FIG. 28). At low protein level (e.g., less than 30 µg), protein-I stimulated PLA$_2$. However, when the amount of protein increased to 60 to 100 µg, protein-I showed PLA$_2$ inhibitory activity in the beginning of the reaction and then showed PLA$_2$ stimulating activity. At high protein level (e.g., 256 µg), protein-I totally inhibited PLA$_2$ activity and reduced the fluorescence intensity far below the baseline (FIG. 28 left). Contrarily, protein-II at a wide range of protein concentrations exhibited only PLA$_2$-stimulating activity (FIG. 28 right). After treating the protein in boiling water for 5 min, protein-II lost less than 20% of its activity, whereas protein-I lost all of its stimulating and inhibiting activities. The activity properties of protein-I and protein-II were consistent with that observed with the plasma or serum as described above. Although protein-II isolated from BALF had lower molecular weight than the protein-II isolated from serum, it also exhibited PLA$_2$-s activity and was heat stable (FIG. 29). The purified serum PLA$_2$-s and BALF PLA$_2$-s had similar level of the PLA$_2$-stimulating activity at 6 µg protein in the assay. Thus, we concluded that protein-I was PLA$_2$-i and protein-II was PLA$_2$-s.

Structure determination and identification of PLA$_2$-i and PLA$_2$-s: The peptide amino acid sequences of trypsin-digested serum PLA$_2$-i and PLA$_2$-s and BALF PLA$_2$-s determined by mass spectrometry are shown in Table 6. Database search revealed that all determined serum PLA$_2$-i peptides matched human albumin and all determined serum PLA$_2$-s and BALF PLA$_2$-s peptides matched human α1-AT. This confirms that serum PLA$_2$-i was albumin and serum PLA$_2$-s was α1-AT. Because serum α1-AT had a molecular weight of 52 kDa and BALF PLA$_2$-s had a mass of 48 kDa, this suggests that BALF PLA$_2$-s was a truncated α1-AT. The cleavage site of α1-AT to form the truncated α1-AT in CF respiratory secretion had not been previously determined. In this invention we determined that the N-terminal sequence of the truncated α1-AT was HDQDHPTFNKIT, (SEQ. ID NO:23), indicating that α1-AT was cleaved between His15 and His16 bond in CF respiratory secretions. Because the truncated α1-AT molecular weight was 4 kDa less than α1-AT, this suggests that cleavage at the C-terminus must also occur, such as at the Pro357-Met358 bond (55-57).

TABLE 6

Results of tandem mass spectrometry (MS/MS) of trypsin in-gel digested PLA$_2$-i and PLA$_2$-s.

| Peptides | Observed m/z | Expected m/z | Calculated m/z | | |
|---|---|---|---|---|---|
| PLA$_2$-i from serum | | | | Human albumin peptides | |
| 1 | 302.18 | 301.18 | 303.15 | ER | |
| 2 | 508.24 | 507.23 | 507.24 | FGER | (SEQ ID NO:9) |
| 3 | 927.49 | 926.49 | 926.49 | YLYEIAR | (SEQ ID NO:10) |
| 4 | 100.61 | 999.61 | 999.60 | QTALVELVK | (SEQ ID NO: 11) |

TABLE 6-continued

Results of tandem mass spectrometry (MS/MS) of trypsin in-gel digested PLA$_2$-i and PLA$_2$-s.

| Peptides | Observed m/z | Expected m/z | Calculated m/z | | |
|---|---|---|---|---|---|
| 5 | 1149.63 | 1148.62 | 1148.61 | LVNEVTEFAK | (SEQ ID NO:12) |
| 6 | 671.82 | 1341.62 | 1341.63 | AVMDDFAAFVEK | (SEQ ID NO: 13) |
| 7 | 820.47 | 1638.92 | 1638.93 | KVPQVSTPTLVEVS | (SEQ ID NO:14) |
| 8 | 955.97 | 1909.93 | 1909.92 | RPCFSALEVDETYV | (SEQ ID NO:15) |
| 9 | 682.36 | 2044.07 | 2044.09 | VFDEFKPLVEEPQN | (SEQ ID NO:16) |
| PLA$_2$-s from serum | | | | Human alpha 1 -antitrypsin | |
| 1 | 474.26 | 473.26 | 473.28 | LVDK | (SEQ ID NO:17) |
| 2 | 532.24 | 531.23 | 531.27 | ELDR | (SEQ ID NO:18) |
| 3 | 605.27 | 604.28 | 604.31 | VPMMK | (SEQ ID NO:19) |
| 4 | 390.17 | 778.32 | 778.40 | SPLFMGK | (SEQ ID NO:20) |
| 5 | 504.7 | 1007.39 | 1007.49 | QINDYVEK | (SEQ ID NO:21) |
| 6 | 555.75 | 1109.48 | 1109.60 | LSITGTYDLK | (SEQ ID NO:4) |
| 7 | 601.93 | 1802.77 | 1802.95 | LQHLENELTHDIIT | (SEQ ID NO:22) |
| 8 | 917.88 | 1833.74 | 1832.92 | VFSNGADLSGVTEE | (SEQ ID NO:7) |
| 9 | 1288.09 | 2574017 | 2573.33 | TLNQPDSQLQLTTG | (SEQ ID NO:8) |
| PLA$_2$-s from BALF | | | | Human alpha 1-antitrypsin | |
| 1 | 686.44 | 685.43 | 685.44 | IVDLVK | (SEQ ID NO:2) |
| 2 | 538.8 | 1075.58 | 1075.61 | LSSWVLLMK | (SEQ ID NO:3) |
| 3 | 1110.62 | 1109.61 | 1109.60 | LSITGTYDLK | (SEQ ID NO:4) |
| 4 | 754.85 | 1507.69 | 1507.71 | GTEAAGAMFLEAIP | (SEQ ID NO:5) |
| 5 | 821.42 | 1640.83 | 1640.86 | ITPNLAEFAFSLYR | (SEQ ID NO:6) |
| 6 | 917.46 | 1832.90 | 1832.92 | VFSNGADLSGVTEE | (SEQ ID NO:7) |
| 7 | 858.77 | 2573.28 | 2573.33 | TLNQPDSQLQLTTG | (SEQ ID NO:8) |

Figure 30:
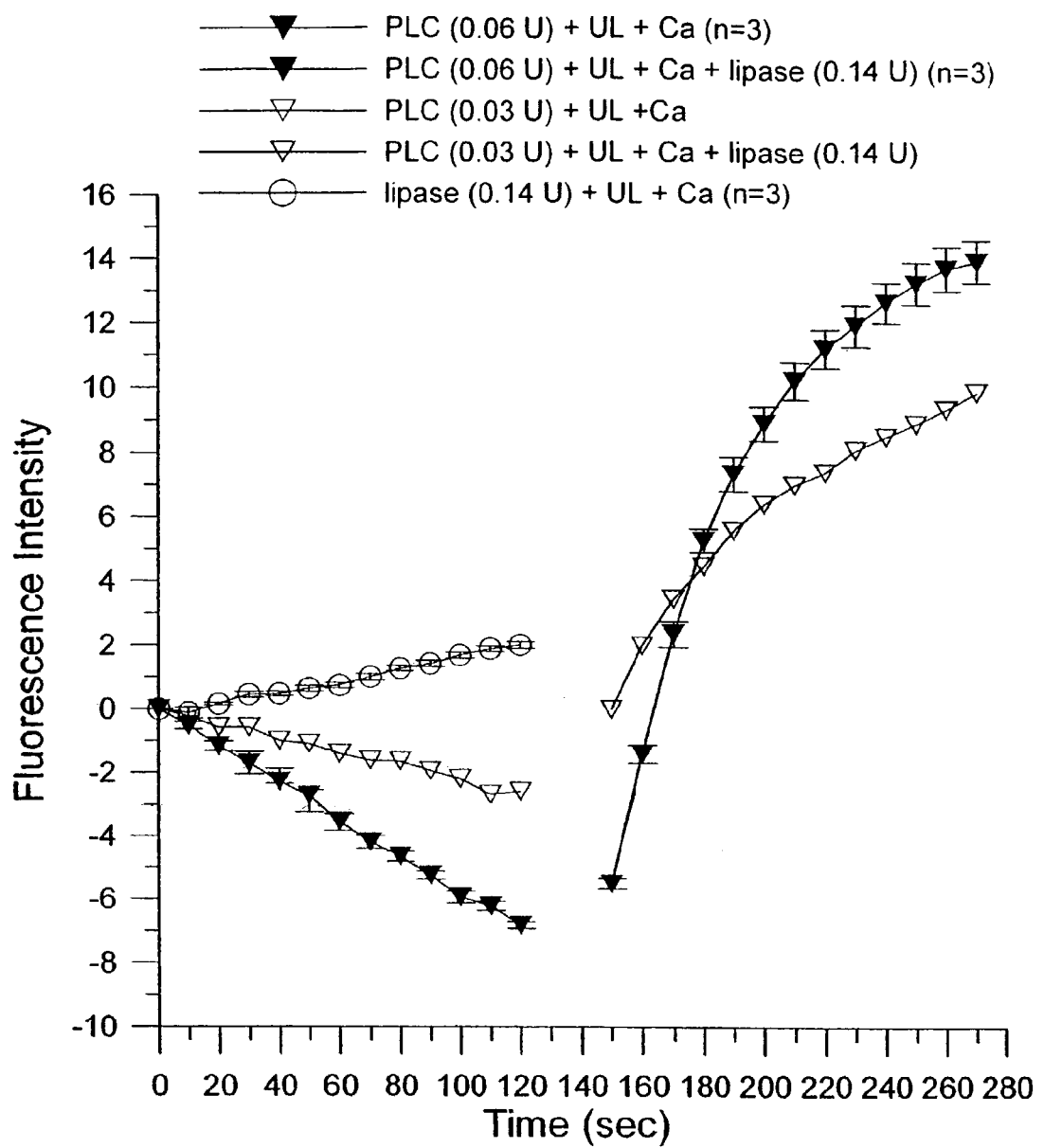
FIG. 30 shows results of a fluorescent assay of PLC and lipase. The PLC assay was the same as $PLA_2$ assay, except $PLA_2$ was replaced by PLC, and conducted at room temperature. PLC activity was determined for 2 min followed by adding an amount of lipase to the same reaction mixture and the fluorescent intensity was continuously determined for another 2 min.

Effects of PLA$_2$-s and PLA$_2$-i on PLC activity: It has been shown that a number of proteins can stimulate PLA$_2$ activity by depleting product inhibition (44). As shown in Example 2, while CF BALF could stimulate pancreatic PLA$_2$ and bee venom PLA$_2$, it had little effect on snake venom PLA$_2$. This suggests that stimulation of pancreatic or bee venom PLA$_2$ by truncated α1-AT was not due to product inhibition depletion. We speculated that truncated α1-AT might interact with membrane phospholipid head group and enhance PLA$_2$ penetration. Unlike pancreatic and bee venom PLA$_2$, snake venom PLA$_2$ acts as a dimer that was probably not affected by truncated α1-AT-membrane interaction. To test this hypothesis, we tested the effect of intact and truncated α1-AT on PLC, an enzyme that cleaves the phosphate bond on phospholipids to yield diacylglycerol. We employed the fluorescent method to determine PLC activity. Unlike the PLA$_2$ reaction, the fluorescence intensity decreased in the presence of PLC in the reaction mixture and the decrease was PLC-dose dependent (FIG. 30). The decrease in fluorescence intensity was because of the release of more hydrophobic diacylglycerol from PC into the environment that caused fluorescence quenching. When pancreatic lipase was added to the reaction mixture after 2 min of PLC reaction, the fluorescence intensity markedly increased with time because of the hydrolysis of diacylglycrol and the release of fluorescent-labeled fatty acid (FIG. 30). In the absence of PLC in the reaction mixture, lipase only yielded a moderate increase in fluorescence intensity, presumably due to contamination of pancreatic PLA$_2$ in the commercial product.

Figure 31:
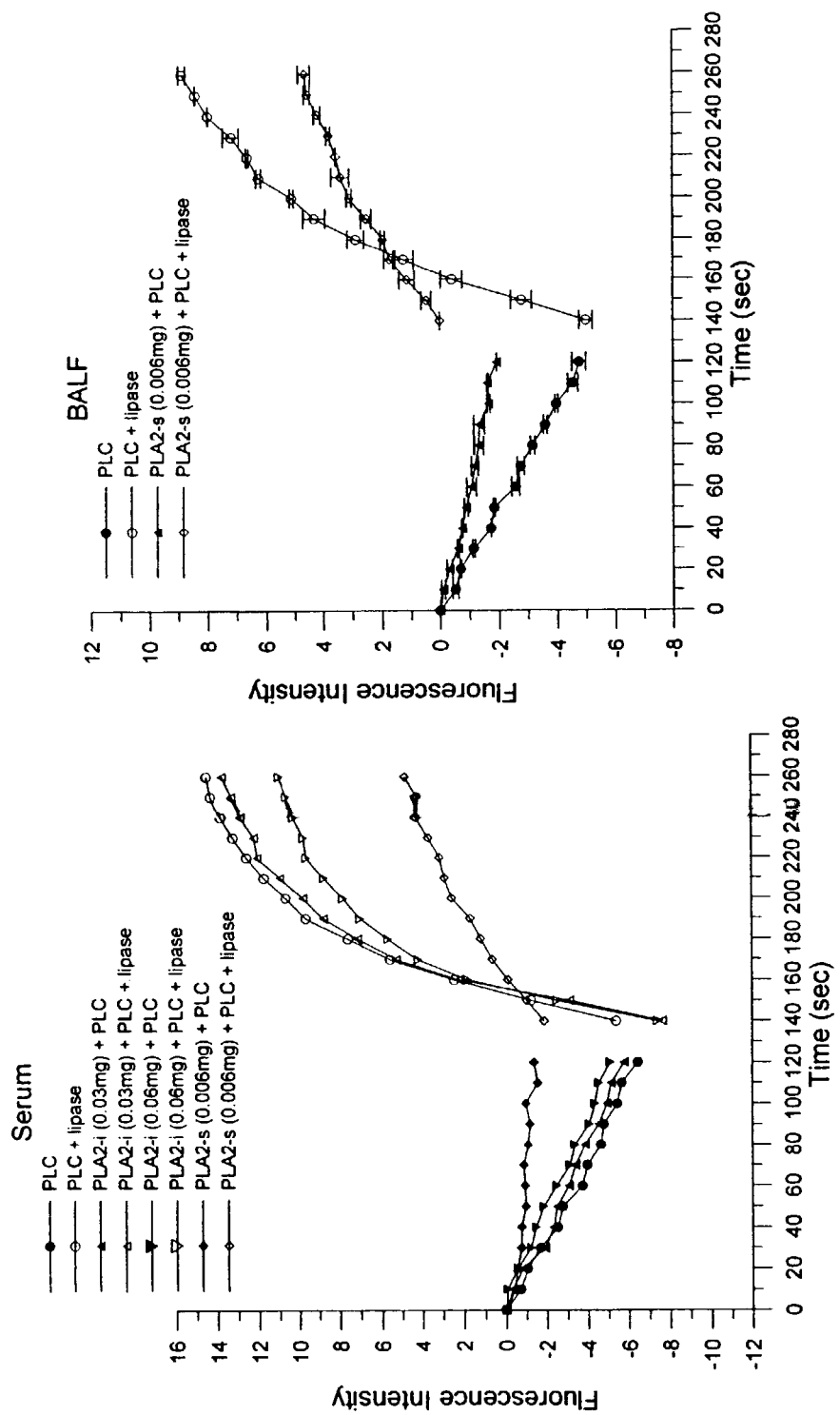
FIG. 31 shows effects of purified serum $PLA_2$-s and $PLA_2$-i and BALF $PLA_2$-s on PLC and lipase activities using the fluorescent assay.

Interestingly, the purified serum PLA$_2$-s (intact α1-AT) and BALF PLA$_2$-s (truncated α1-AT) effectively inhibited PLC activity, but they had no effect on the lipase activity (FIG. 31). However, an amount of serum PLA$_2$-i (albumin) that was 5 to 10-times more than PLA$_2$-s had little effect on the PLC activity.

Figure 32:
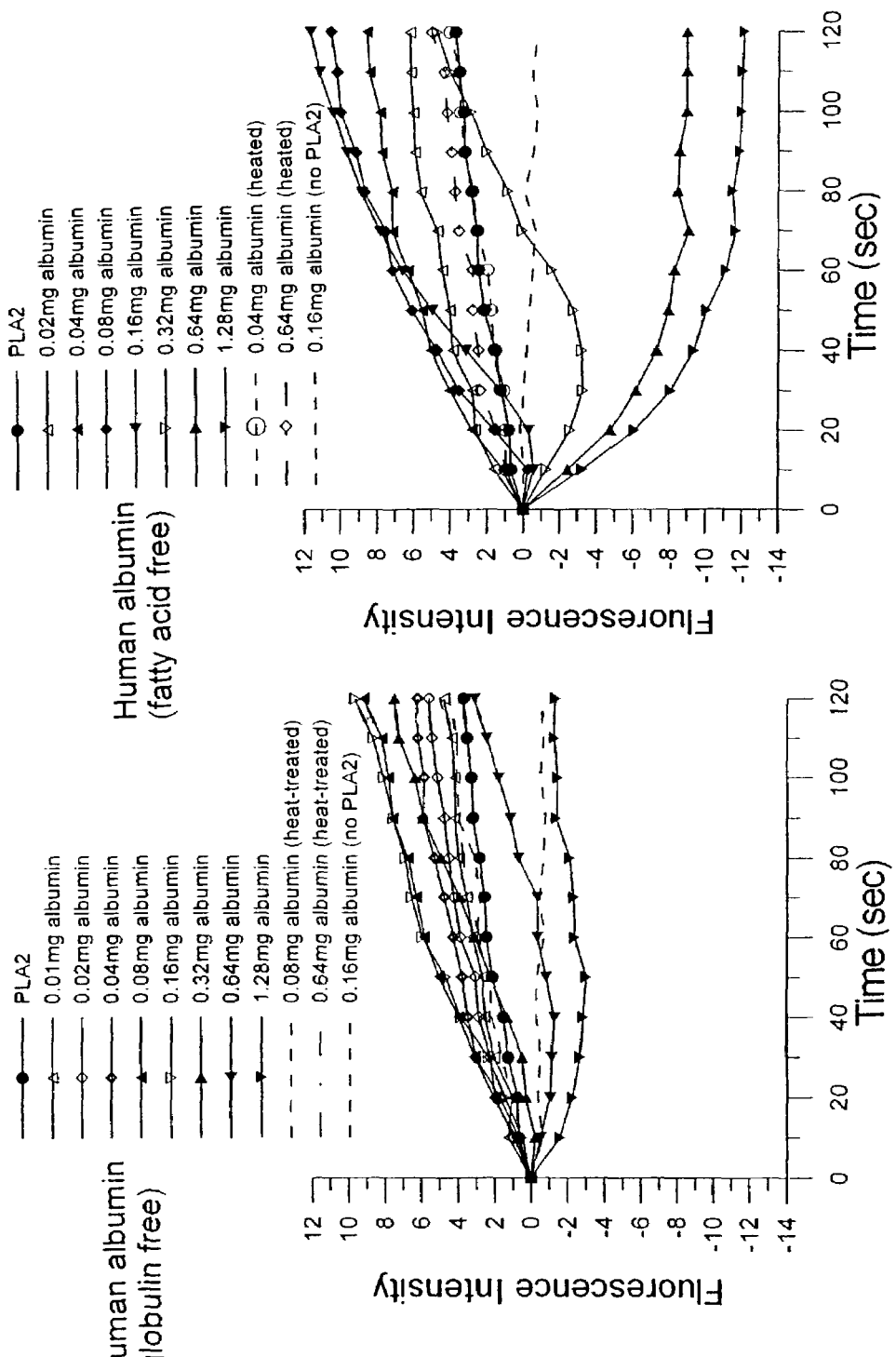
FIG. 32 shows results of a fluorescent assay using human serum albumin obtained from Sigma Chemical Co. Left: globulin-free albumin; Right: fatty acid-free albumin prepared from globulin-free product.

Effects of commercial products of human albumin and α1-AT on PLA$_2$ activity: Two different human serum albumin products, one globulin free (A8763) and one fatty acid free (A3782) were purchased from Sigma Chemical Co. The fatty acid-free albumin, as described in Sigma product information sheet, was prepared from globulin-free product. The fatty acid-free albumin exhibited the stimulating and inhibitory effects on PLA$_2$ similar to that shown by the purified PLA$_2$-i and plasma (FIG. 32 right). Although the globulin-free albumin stimulated PLA$_2$ similarly as the fatty acid-free albumin, it had much less PLA$_2$ inhibitory activity (FIG. 32 left). It appeared that more Sigma albumin was needed to display the effects on $PLA_2$ than the newly purified $PLA_2$-i. For example, Sigma fatty acid free albumin at 320 μg displayed similar inhibitory and stimulating effects as 128 μg of the newly isolated $PLA_2$-i. This was not due to impurity in Sigma protein because the Sigma albumin showed only a single protein band and migrated at the same distance as $PLA_2$-i on the SDS gel.

It is known for years that the broad protein peak of albumin as seen on anionic column chromatogram is a result of oxidation of the mercaptalbumin sulfhydryl group (47). It is interesting to note that $PLA_2$-s activity distributed along the broad protein peak, whereas $PLA_2$-i activity was found mainly in the major protein peak (FIG. 25). The major protein peak is known to be the mercaptalbumin which has the lowest fatty acid content among other forms of albumin (47). This seems consistent with the results that the commercial product of fatty acid-free albumin had much higher $PLA_2$-i activity than the globulin-free albumin (FIG. 32). Even the fatty acid-free albumin also has heterogeneous forms of albumin (47). This may explain that twice amount of commercial product of fatty acid-free albumin was required to reach the optimal $PLA_2$-i activity as compared to the purified $PLA_2$-i. These results imply that deficiency of $PLA_2$-i activity in albumin, such as resulted from oxidation or high content of fatty acid binding may impair its function as a regulator in $PLA_2$-mediated inflammation processes.

Figure 33:
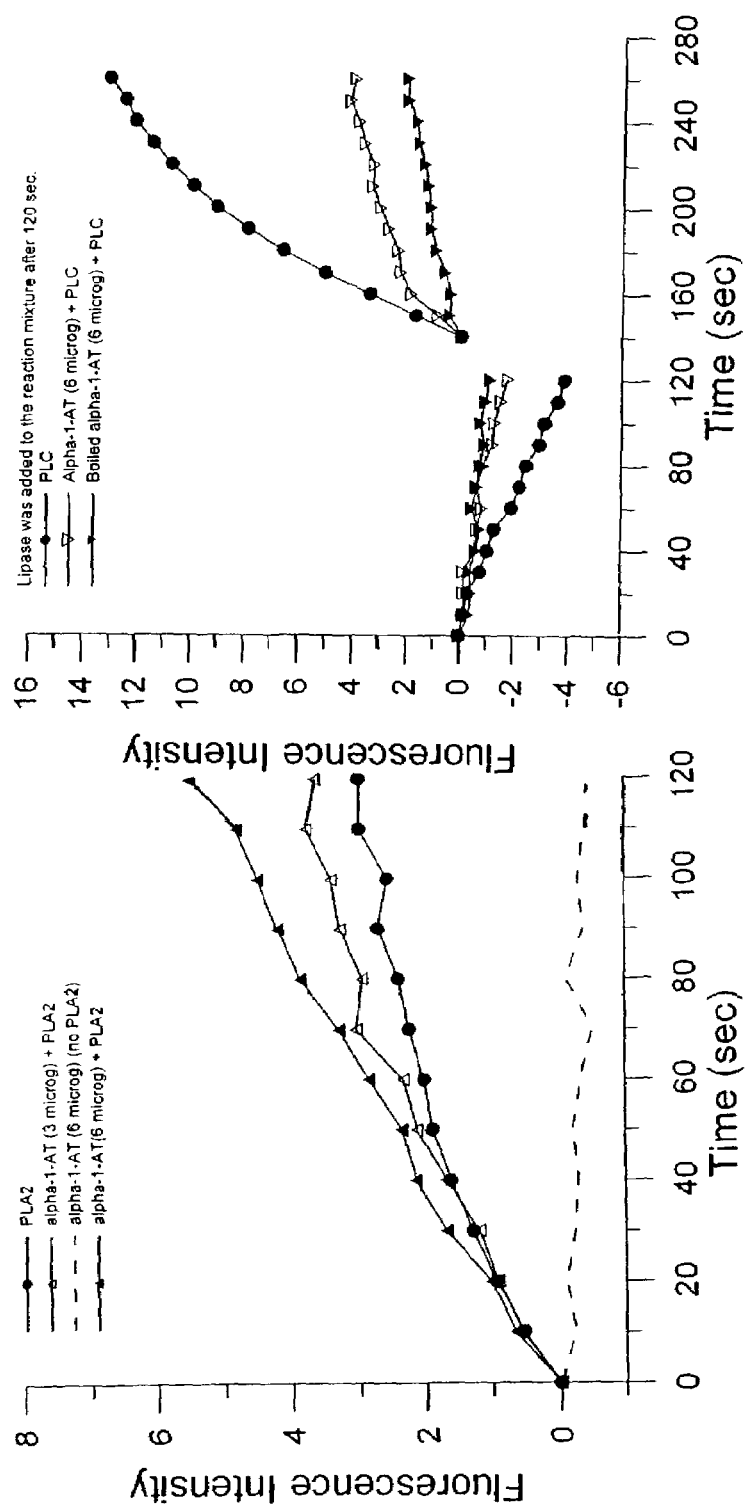
FIG. 33 shows effects of intact α1-AT on pancreatic $PLA_2$ activity (Left) and on PLC and lipase activities (Right) using the fluorescent assay.

Human serum α1-AT was obtained from Sigma Chemical Co. and it stimulated $PLA_2$ activity and inhibited PLC activity similar to that displayed by the purified serum and BALF $PLA_2$-s (FIG. 33). In addition, the $PLA_2$-stimulating activity and PLC-inhibiting activity (FIG. 33 right) of the commercial product of α1-AT was not affected by heating the protein in boiling water for 5 min.

Figure 34:
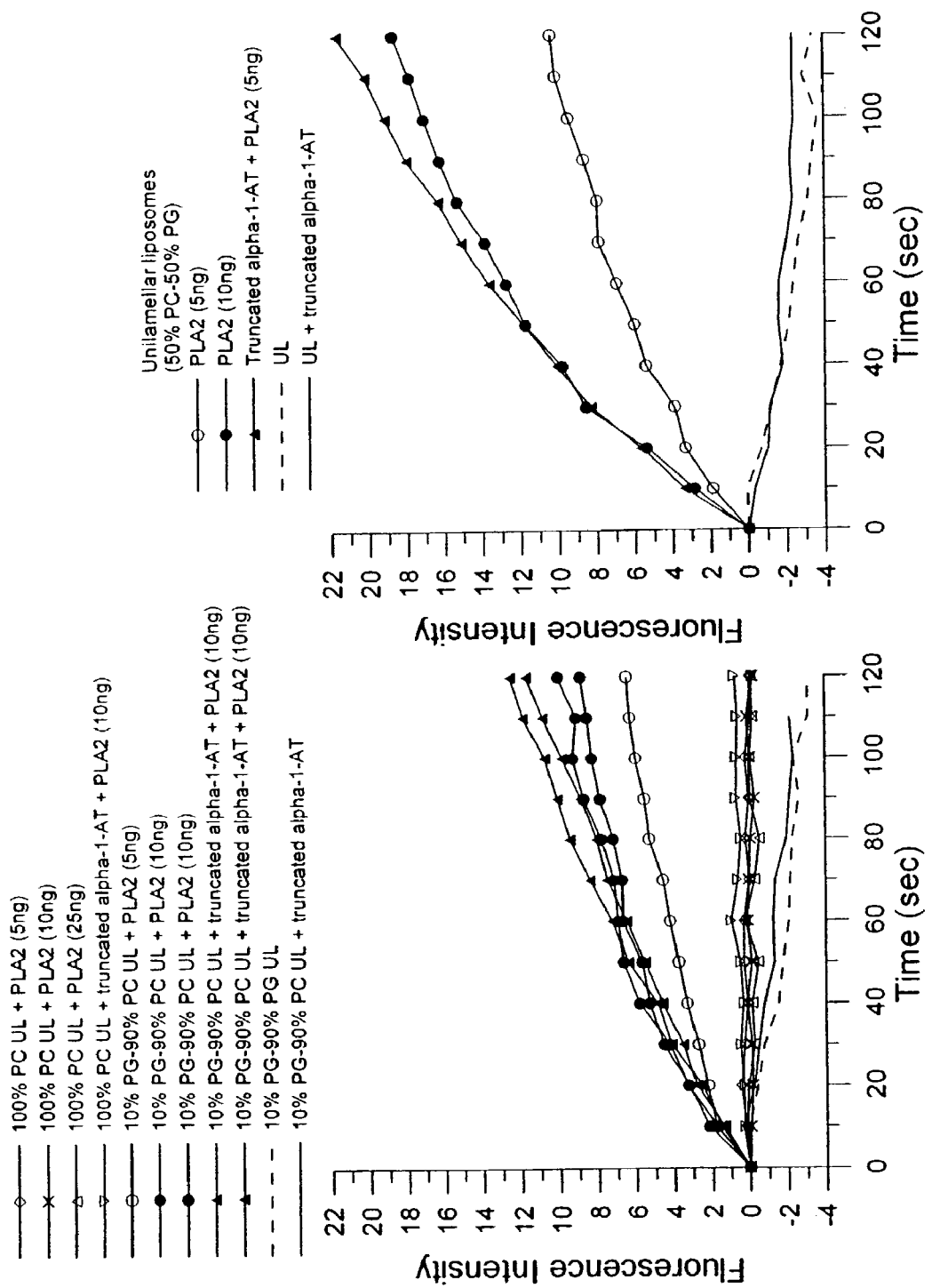
FIG. 34 shows effects of truncated α1-AT on $PLA_2$ with different charged unilamellar liposomes (UL) using the fluorescent assay. The assay was conducted at 37° C. The amount of truncated α1-AT was 6 μg.

Effects of phospholipid membrane charge on $PLA_2$ stimulation by truncated α1-AT: To determine whether stimulation of $PLA_2$ by truncated α1-AT was phospholipid charge dependent, we prepared three different groups of liposomes: 100% PC liposomes, 90% PC-10% PG liposomes, and 50% PC-50% PG liposomes. In the $PLA_2$ fluorescent assay we used each of these groups of liposome as substrate and test the effects of truncated α1-AT on $PLA_2$ activity. The results showed that $PLA_2$ did not hydrolyze 100% PC liposome phospholipid (e.g., no fluorescence intensity increase) even at 37° C.; truncated α1-AT also did not stimulate $PLA_2$ activity (FIG. 34 left). Using 90% PC-10% PG liposome as substrate, $PLA_2$ increased fluorescence intensity in a $PLA_2$-dose dependent manner, but the presence of truncated α1-AT did not significantly enhance the $PLA_2$ activity (FIG. 34 left). However, with 50% PC-50% PG liposome as substrate, $PLA_2$ not only exhibited an enzyme dose-dependent activity, its activity was two-times higher than that with 90% PC-10% PG liposomes (FIG. 34 right). Also, with 50% PC-50% PG liposome as substrate, $PLA_2$ activity was markedly stimulated by truncated α1-AT (FIG. 34 right).

Effect of mixing lysoPC and truncated α1-AT or intact α1-AT on $PLA_2$ activity was also determined by the fluorescent assay. The reaction mixture containing 27.3 nmol UL, 10 mM $Ca^{2+}$ in the absence or presence of specified amount of egg yolk lysoPC, truncated α1-AT, intact α1-AT, or human serum albumin in 3 ml Tris buffer (pH 7.4) was incubated at 37° C. for 2 min followed by addition of 5 ng $PLA_2$. Reaction was continued at 37° C. for 2 min. Total fluorescence intensity (TFI) within 2 min was determined as described in the materials and methods section. As shown in Table 7, pre-incubation of truncated or intact α1-AT with lysoPC, a $PLA_2$ product that causes fluorescence intensity increase in the fluorescent assay, had little effect on $PLA_2$-stimulating effect.

TABLE 7

Effect of mixing lysoPC and truncated α1-AT or intact α1-AT on $PLA_2$ activity determined by the fluorescent assay.

| Experimental condition | TFI | % of control |
|---|---|---|
| $PLA_2$ (5 ng) (control) | 37.62 | 100 |
| Truncated α1-AT (6 μg, 0.12 nmol) + $PLA_2$ (5 ng) | 57.23 | 152.1 |
| Intact α1-AT (20 μg, 0.38 nmol) + $PLA_2$ (5 ng) | 68.96 | 183.3 |
| LysoPC (9 nmol) + $PLA_2$ (5 ng) (control) | 19.70 | 100 |
| LysoPC (9 nmol) + Truncated α1-AT (6 μg, 0.12 nmol) + $PLA_2$ (5 ng) | 31.82 | 161.6 |
| LysoPC (9 nmol) + Intact α1-AT (20 μg, 0.38 nmol) + $PLA_2$ (5 nmol) | 29.81 | 151.4 |
| $PLA_2$ (5 ng) (control) | 47.43 | 100 |
| Albumin (20 μg, 0.32 nmol) + $PLA_2$ (5 ng) | 66.20 | 139.6 |
| LysoPC (9 nmol) + $PLA_2$ (5 ng) (control) | 40.68 | 100 |
| LysoPC (9 nmol) + Albumin (20 μg, 0.32 nmol) + $PLA_2$ (5 ng) | 46.01 | 113.1 |
| $PLA_2$ (5 ng) (control) | 24.23 | 100 |
| Albumin (20 μg, 0.32 nmol) + $PLA_2$ (5 ng) | 48.19 | 198.9 |
| LysoPC (9 nmol) + $PLA_2$ (5 ng) (control) | 23.75 | 100 |
| LysoPC (9 nmol) + Albumin (20 μg, 0.32 nmol) + $PLA_2$ (5 ng) | 35.91 | 151.2 |

Figure 35:
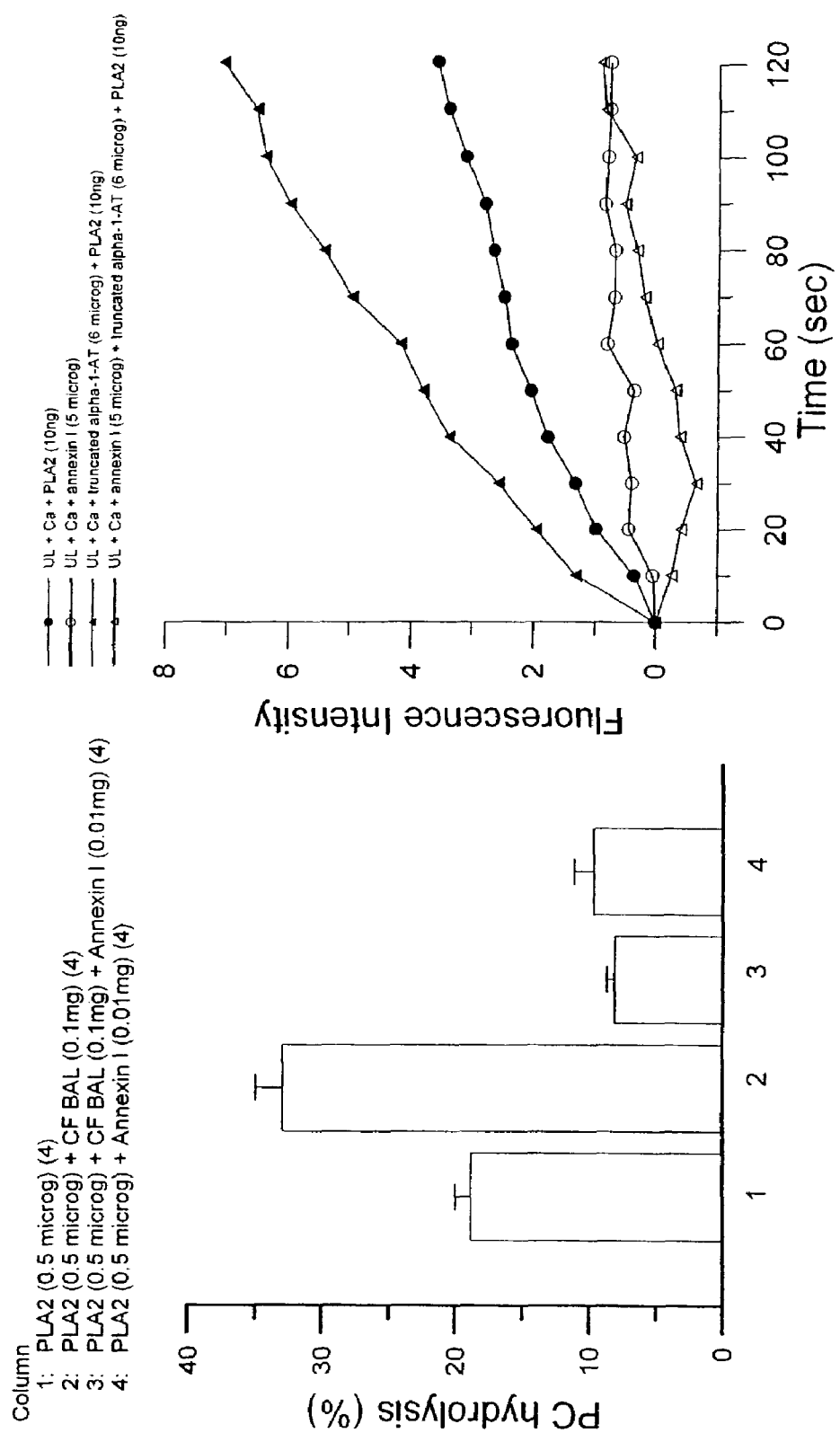
FIG. 35 shows effects of annexins on $PLA_2$ and BALF $PLA_2$-s activities. Left: Results of the effects of annexins on CF BALF $PLA_2$-s activity was determined by the radioactive method shown in U.S. Pat. No. 6,180,596. Right: Effect of annexin on $PLA_2$-s activity of truncated α1-AT from CF BALF was determined by the fluorescent assay.

Inhibition of $PLA_2$ and truncated α1-AT activity by annexin: We previously described that lung annexins (annexin I and annexin VIII) inhibited $PLA_2$ activity and suppressed the stimulation of $PLA_2$ by CF BALF using radioactively labeled liposome method (37) (FIG. 35 left). Here, using the fluorescent assay we also demonstrated that annexin I markedly inhibited both $PLA_2$ activity and the effect of truncated α1-AT on $PLA_2$ stimulation (FIG. 35 right).

REFERENCES

1. Bulger E M, Maier R V. Lipid mediators in the pathophysiology of critical illness. Crit Care Med 2000; 28:N27-N36.
2. Funk C D. Prostaglandins and leukotrienes: Advances in eicosanoid biology. Science 2001; 294:1871-1875.
3. Griffiths R J. Prostaglandins and inflammation. In Inflammation: Basic Principles and Clinical Correlates, 3rd ed., J. I. Gallin and R. Snyderman, editors. Lippincott Williams & Wilkins, Philadelphia. 1999; 349-360.
4. Penrose J F., Austen K F, Lam B K. Leukotrienes: Biosynthetic pathways. Release, and receptor-mediated actions with relevance to disease states. In Inflammation: Basic Principles and Clinical Correlates, 3rd ed., J. I. Gallin and R. Snyderman, editors. Lippincott Williams & Wilkins, Philadelphia. 1999; 361-372.
5. Cummings B S, McHowat J, Schnellmann R G. Phospholipase A2s in cell injury and death. J Pharmacol Experi Therap 2000; 294:793-799.
6. Vadas P, Browning J, Edelson J, Pruzanski W. Extracellular phospholipase A2 expression and inflammation: the relationship with associated disease states. J Lipids Mediat 1993; 8:1-30.
7. Murakami M, Nakatani Y, Atsumi G, Inoue K, Kudo I. Regulatory functions of phospholipase A2. Crit Rev Immunol 1997; 17:225-284.
8. Murakami M, Kudo I. Phospholipase A2. J Biochem 2002; 131:285-292.
9. Balsinde J, Balboa M A, Insel P A, Dennis E A. Regulation and inhibition of phospholipase A2. Annu Rev Pharmacol Toxicol 1999; 39:175-189.

10. Valentin E, Lambeau G. Increasing molecular diversity of secreted phospholipases A2 and their receptors and binding proteins. Biochim Biophys Acta 2000; 1488:59-70.
11. Vadas P, Pruzanski W. Phospholipase A2 activation is the pivotal step in the effector pathway of inflammation. In: Phospholipase A2, ed. By Wong P Y K, Dennis E A. Plenum Press, New York 1990; p.83-101.
12. Lai C Y, Wada K. Phospholipase A2 from human synovial fluid: purification and structural homology to the placental enzyme. Biochem Biophys Res Comm 1988; 167:488-493.
13. Kramer R M, Hession C, Johansen B, Hayes G, McGray P, Chow E P, Tizard R, Pepinsky R B. Structure and properties of a human non-pancreatic phospholipase A2. J Biol Chem 1989; 264:5768-5775.
14. Seilhamer J J, Pruzanski W, Vadas P, Plant S, Miller J A, Kloss J, Johnson L K. Cloning and recombinant expression of phospholipase A2 present in rheumatoid arthritic synovial fluid. J Biol Chem 1989; 264:5335-5338.
15. Dessen A. Structure and mechanism of human cytosolic phospholipase A2. Biochim Biophys Acta 2000; 1488:40-47.
16. Sapirstein A, Bonventre J V. Specific physiological roles of cytosolic phsopholipase A2 as defined by gene knockouts. Biochim Biophys Acta 2000; 1488:139-148.
17. Nevalainen T J, Haapamaki M M, Gronroos J M. Roles of secretory phospholipases A2 in inflammatory diseases and trauma. Biochim Biophys Acta 2000; 1488:83-90.
18. Buckland A G, Wilton D C. The antibacterial properties of secreted phospholipases A2. Biochim Biophys Acta 2000; 1488:71-82.
19. Seilhamer J J, Randall T L, Yamanaka M, Johnson L K. Pancreatic phospholipase A2: Isolation of human gene and cDNAs from porcine pancreas and human lung. DNA 1986; 5:519-527.
20. Sakata T, Nakamura E, Tsuruta Y, Tamaki M, Teraoka H, Tojo H, Ono T, Okamoto M. Presence of pancreatic-type phospholipase A2 mRNA in rat gastric mucosa and lung. Biochim Biophys Acta 1989; 1007:124-126.
21. Lindahl M, von Schenck H, Tagesson C. Isolation and characterization of phospholipase A2 from rat lung with affinity chromatography and two-dimensional gel electrophoresis. Biochim Biophys Acta 1989; 1005:282-288.
22. Calabrese C, Triggiani M, Marone G, Mazzarella G. Arachidonic acid metabolism in inflammatory cells of patients with bronchial asthma. Allergy 2000; 55 Sppl 61:27-30.
23. Cho W. Structure, function, and regulation of group V phospholipase A2. Biochim Biophys Acta 2000; 1488:48-58.
24. Koduri R S, Baker S F, Snitko Y, Han S K, Cho W, Wilton D C, Gelb M H. Action of human group Iia secreted phospholipase A2 on cell membrane. J Biol Chem 1998; 273:32142-32153.
25. Yedgar S, Lichtenberg D, Schnitzer E. Inhibition of pgospholipase A2 as a therapeutic target. Biochim Biophys Acta 2000; 1488:182-187.
26. Davis P B, Drumm M, Konstan M W. Cystic Fibrosis. Am J Respir Crit Care Med 1996, 154:1229-1256.
27. Barton A D, Ryder K, Lourenco R V, Dralle W, Weiss S G. Inflammatory reaction and airway damage to cystic fibrosis. J Lab Clin Med. 1976; 88:423-426.
28. Bruce M C, Poncz L, Klinger J D, Stern R C, Tomashefski J F, Dearborn D G. Biochemical and pathological evidence for proteolytic destruction of lung connective tissue in cystic fibrosis. Am Rev Respir Dis. 1985; 132:529-535.
29. Crystal R G., Alpha 1-antitrypsin Deficiency. Biology, Pathogenesis, Clinical Manifestations, Therapy. Marcel Dekker, New York 1996.
30. Gilljam H, Strandvik B, Ellin A, Wiman L G. Increased mole fraction of arachidonic acid in bronchial phospholipids in patients with cystic fibrosis. Scan J Clin Lab Invest 1986; 46:511-518.
31. Miele L, Cordella-Miele E, Xing M, Frizzell R, Mukherjee A B. Cystic fibrosis gene mutation (DF508) is associated with an Intrinsic abnormality in Ca2+-induced arachidonic acid release by epithelial cells. DNA Cell Biol 1997; 16:749-759.
32. Freedman S D, Katz M H, Parker E M, Laposata M, Urman M Y, Alvarez J G. A membrane lipid imbalance plays a role in the phenotypic expression of cystic fibrosis in cftr-/-mice. Proc Natl Acad Sci USA 1999; 96:13995-14000.
33. Doring G. Serine proteinase inhibitor therapy in a1-antitrypsin inhibitor deficiency and cystic fibrosis. Pediatr Pulmo 1999; 28:363-375.
34. Konstan M W, Walenga R W, Hilliard K A, Hilliard J B. Leukotriene B4 markedly elevated in the epithelial lining fluid of patients with cystic fibrosis. Am Rev Respir Dis 1993; 148:896-901.
35. Sampson A P, Spencer D A, Green C P, Piper P J, Price J F. Leukotrienes in the sputum and urine of cystic fibrosis. Br J Clin Pharmacol 1990; 30:861-869.
36. Zakrzewski J T, Barnes N C, Costello J F, Piper P J. Lipid mediators in cystic fibrosis and chronic obstructive pulmonary disease. Am Rev Respir Dis 1987; 136:779-782.
37. Tsao F H C. Methods of inhibiting phospholipase A2 and phospholipase A2 simulator activities. 2001; U.S. Pat. No. 6,180,596.
38. Crystal R G. α-1-Antitrypsin deficiency, emphysema, and liver disease. Genetic basis and strategies for therapy. J Clin Invest. 1990; 85:1343-1352.
39. Wong, P. Y. K., E. D. Dennis. 1990. Phospholipase A2: Role and Function in Inflammation, Plenum Press, NY, 1990.
40. Tsao F H C. Purification and characterization of two rabbit lung Ca2+-dependent phospholipid-binding proteins. Biochim Biophys Acta 1990; 1045:29-39
41. Lowry O H, Rosebrough N J, Farr A L, Randall R J. Protein measurement with the Folin phenol reagent. J Biol Chem 1951; 193:265-275.
42. Bligh E G, Dyer W J. A rapid method of total lipid extraction and purification. Can J Biochem Physiol 1955; 37:911-917.
43. Tsao F H C, Hull W M, Strickland M S, Whitsett J A, Foo T K F, Zografi G and DeLuca P M Jr. Lung calcium-dependent phospholipid-binding proteins: structure and function. Biochim. Biophys. Acta 1991;1081:141-150.
44. Conricode K M, Ochs R S. Mechanism for the inhibitory and stimulatory actions of proteins on the activity of phospholipase A2. Biochim Biophys Acta 1989; 1003:36-43.
45. Cantin A, Bilodeau G, Begin R. Granulocyte elastase-mediated proteolysis of alpha 1-antitrypsin in cystic fibrosis bronchopulmonary secretions. Pediatr Pulmon 1989; 7:12-17.
46. Reich, R, G. R. Martin, 1996. Prostaglandins 51, 1-17.
47. Noel J K F, Hunter M J. Bovine mercaptalbumin and non-mercaptalbumin monomers. Interconversions and structural differences. J Biol Chem 1972; 247:7391-7406.
48. Gerritsen, M. E. 1996. Physiological and pathophysiological roles of eicosanoids in the microcirculation. Cardiovasc Res. 32:720-732.

49. Kim, T. S., C. S. Sundaresh, S. I. Feinstein, C. Dodia, W. R. Skach, M. K. Jain, T. Nagase, N. Seki, K. I. Ishikawa, N. Nomura, A. B. Fisher. 1997. Identification of a human cDNA clone for lysosomal type Ca2+-independent phsopholipase A2 and properties of the expressed protein. J. Biol. Chem. 272:2542-2550.
50. Cantin A M, Lafrenaye S, Begin R O. Antineutrophil elastase activity in cystic fibrosis serum. Pediatr Pulmon 1991; 11:249-253.
51. Meshulam, T, H. Herscovitz, D. Casavant, J. Bernardo, R. Roman, R. P. Haugland, G. S. Strohmeier, R. D. Diamond, E. R. Simons. 1992. Flow cytometric kinetic measurements of neutrophil phospholipase A activation. J. Biol. Chem. 267:21465-21470.
52. Tsao F H C, Meyer K C, Chen X M, Rosenthal N S, Hu J P. Degradation of annexin I in bronchoalveolar lavage fluid in patients with cystic fibrosis. Am J Respir Cell Mol Biol 1998; 18:120-128.
53. Heinrikson R L, Kezdy F J. A novel bifunctional mechanism of surface recognition by phospholipase $A_2$. In "Biochemistry, Molecular Biology, and Physiology of Phospholipase A2 and Its Regulatory Factors", ed. Mukherjee A B. Plenum Press, New York, 1990; p.37-47.
54. Bezzine S, Koduri R S, Valentin E, Murakami M, Kudo I, Ghomashchi F, Sadilek M, Lambeau G, Gelb M H. Exogenously added human group X secreted phospholipase A(2) but not the group IB, IIA, and V enzymes efficiently release arachidonic acid from adherent mammalian cells. J. Biol. Chem. 2000; 275: 3179-91.
55. Moraga F, Lindgren S, Janciaskiene S. Effects of noninhibitory alpha-1-antitrypsin on primary human monocyte activation in vitro. Arch. Biochem. Biophys. 2001; 221-226.
56. Banda M J, Rice A G, Griffin G L, Senior R M. Alpha 1-proteinase inhibitor is a neutrophil chemoattractant after proteolytic inactivation by macrophage elastase. J. Biol. Chem. 1988; 263: 4481-4484.
57. Vissers M C, George P M, Bathurst I C, Brennan S O, Winterbourn C C. Cleavage and inactivation of alpha 1-antitrypsin by metalloproteinases released from neutrophils. J. Clin. Invest. 1988; 82: 706-711.

The present invention is not intended to be limited to the foregoing examples, but encompasses all such modifications and variations as come within the scope of the appended claims.

We claim:

1. A method for measuring the activity of a phospholipase, the method comprising the steps of:
providing a liposome consisting of: 1) a nonfluorescent phosphatidylcholine (PC) wherein the nonfluorescent PC is dioleoyl PC (DOPC), 2) a nonfluorescent, negatively charged molecule wherein the nonfluorescent, negatively charged molecule is phosphatidylglycerol (PG) and 3) a fluorescently labeled molecule wherein the fluorescently labeled molecule is 1,2-bis-(4,4-difluoro-5,7-dimethyl-4-bora-3a,4a-diaza-s-indacene-3-undecanoyl)-sn-glycero-3-phosphocholine (BODIPY-PC), wherein hydrolization of the phospholipid components of the liposome by the phospholipase causes a fluorescence intensity change;
contacting the phospholipase with the liposome; and
detecting the fluorescence intensity change due to the hydrolization of the phospholipid components of the liposome by the phospholipase to determine the activity of the phospholipase.

2. The method of claim 1, wherein the phospholipase is selected from phospholipase A1, phospholipase A2, phospholipase C and phospholipase D.

3. The method of claim 2, wherein the phospholipase is phospholipase A2.

4. The method of claim 3, wherein the phospholipase A2 is provided in a biological sample and stimulated by a phospholipase A2 stimulator.

5. The method of claim 4, wherein the biological sample is selected from plasma, serum, bronchoalveolar lavage fluid, sputum, urine, synovial fluid, amniotic fluid, peritoneal fluid, cerebrospinal fluid, pleural fluid, pericardial fluid, white blood cells, and alveolar macrophages.

6. The method of claim 1, wherein the fluorescence intensity is measured at defined intervals over a specific period of time.

7. The method of claim 1, wherein the fluorescently labeled organic compound is dicetyl phosphate.

8. The method of claim 1, wherein the liposome is unilamellar.

9. A kit for measuring the activity of a phospholipase, the kit comprising:
a liposome consisting of: 1) a nonfluorescent phosphatidylcholine (PC) wherein the nonfluorescent PC is dioleoyl PC (DOPC), 2) a nonfluorescent, negatively charged molecule wherein the nonfluorescent, negatively charged molecule is phosphatidylglycerol (PG), and 3) a fluorescently labeled molecule wherein the fluorescently labeled molecule is 1,2-bis-(4,4-difluoro-5,7-dimethyl-4-bora-3a,4a-diaza-s-indacene-3-undecanoyl)-sn-glycero-3-phosphocholine (BODIPY-PC), wherein hydrolization of the phospholipid components of the liposome by the phospholipase causes a fluorescence intensity change; and
the phospholipase.

10. The kit of claim 9, wherein the phospholipase is phospholipase A2.

11. The kit of claim 10 further comprising a calcium source.

12. A method for identifying an agent that can alter the activity of a phospholipase, the method comprising the steps of:
providing a liposome consisting of: 1) a nonfluorescent phosphatidylcholine (PC) wherein the nonfluorescent PC is dioleoyl PC (DOPC), 2) a nonfluorescent, negatively charged molecule wherein the nonfluorescent, negatively charged molecule is phosphatidylglycerol (PG), and 3) a fluorescently labeled molecule wherein the fluorescently labeled molecule is 1,2-bis-(4,4-difluoro-5,7-dimethyl-4-bora-3a,4a-diaza-s -indacene-3-undecanoyl)-sn-glycero-3-phosphocholine (BODIPY-PC), wherein hydrolization of the phospholipid components of the liposome by the phospholipase causes a fluorescence intensity change;

contacting the phospholipase with the liposome in the presence of a test agent;

detecting the fluorescence intensity change due to the hydrolization of the phospholipid components of the liposome by the phospholipase to determine the activity of the phospholipase; and comparing the phospholipase activity to that of a control that is measured in the absence of the test agent wherein a higher than control activity indicates that the agent is a stimulator of the phospholipase and a lower than control activity indicates that the agent is an inhibitor of the phospholipase.

13. The method of claim 12, wherein the phospholipase is selected from phospholipase A1, phospholipase A2, phospholipase C and phospholipase D.

14. The method of claim 13, wherein the phospholipase is phospholipase A2.

* * * * *

UNITED STATES PATENT AND TRADEMARK OFFICE
CERTIFICATE OF CORRECTION

PATENT NO. : 7,579,156 B2  Page 1 of 1
APPLICATION NO. : 10/365738
DATED : August 25, 2009
INVENTOR(S) : Tsao et al.

It is certified that error appears in the above-identified patent and that said Letters Patent is hereby corrected as shown below:

| | | |
|---|---|---|
| Column 7, | line 39 "protein" | should be --proteins-- |
| Column 24, | line 41 "warned" | should be --warmed-- |
| Column 25, | line 40 "run" | should be --nm-- |
| Column 27, | line 14 "µto" | should be --µ to-- |

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,579,156 B2 Page 1 of 1
APPLICATION NO. : 10/365738
DATED : August 25, 2009
INVENTOR(S) : Tsao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1494 days.

Signed and Sealed this

Fourteenth Day of September, 2010

David J. Kappos
*Director of the United States Patent and Trademark Office*